US007445930B2

(12) United States Patent
Zhang et al.

(10) Patent No.: US 7,445,930 B2
(45) Date of Patent: **\*Nov. 4, 2008**

(54) METHOD FOR THE PRODUCTION AND PURIFICATION OF ADENOVIRAL VECTORS

(75) Inventors: Shuyuan Zhang, Sugarland, TX (US);
Capucine Thwin, Seattle, WA (US);
Zheng Wu, Sugarland, TX (US);
Toohyon Cho, Philadelphia, PA (US);
Deborah Wilson, Houston, TX (US);
Lucetta Caston, Limerick, PA (US)

(73) Assignee: Introgen Therapeutics Inc., Austin, TX (US)

( * ) Notice: Subject to any disclaimer, the term of this patent is extended or adjusted under 35 U.S.C. 154(b) by 240 days.

This patent is subject to a terminal disclaimer.

(21) Appl. No.: 10/909,066

(22) Filed: Jul. 30, 2004
(Under 37 CFR 1.47)

(65) Prior Publication Data
US 2005/0089999 A1 Apr. 28, 2005

Related U.S. Application Data

(60) Division of application No. 10/033,571, filed on Dec. 27, 2001, which is a continuation of application No. 09/556,570, filed on Apr. 24, 2000, now Pat. No. 6,726,907, which is a continuation of application No. 08/975,519, filed on Nov. 20, 1997, now Pat. No. 6,194,191.

(60) Provisional application No. 60/031,329, filed on Nov. 20, 1996.

(51) Int. Cl.
*C12N 15/00* (2006.01)
*A61K 39/00* (2006.01)
*A61K 39/23* (2006.01)
*A61K 39/095* (2006.01)

(52) U.S. Cl. ............... 435/320.1; 424/184.1; 424/233.1
(58) Field of Classification Search ........................ None
See application file for complete search history.

(56) References Cited

U.S. PATENT DOCUMENTS

| 4,222,743 | A | 9/1980 | Wang et al. |
| 4,352,883 | A | 10/1982 | Lim |
| 4,725,547 | A | 2/1988 | Sakamoto et al. |
| 4,797,368 | A | 1/1989 | Carter et al. |
| 5,106,841 | A | 4/1992 | Scheer |
| 5,139,941 | A | 8/1992 | Muzyczka et al. |
| 5,173,418 | A | 12/1992 | Molin et al. |
| 5,219,752 | A | 6/1993 | Takazawa et al. |
| 5,221,958 | A | 6/1993 | Bohnenkamp et al. |
| 5,323,008 | A | 6/1994 | Studholme et al. |
| 5,552,309 | A | 9/1996 | March |
| 5,604,096 | A | 2/1997 | Schaeffer et al. |
| 5,607,851 | A | 3/1997 | Pellegrini et al. |
| 5,623,932 | A | 4/1997 | Ramanujam et al. |
| 5,631,169 | A | 5/1997 | Lakowicz et al. |
| 5,665,546 | A | 9/1997 | Cubbage et al. |
| 5,670,488 | A | 9/1997 | Gregory et al. |
| 5,733,720 | A | 3/1998 | Olivo |
| 5,741,648 | A | 4/1998 | Hemstreet, III et al. |
| 5,744,304 | A | 4/1998 | Munford |
| 5,789,244 | A | 8/1998 | Heidrun et al. |
| 5,824,544 | A | 10/1998 | Armentano et al. |
| 5,830,666 | A | 11/1998 | Fujita et al. |
| 5,837,520 | A | 11/1998 | Shabram et al. |
| 5,932,210 | A | 8/1999 | Gregory |
| 5,965,358 | A | 10/1999 | Carrion et al. |
| 6,143,290 | A | 11/2000 | Zhang et al. |
| 6,143,548 | A | 11/2000 | O'Riordan et al. |
| 6,168,944 | B1 | 1/2001 | Condon et al. |
| 6,194,191 | B1 * | 2/2001 | Zhang et al. ................ 435/239 |
| 6,194,210 | B1 | 2/2001 | Leu et al. |
| 6,261,823 | B1 | 7/2001 | Tang et al. |
| 6,265,151 | B1 | 7/2001 | Canter et al. |

(Continued)

FOREIGN PATENT DOCUMENTS

EP 0273085 7/1988

(Continued)

OTHER PUBLICATIONS

Berg et al., High-Level Expression of Secreted Proteins from Cells Adapted to Serum-Free Suspension Culture, 1993, BioTechniques, vol. 14, No. 6, pp. 972-978.*

(Continued)

*Primary Examiner*—Bruce Campell
*Assistant Examiner*—Benjamin P Blumel
(74) *Attorney, Agent, or Firm*—Marshall, Gerstein & Borun LLP

(57) ABSTRACT

The present invention addresses the need to improve the yields of viral vectors when grown in cell culture systems. In particular, it has been demonstrated that for adenovirus, the use of low-medium perfusion rates in an attached cell culture system provides for improved yields. In other embodiments, the inventors have shown that there is improved Ad-p53 production witrh cells grown in serum-free conditions, and in particular in serum-free suspension culture. Also important to the increase of yields is the use of detergent lysis. Combination of these aspects of the invention permits purification of virus by a single chromatography step that results in purified virus of the same quality as preparations from double CsCl banding using an ultracentrifuge.

29 Claims, 44 Drawing Sheets

U.S. PATENT DOCUMENTS

| | | | |
|---|---|---|---|
| 6,316,185 | B1 | 11/2001 | Saifer et al. |
| 6,383,795 | B1 | 5/2002 | Carrion et al. |
| 6,410,010 | B1 | 6/2002 | Zhang et al. |
| 6,447,995 | B1 | 9/2002 | Carrion et al. |
| 6,485,958 | B2 | 11/2002 | Blanche et al. |
| 6,531,317 | B2 | 3/2003 | Guriguis et al. |
| 6,537,793 | B2 | 3/2003 | Blanche et al. |
| 6,586,226 | B2 | 7/2003 | Carrion et al. |
| 6,689,600 | B1 | 2/2004 | Wu et al. |
| 6,726,904 | B2 | 4/2004 | Krauss et al. |
| 6,726,907 | B1 | 4/2004 | Zhang et al. |
| 6,740,320 | B1 | 5/2004 | Zhang et al. |
| 6,905,862 | B2 * | 6/2005 | Blanche et al. ............. 435/239 |
| 7,125,706 | B2 | 10/2006 | Zhang et al. |
| 2002/0018723 | A1 | 2/2002 | Mera et al. |
| 2002/0045160 | A1 | 4/2002 | Carrion et al. |
| 2002/0177215 | A1 | 11/2002 | Zhang et al. |
| 2003/0008375 | A1 | 1/2003 | Zhang et al. |
| 2003/0166603 | A1 | 9/2003 | Clayman et al. |
| 2004/0106184 | A1 * | 6/2004 | Senesac ...................... 435/239 |
| 2004/0229335 | A1 * | 11/2004 | Zhang et al. ............. 435/235.1 |
| 2005/0158283 | A1 * | 7/2005 | Zhang et al. ............... 424/93.2 |
| 2006/0035857 | A1 | 2/2006 | Clayman et al. |
| 2007/0155008 | A1 | 7/2007 | Zhang et al. |

FOREIGN PATENT DOCUMENTS

| | | |
|---|---|---|
| EP | 0475623 A1 | 3/1992 |
| JP | 1279843 | 11/1989 |
| JP | 4-9338 | 1/1992 |
| WO | WO-90/08444 | 7/1990 |
| WO | WO-91/09310 | 6/1991 |
| WO | WO-93/18790 | 9/1993 |
| WO | WO93/25224 | 12/1993 |
| WO | WO94/06910 | 3/1994 |
| WO | WO94/17178 | 8/1994 |
| WO | WO-94/26934 | 11/1994 |
| WO | WO95/06743 | 3/1995 |
| WO | WO-95/10601 | 4/1995 |
| WO | WO-95/19427 | 7/1995 |
| WO | WO95/25789 | 8/1995 |
| WO | WO-95/24468 | 9/1995 |
| WO | WO96/09399 | 3/1996 |
| WO | WO96/27677 | 9/1996 |
| WO | WO-96/32116 | 10/1996 |
| WO | WO97/04803 | 2/1997 |
| WO | WO97/08298 | 3/1997 |
| WO | WO98/00524 | 1/1998 |
| WO | WO-98/22588 | 5/1998 |
| WO | WO-98/26048 | 6/1998 |
| WO | WO-98/35554 | 8/1998 |
| WO | WO-99/12568 | 3/1999 |
| WO | WO-99/41416 | 8/1999 |
| WO | WO-99/43843 | 9/1999 |
| WO | WO-99/46047 | 9/1999 |
| WO | WO-99/54348 | 10/1999 |
| WO | WO-99/54441 | 10/1999 |
| WO | WO-99/60371 | 11/1999 |
| WO | WO-00/08444 | 2/2000 |
| WO | WO-00/32754 | 6/2000 |
| WO | WO-00/34444 | 6/2000 |
| WO | WO-00/40702 | 7/2000 |
| WO | WO-02/29388 | 4/2002 |

OTHER PUBLICATIONS

Huyghe et al., Purification of a Type 5 Recombinant Adenovirus Encoding Human p53 by Column Chromatography, 1995, Human Gene Therapy, vol. 6, pp. 1403-1416.*

Wills et al., Development and Characterization of Recombinant Adenoviruses Encoding Human p53 for Gene Therapy of Cancer, 1994, Human Gene Therapy, vol. 5, pp. 1079-1088.*

Keay L., Autoclavable Low Cost Serum-Free Cell Culture Media: The Growth of Established Cell Lines and Production of Viruses, 1976, Biotechnology and Bioengineering, vol. 48, pp. 363-382.*

Kozak et al., Transmissible Spongiform Encephalophathies (TSE): Minimizing the Risk of Transmission by Biological/Biopharmaceutical Products: an Industry Perspective, 1996, Developments in Biological Standardization, vol. 88, pp. 257-264.*

Nadeau et al., Improvement of Recombinant Protein Production with the Human Adenovirus/293S Expression System Using Fed-Batch Stratagies, 1996, Biotechnology and Bioengineering, vol. 51, pp. 613-623.*

Aboud, et al. "Rapid purification of extracellular and intracellular moloney murine leukemia virus," Arch. Virol., 71:185-195, 1982.

Berg, et al. "High-live expression of secreted proteins from cells adapted to serum-free suspension culture," BioTechniques, 14(6):972-978, 1993.

Bett "An efficient and flexible system for construction of adenovirus vectors with insertions or deletions in early regions 1 and 3," Proc. Natl. Acad. Sci. USA, 91(19):8802-8806, 1994.

Cartwright "Animal cells as bioreactors," Cambridge University Press, pp. 58-63, 1994.

Complaint *Aventis Pharmaceuticals Products, Inc. and Aventis Pharma, S.A.*, Plaintiffs, v. *Introgen Therapeutics, Inc.*, Defendant. Civil Action No. 01-451 from the U.S. District Court for the District of Delaware, Jun. 29, 2001, dismissed with prejudice Jul. 2, 2001.

Crooks, et al. "Purification and analysis of infections virions and native non-structural antigens from cells infected with tick-borne encephalitis virus," J. Chrom., 502:59-68, 1990.

Garnier, et al. "Scale-up of the adenovirus expression system for the production of recombinant protein in human 293S cells," Cytotechnol., 15:145-155, 1994.

Gilbert "Adaptation of cells to serum-free culture for production of adenovirus vectors and recombinant proteins," Williamsburg BioProcessing Conference, Nov. 18-21, 1996.

Graham "Growth of 293 Cells in Suspension Culture," J. Gen. Virol., 68:937-940, 1987.

Graham and Prevec "Manipulation of adenovirus vectors," Int. Methods in Molecular Biology: Gene Transfer and Expression Protocols 7, (Murray, Ed.) Humana Press, Clifton, NJ, pp. 109-128, 1991.

Graham, et al. "Characteristics of a human cell line transformed by DNA from human adenovirus type 5," J. Gen. Virol., 36:59-72, 1977.

Griffiths, "Overview of cell culture systems and their scale-up," In: Animal Cell Biotechnology, 3:179-220, 1986.

Haruna, et al. "Separation of Adenovirus by Chromatography on DEAE-Cellulose," Discussion and Preliminary Reports, pp. 264-267.

Hay, et al. "Replication of adenovirus mini-chromosomes," J. Mol. Biol., 175:493-510, 1984.

Hearing and Shenk, "Functional analysis of the nucleotide sequence surrounding the cap site for adenovirus type 5 region EIA messenger RNAs," J. Mol. Biol., 167:809-822, 1983.

Hearing, et al. "Identification of a repeated sequence element required for efficient encapsidation of the adenovirus type 5 chromosome," J. Virol., 61:2555-2558, 1987.

Huyghe, et al. "Purification of a type 5 recombinant adenovirus encoding human p53 by column chromatography," Hum. Gene Ther., 6:1403-1416, 1996.

International Search Report dated Jul. 16, 1998 (PCT/US97/21504) (INGN:058P).

Jones and Shenk, "Isolation of deletion and substitution mutants of adenovirus type 5," Cell, 13:181-188, 1978.

Larsson and Litwin "The growth of polio virus in human diploid fibroblasts grown with cellulose microcarriers in suspension cultures," Dev. Bio. Standard, 66:385-390, 1987.

Lentfer, et al: "A Rapid and Inexpensive Procedure for the Purification of Adenovirions," 1978.

Levrero, et al. "Defective and nondefective adenovirus vectors for expressing foreign genes in vitro and in vivo," Gene, 101:195-202, 1991.

Mann, et al. "Construction of a retrovirus packaging mutant and its use to produce helper-free defective retrovirus," Cell, 33:153-159, 1983.

McGrath, et al. "Retrovirus purification: method that conserves envelope glycoprotien and maximizes infectivity," J. Virol., 25:923-927, 1978.

Mizrahi "Production of human interferons—an overview," Proc. Biochem., (Aug.):9-12, 1983.

Montagnon, B.J. "Polio and Rabies Vaccines Produced in Continuous Cell Lines: A Reality for Vero Cell Line," 1989.

Morris, et al. "Serum-free production of adenoviral vectors for gene therapy," Williamsburg BioProcessing Conference, Nov. 18-21, 1996.

Nadeau, et al. "Improvement of Recombinant Protein Production with the Human Adenovirus/293S Expression System Using Fed-Batch Strategies," Biotechnology and Bioengineering, 51:613-623, 1996.

Nicolas, et al. "Vectors: a survey of molecular cloning vectors and their uses," In: Vectors: A survey of molecular cloning vectors and their uses, (Rodriguez and Behhardt, eds.), Stoneham: Butterworth, pp. 493-513, 1988.

Nilsson, et al. "Immobilized animal cells," Dev. Biol. Standard, 66:183-193.

O'Neil, et al. "Virus harvesting and affinity-based liquid chromatography," Bio. Technol., 11:173-178, 1993.

Payment, et al. in Biotechnology Current Progress, Eds. Paul Cheremisinoff and Louise Ferrante, Technomic Publishing Co., Lancaster/Basel, vol. 1, pp. 61-82, 1991.

PCT Search Report dated Nov. 28, 2003, Application No. EP 97 95 0677.1.

Perrin, et al. "An experimental-rabies vaccine produced with a new BHK-21 suspension cell culture process; use of serum-free medium and perfusion-reactor system," Vaccine, 13(13):1244-1250, 1995.

Petricciani "Should continuous cell lines be used as substrates for biological products?," Dev. Biol. Standard, 66:3-13, 1985.

Phillips, et al. "Experience in the cultivation of mammalian cells on the 8000 l scale," In: Large Scale Mammalian Cell Culture (Feder and Tolbert, eds.), Academic Press, Orlando, FL, U.S.A., 1985.

U.S. Appl. No. 60/026,667, Entitled: "Method for the Production of Recombinant Adenoviruses," RPR File No. ST96021-US., Translated from the French by the Medical Documentation Service* Institute for Scientific Information* Philadelphia, Pennsylvania.

Roux, et al. "A versatile and potentially general approach to the targeting of specific cell types by retroviruses: application to the infection of human cells by means of major histocompatibility complex class I and class II antigens by mouse ecotropic murine leukemia virus-derived viruses," Proc. Nat'l Acad. Sci. USA, 86:9079-9083, 1989.

Smith, et al. "Large-scale isolation and partial purificationof type C RNA viruses on hydroxyapatite," Analytical Biochem., 86:252-263, 1978.

Temin "Retrovirus vectors for gene transfer: efficient integration into and expression of exogenous DNA in vertebrate cell genomes," In: Gene Transfer (Kucherlapati, ed.), Plenum Press, New York, pp. 149-188, 1986.

Tibbetts "Viral DNA sequences from incomplete particles of human adenovirus type 7," Cell, 12:243-249, 1977.

Trepanier, et al. "Concentration of Human Respiratory Syncytial Virus Using Ammonium Sulfate, Polyethylene Glycol or Hollow Fiber Ultrafiltration," Journal of Virological Methods, 3:201-211, 1981.

van Wezel "Growth of cell-strains and primary cells on micro-carriers in homogeneous culture," Nature, 216:64-65, 1967.

Wang, et al. "High cell density perfusion culture of hybridoma cells for production of monoclonal antibodies in the celligen packed bed reactor," In: Animal Cell Technology: Basic & Applied Aspects (Kaminogawa, et al. eds.), Kluwer Academic Publishers, Netherlands, 5:463-469, 1993.

Wang, et al. "Modified CelliGen-packed bed bioreactors for hybridoma cell cultures," Cytotechnol., 9:41-49, 1992.

Wills, et al. "Adenovirus Vectors of Gene Therapy of Cancer," Journal of Cellular Biochemistry, Supp. 17E, S216:206, 1993.

Cote et al., "Study of Adenovirus Production in Serum-Free 293SF Suspension Culture by GFP-Expression Monitoring" Biotechnol. Prog., 1997, 13, 709-714, Biotechnology Research Institute, National Research Council Canada, 6100 Royalmount Avenue, Montreal, Quebec, Canada H4P 2R2, S8756-7938(97)00110-0 CCC, 1997 American Chemical Society and American Institute of Chemical Engineers.

Massie et al., "Improved Adenovirus Vector Provides Herpes Simplex Virus Ribonucleotide Reductase R1 and R2 Subunits Very Efficiently" Biotechnology, vol. 13; 602-608, Jun. 1995, Institute of Research in Biotechnology, Montreal, Quebec, Canada H4P 2R2; Institute of Cancer of Montreal, Quebec, Canada H2I 4MI, 1995 Nature Publishing Group.

Zhang et al., "Adenovirus Inhibition of Cell Translation Facilitates Release of Virus Particles and Enhances Degradation of the Cytokeratin Network", Journal of Virology, Apr. 1994, p. 2544-2555, 00022-538X/94, 1994 American Society for Microbiology, Department of Biochemistry and Kaplan Cancer Center, New York University School of Medicine, New York, New York 10016.

Haruna, et al., "Separation of Adenovirus by Chromatography on DEAE-Cellulose", Discussion and Preliminary Reports, pp. 264-267; Institute for Virus Research, Kyoto University, Kyoto, Japan—Sep. 22, 1960.

U.S. Appl. No. 60/026,667, filed Sep. 25, 1996, Guillaume et al.

U.S. Appl. No. 60/082,628, filed Apr. 22, 1998, Carrion et al.

Arap et al., "Replacement of the p16/CDKN2 gene suppresses human glioma cell growth," Cancer Res., 55:1351-1354, 1995.

Baichwal and Sugden, In: Kucherlapati R, ed. Gene Transfer. New York: Plenum Press, pp. 117-148, 1986.

Batra et al., "IkappaBalpha gene transfer is cytoxic to squamous-cell lung cancer cells and sensitizes them to tumor necrosis factor-alpha-mediated cell death," Am. J. Respir. Cell Mol. Biol., 21:238-245, 1999.

Benvenisty and Neshif, "Direction introduction of genes into rats and expression of the genes," Proc. Nat'l Acad. Sci. USA, 83:9551-9555, 1986.

Blackwell et al., "Retargeting to EGFR enhances adenovirus infection efficiency of squamous cell carcinoma," Arch. Otolaryngol Head Neck Surg., 125:856-863, 1999.

Bussemakers et al., "Decreased expression of E-cadherin in the progression of rat prostatic cancer," Cancer Res., 52:2916-2622, 1992.

Butman et al., "High sensibitivity HPLC method for determining viral particle concentration," Presentation, 2000.

Caldas et al., "Frequent somatic mutations and homozygous deletions of the p16 (MTSI) gene in pancreatic adenocarcinoma," Nat. Genet., 8:27-32, 1994.

Carrion et al., "Intrinsic fluorescence of adenovirus type S: A sensitive detection alternative," Molecular Ther., 3:438, 2001.

Cartwright, "Fermenter design for animal cell cultures," Animal Cells as Bioreactors, Cambridge University Press, 58-63, 1994.

Carver et al., "Transgenic livestock as bioreactors: stable expression of human alpha-1-antitrypsin by a flock of sheep," Biotechnology NY, 11:1263-1270, 1993.

Casey et al., "Growth suppression of human breast cancer cells by the introduction of a wild-type p53 gene," Oncogene, 6:1791-1797, 1991.

Chen and Okayama, "High-efficiency transfection of mammalian cells by plasmid DNA," Mol. Cell Biol., 7:2745-2752, 1987.

Cheng et al., "p16 Alterations and deletion mapping of 9p21-p22 in malignant mesothelioma," Cancer Res., 54:5547-5551, 1994.

Cheung et al., "Cell-CAM105 isoforms with different adhesion functions are coexpressed in adult rat tissues and during liver development," J. Biol. Chem., 268:6139-6146, 1993.

Cheung et al., "Structure and function of C-CAM1," J. Biol. Chem., 268(32):24303-24310, 1993.

Cheung et al., "the cytoplaxmic domain of C-CAM is required for C-CAM-mediated adhesion function: studies of a C-CAM transcript containing an unspliced intron," Biochem. J., 295:427-435, 1993.

Chillon et al., "Group D adenoviruses infect primary central nervous system cells more efficiently than those from Group C," J. Virol., 73:2537-2540, 1990.

Chroboczek et al., "The sequence of the genome of adenovirus Type 5 and its comparison with the genome of adenovirus Type 2," Virology, 186:280-285, 1992.

Coffin, "Retroviridae and their application," In: Virology, Fields et al. (eds.), New York: Raven Press, pp. 1437-1500, 1990.

Corveleyn and Remon, "Maltodextrins as lyoprotectants in the lyophilization of a model protein, LDH," *Pharm. Res.*, 13:146-150, 1996.

Coupar et al., "A general method for the construction of recombinant vaccinia virus expressing multiple foreign genes," *Gene*, 68:1-10, 1988.

Cristiano et al., "Viral and nonviral gene delivery vectors for cancer gene therapy," *Cancer Detect Prev.*, 22:445-454, 1998.

Croyle et al., "Factors that influence stability of recombinant adenoviral preparations for human gene therapy," *Pharm. Dev. Technol*, 3(3):373-383, 1998.

Declaration of Peter Clark, Ph.D.: submitted in European Patent Application No. 97950677.1.

Dorai et al., "A recombinant defective adenoviral agent expressing anti-bcl-2 ribozyme promotes apoptosis of bcl-2-expressing human prostate cancer cells," *Int. J. Cancer*, 82:846-852, 1999.

Dubensky et al., "Direct transfection of viral and plasmid DNA into the liver or spleen of mice," *Proc. Nat. Acad. Sci. USA*, 81:7529-7533, 1984.

Edelman and Crossin, "Cell adhesion molecules: implications for a molecular histology," *Annu. Rev. Biochem.*, 60:155-190, 1991.

Edelman, "Cell adhesion and the molecular processes of morphogenesis," *Annu. Rev. Biochem.*, 54:135-169, 1985.

Fechheimer et al., "Transfection of mammalian cells with plasmid DNA by scrape loading and sonication loading," *Proc. Nat. Acad. Sci. USA*, 84:8463-8467, 1987.

Feldman et al., "Perspectives of arterial gene therapy for the prevention of restenosis," *Cardiovasc. Res.*, 32:194-204, 1996.

Ferkol et al., "Regulation of the phosphoenolpyruvate carboxykinase/human factor IX gene introduced into the livers of adult rats by receptor-mediated gene transfer," *FASEB J.*, 7:1081-1091, 1993.

Fraley et al., "Entrapment of a bacterial plasmid in phospholipid vesicles: potential for gene transfer," *Proc. Nat. Acad. Sci. USA*, 76:3348-3352, 1979.

Freshney, "Animal Cell Culture: a Practical Approach," Second Edition, Oxford/New York, IRL Press, Oxford University Press, 1992.

Fried and Bromberg, "Factors that affect the stability of protein-DNA complexes during gel electrophoresis," *Electrophoresis*, 18:6-11, 1997.

Frixen et al., "E-cadherin-mediated cell-cell adhesion prevents invasiveness of human carcinoma cells," *J. Cell Biol.*, 113:173-185, 1991.

Ghosh and Bachhawat, In: Liver Disease, Targeted Diagnosis and Therapy using Specific Receptors and Ligands, Wu G, Wu C (eds.), Marcel Dekker, New York, pp. 87-104, 1991.

Giancotti and Ruoslahti, "Elevated levels of the $\alpha_5\beta_1$ fibronectin receptor suppress the transformed phenotype of Chinese hamster ovary cells," *Cell*, 60:849-859, 1990.

Gopal, "Gene transfer method for transient gene expression, stable transfection, and cotransfection of suspension cell cultures," *Mol. Cell Biol.*, 5:1188-1190, 1985.

Graham and Prevec, "Methods for construction of adenovirus vectors," *Mol. Biotechnol.*, 3:207-220, 1995.

Graham and Van Der Eb, "A new technique for the assay of infectivity of human adenovirus 5 DNA," *Virology*, 52:456-467, 1973.

Hall et al., "Stabilizing effect of sucrose against irreversible denaturation of rabbit muscle lactate dehydrogenase," *Biophys. Chem.*, 57:47-54, 1995.

Harland and Weintraub, "Translation of mammalian mRNA injected into *Xenopus ooctyes* is specifically inhibited by antisense RNA," *J. Cell Biol.*, 101:1094-1099, 1985.

Herman et al., "The effect of bulking agent on the solid-state stability of freeze-dried methylprednisolone sodium succinate," *Pharm. Res.*, 11:1467-1473, 1994.

Hermens and Verhaagen, "Viral vectors, tools for gene transfer in the nervous system," *Prog. Neurbiol.*, 55:399-432, 1998.

Hermonat and Muzyscka, "Use of adenoassociated virus as a mammalian DNA cloning vector: Transduction of neomycin resistance into mammalian tissue culture cells," *Proc. Nat. Acad. Sci. USA*, 81:6466-6470, 1984.

Hollstein et al., "p53 mutations in human cancers," *Science*, 253:49-53, 1991.

Hurwitz et al., "Suicide gene therapy for treatment of retinoblastoma in a murine model," *Human Gene Therapy*, 10:441-448, 1999.

Hussussian et al., "Germline p16 mutations in familial melanoma," *Nature Genetics*, 8(1):15-21, 1994.

Irie et al., "Therapeutic efficacy of an adenovirus-mediated anti-H-ras ribozyme in experimental bladder cancer," *Antisense Nucleic Acid Drug Dev.*, 9:341-349, 1999.

Ishibashi et al., "Hypercholesterolemia in low density lipoprotein receptor knockout mice and its reversal by adenovirus-mediated gene delivery," *J. Clin. Invest.*, 92:883-893, 1993.

Jardon and Garnier, "PH, pCO2, and temperature effect on R-adenovirus production," *Biotechnol. Prog.*, 19:202-208, 2003.

Jiang et al., "The melanoma differentiation associated gene mda-7 suppresses cancer cell growth," *Proc. Nat. Acad. Sci. USA*, 93:9160-9165, 1996.

Jul. 17, 2006: Minutes of Oral Proceedings Before the Examining Division with decision to grant European Patent Application No. 97950677.1.

Kamb et al., "A cell cycle regulator potentially involved in genesisi of many tumor types," *Science*, 264:436-440, 1994.

Kamb et al., "Analysis of the p16 gene (CDKN2) as a candidate for the chromosome 9p melanoma susceptibility locus," *Nature Genetics*, 8:22-26, 1994.

Kaneda et al., "Increased expression of DNA cointroduced with nuclear protein in adult rat liver," *Science*, 243:375-378, 1989.

Kato et al., "Expression of hepatitis b virus surface antigen in adult rat liver," *J. Biol. Chem.*, 266:3361-3364, 1991.

Klein et al., "High-velocity microprojectiles for delivering nucleic acids into living cells," *Nature*, 327:70-73, 1987.

Kotani et al., "Improved methods of retroviral vector transduction and production for gene therapy," *Human Gene Therapy*, 5:19-28, 1994.

Kraft et al., "Cell cycle-dependent multiplications of avian adenovirus in chicken embryo fibroblasts," *Archives of Virology*, 57:243-254, 1978.

Lesch, "Gene transfer to the brain: emerging therapeutic strategy in psychiatry?," *Biol. Psychiatry*, 45:247-253, 1999.

Lin and Guidotti, "Cloning and expression of a cDNA coding for a rat liver plasma membrane ecto-ATpase," *J. Biol. Chem.*, 264:14408-14414, 1989.

Lu et al., "Coat protein interactions involved in tobacco mosaic tobamovirus cross-protection," *Virology*, 248:188-198, 1998.

Lueckel et al., "Formulations of sugars with amino acids or mannitol-influence of concentration ratio on the properties of the freeze-concentrate and the lyophilizate," *Pharm. Dev. Technol.*, 3:326-336, 1998.

Marienfeld et al., "Autoreplication of the vector genome in recombinant adenoviral vectors with different E1 region deletions and transgenes," *Gene Ther.*, 6:1101-1113, 1999.

Matsuura et al., "Altered expression of e-cadherin in gastric cancer tissues and carcinomatous fluid," *Brit. J. Cancer*, 66:1122-1130, 1992.

Mercer, "Cell cycle regulation and the p53 tumor suppressor protein," *Critic. Rev. Eukar. Gene Express*, 2:251-263, 1992.

Mincheff et al., "Naked DNA and adenoviral immunizations for immunotherapy of prostate cancer: a phase I/II clinical trial," *Eur. Urol.*, 38:208-217, 2000.

Mori et al., "Frequent somatic mutation of the *MTSI/CDK4I* (Multiple Tumor suppressor/Cyclin dependent Kinase 4 Inhibitor) gene in esophageal squamous cell carcinoma," *Cancer Res.*, 54:3396-3397, 1994.

Morrison et al., "Complete DNA sequence of canine adenovirus type 1," *J. Gen. Virol.*, 78:873-878, 1997.

Murakami et al., "Quantitation of adenovirus DNA and virus particles with the PicoGreen fluorescent Dye," *Analytical Biochemistry*, 274:283-288, 1999.

Murphy et al., Virus taxonomy, in B.N. Fields et al. (ed.), Fields Virology, 3rd edition Philadelphia: Lippencott-Raven Publishers: Table 6, pp. 51-54, 1996.

Nicolau and Sene, "Liposome-mediated DNA transfer in eukaryotic cells," *Biochem. Biophys. Acta*, 721:185-190, 1982.

Nicolau et al., "Liposomes as carriers for in vivo gene transfer and expression," *Methods Enzymol.*, 149:157-176, 1987.

Nobori et al., "Deletions for the cyclin-dependent kinase-4 inhibitor gene in multiple human cancers," *Nature*, 368:753-756, 1994.

Obrink, "C-CAM (cell-CAM 105)—a member of the growing immunogloublin superfamily of cell adhesion proteins," *BioEssays*, 13:227-233, 1991.

Odin and Obrink, "Quantitative determination of the organ distribution of the cell adhesion molecule cell-CAM 105 by radioimmunoassy," *Exp. Cell Res.*, 171:1-15, 1987.

Okamoto et al., "Mutations and altered expression of p16$^{INK4}$ in human cancer," *Proc. Nat. Acad. Sci. USA*, 91:11045-11049, 1994.

Orlow et al., "Chromosome 9 allelic losses and microsatellite alterations in human bladder tumors," *Cancer Res.*, 54:2848-2851, 1994.

Parks et al., "A helper-dependent system for adenovirus vector production helps define a lower limit for efficient DNA packaging," *J. Virol.*, 71:3293-3298, 1997.

Paskind et al., "Dependence of moloney murine leukemia virus production on cell growth," *Virology*, 67:242-248, 1975.

Perales et al., "Gene transfer in vivo: sustained expression and regulation of genes introduced into the liver by receptor-targeted uptake," *Proc. Nat. Acad. Sci. USA*, 91:4086-4090, 1994.

Petrof, "Respiratory muscles as a target for adenovirus-mediated gene therapy," *Eur. Respir. J.*, 11:492-497, 1998.

Potter et al., "Enhancer-dependent expression of human k immunoglobullin genes introduced into mouse pre-B lymphocytes by electroporation," *Proc. Nat. Acad. Sci. USA*, 81:7161-7165, 1984.

Racher et al., "Culture of 293 cells in different culture systems: cell growth and recombinant adenovirus production," *Biotechnology Techniques*, 9:169-174, 1995.

Reddy et al., "Nucleotide sequence and transcription map of porcine adenovirus type 3," *Virology*, 251:414-426, 1998.

Renan, "Cancer genes: current status, future prospects, and applications in radiotherapy/oncology," *Radiother. Oncol.*, 19:197-218, 1990.

Ridgeway, "Mammalian expression vectors," *In*: Rodriguez RL, Denhardt DT, ed. Vectors: A survey of molecular cloning vectors and their uses. Stoneham: Butterworth, pp. 467-492, 1988.

Rippe et al., "DNA-mediated gene transfer into adult rat hepatocytes in primary culture," *Mol. Cell Biol.*, 10:689-695, 1990.

Robbins and Ghivizzani, "Viral vectors for gene therapy," *Pharmacol. Ther.*, 80:35-47, 1998.

Robbins et al., "Viral vectors for gene therapy," *Trends Biotechnol.*, 16:35-40, 1998.

Sagrera et al., "Study of the influence of salt concentration on Newcastle disease virus matrix protein aggregation," *Biochem. Mol. Biol. Int.*, 46:429-435, 1998.

Serrano et al., "A new regulatory motif in cell-cycle control causing specific ihyibition of cyclin D/CDK4," *Nature*, 366:704-707, 1993.

Serrano et al., "Inhibition of ras-induced proliferation and cellular transformation by p16$^{INK}$4," *Science*, 267:249-252, 1995.

Shabram et al., "Analytical anlon-exchange HPLC of recombinant type-5 adenoviral particles," *Human Gene Therapy*, 8:453-465, 1997.

Stewart et al., "Adenovector-mediated gene delivery of interleukin-2 in metastatic breast cancer and melanoma: results of a phase 1 clinical trial," *Gene Ther.*, 6:350-363, 1999.

Takahasi et al., "Wild-type but not mutant p53 suppresses the growth of human lung cancer cells bearing multiple genetic lesions," *Cancer Res.*, 52:2340-2342, 1992.

Tur-Kaspa et al., "Use of electroporation to introduce biologically active foreign genes into primary rat hepatocytes," *Mol. Cell Biol.*, 6:716-718, 1986.

Umbas et al., "Expression of the cellular adhesion molecule E-cadherin is reduced or absent in high-grade prostate cancer," *Cancer Res.*, 52:5104-5109, 1992.

Vanderkwaak and Alvarez, "Immune directed therapy for ovarian carcinoma," *Curr. Opin. Obstet. Gynecol.*, 11:29-34, 1999.

Vanlandschoot et al., "pH-dependent aggregation and secretion of soluble monomeric influenza hemagglutinin," *Arch. Virol.*, 143:227-239, 1998.

Vossen and Fried, "Sequestration stabilizes lac repressor-DNA complexes during gel electrophoresis," *Anal. Biochem.*, 245:85-92, 1997.

Wagner et al., "Antisense gene inhibition by oligonucleotides containing C-5 propyne pyrimidines," *Science*, 260:1510-1513, 1990.

Wagner et al., "Transferrin-polycation conjugates as carriers for DNA uptake into cells," *Proc. Nat. Acad. Sci. USA*, 87(9):3410-3414, 1990.

Watt et al., "Human prostate-specific antigen: structural and functional similarity with serine proteases," *Proc. Nat. Acad. Sci. USA*, 83(2):3166-3170, 1986.

Weinberg, "Tumor suppressor genes," *Science*, 254:1138-1145, 1991.

Wilson, "Vehicles for gene therapy," *Nature*, 365:691-692, 1993.

Wilson, "When bad gene transfer is good," *J. Clin. Invest.*, 98:2435, 1996.

Wong et al., "Appearance of b-lactamase activity in animal cells upon liposome mediated gene transfer," *Gene*, 10:87-94, 1980.

Wu and Wu, "Evidence for targeted gene delivery to HepG2 hepatoma cells in vitro," *Biochemistry*, 27:887-892, 1988.

Wu and Wu, "Liver-directed gene delivery," *Adv. Drug Delivery Rev.*, 12:159-167, 1993.

Wu and Wu, "Receptor mediated in vitro gene transfections by a soluble DNA courier system," *J. Biol. Chem.*, 262:4429-4432, 1987.

Yang et al., "In vitro gene transfer to mammalian somatic cells by particle bombardment," *Proc. Nat. Acad. Sci. USA*, 87:9568-9572, 1990.

Yotnda et al., "Efficient infection of primitive hematopoietic stem cells by modified adenovirus," *Gene Ther.*, 8:930/937, 2001.

Zheng et al., "Transcription units of E1a, E1b and pIX regions of bovine adenovirus type 3," *J. Gen. Virol.*, 80:1735-1742, 1999.

Air Force Print News, Oct. 7, 2004, New Adenovirus Vaccine "Top Priority", Website, Printed Out on Oct. 27, 2004, hhttp://www.af.mil/news/story_print.asp?storyID=123008879.

Bramble, "Fluorescence Spectroscopy as an Aid to Imaging Latent Fingermarks in the Ultraviolet" *Forensic Sci.*, 41:1038-1041 (1996).

Brock et al., "Rapid Characterization of Green Fluorescent Protein Fusion Proteins on the Molecular and Cellular Level by Fluorescence Correlation Microscopy," *Proc. Natl. Acad. Sci. USA*, 96:10123-10128 (1999).

Centers for Disease Control and Prevention, Adenoviruses, Website, Printed Out on Oct. 27, 2004, hhttp://www.cdc.gov/ncidod/dvrd/revb/respiratory/eadfeat.htm.

Chapeaurouge et al., "Folding Intermediates of a Model Three-Helix Bundle Protein," *J. Biol. Chem.*, 276:14861-14866 (2001).

Deniz et al., "Single-Pair Fluorescence Resonance Energy Transfer on Freely Diffusing Molecules: Observation of Förster Distance Dependence and Subpopulations," *Proc. Natl. Acad. Sci. USA*, 96:3670-3675 (1999).

Denk et al., "Two-Photon Laser Scanning Fluorescence Microscopy," *Science*, 248:73-76 (1990).

Deonarain, "Ligand-Targeted Receptor-Mediated Vectors for Gene Delivery," *Exp. Opin. Ther. Pat.*, 8(1):53-69 (1998).

Dickson et al., "On/Off Blinking and Switching Behaviour of Single Molecules of Green Fluorescent Protein," *Nature*, 388:355-358 (1997).

Eck et al., Goodman & Gilman's The Pharmacological Basis of Therapeutics, 9th Ed., McGraw-Hill, New York, NY, pp. 77-101 (1996).

Eggeling et al., "Monitoring Conformational Dynamics of a Single Molecule by Selective Fluorescence Spectroscopy," *Proc. Natl. Acad. Sci. USA*, 95:1556-1561 (1998).

Gorecki, "Prospects and Problems of Gene Therapy: An Update," *Exp. Opin. Emerging Drugs*, 6(2):187-198 (2001).

Green et al., "Adenoviral Vectors: Systemic Delivery and Tumor Targeting," *Cancer Gene Therapy*, 9:1036-1042 (2002).

Ha et al., "Single-Molecule Fluorescence Specetroscopy of Enzyme Conformational Dynamics and Cleavage Mechanism," *Proc. Natl. Acad. Sci. USA*, 96:893-898 (1999).

Haupts et al., "Dynamics of Fluorescence Fluctuations in Green Fluorescent Protein Observed by Fluorescence Correlation Spectroscopy," *Proc. Natl. Acad. Sci. USA*, 95:13573-13578 (1998).

Keay et al., "Autoclavable Low Cost Serum-Free Cell Culture Media: The Growth of Established Cell Lines and Production of Viruses," *Biotechnology and Bioengineering*, 18:363-382 (1976).

Koltermann et al.,"Rapid Assay Processing by Integration of Dual-Color Fluorescence Cross-Correlation Spectroscopy: High Throughput Screening for Enzyme Activity," *Proc. Natl. Acad. Sci. USA*, 95:1421-1426 (1998).

Kozak et al., "Transmissible Spongiform Encephalopathies (TSE): Minimizing the Risk of Transmission of Biological/Biopharmaceutical Products: An Industry Perspective," *Developments in Biological Standardization*, 88:257-264 (1996).

Lippitz et al., "Two-Photon Excitation Microscopy of Tryptophan-containing Proteins," *Proc. Natl. Acad. Sci USA*, 99(5):2772-2777 (2002).

Lu et al., "Single-Molecule Enzymatic Dynamics," *Science*, 282:1877-1882 (1998).

Maiti et al., "Measuring Serotonin Distribution in Live Cells with Three-Photon Excitation," *Science*, 275:530-532 (1997).

Mets et al., "Submillisecond Detection of Single Rhodamine Molecules in Water," *J. Fluoresc.*, 4:259-264 (1994).

Neuhauser et al., "Correlation Between Fluorescence Intermittency and Spectral Diffusion in Single Semiconductor Quantum Dots," *Phys. Rev. Lett.*, 85:3301-3304 (2000).

Nguyen et al., "Detection of Single Molecules of Phycoerythrin in Hydrodynamically Focused Flows by Laser-Induced Fluorescence," *Anal. Chem.*, 59:2158-2161 (1987).

Nie et al., "Probing Individual Molecules with Confocal Fluorescence Microscopy," *Science*, 266:1018-1021 (1994).

Novagen & Calbiochem., Sample Preparation Tools for Protein Research, 2nd Edition, 54-110 (2006).

Peck et al., "Single-Molecule Fluorescence Detection: Autocorrelation Criterion and Experimental.Realization with Phycoerythrin," *Proc. Natl. Acad. Sci.*, 86:4087-4091 (1989).

Peltekian et al., "Adenovirus-Mediated Gene Transfer to the Brain: Methodological Assessment," *J. Neurosci. Meths.*, 71:77-84 (1997).

Reshetnyak et al., "Decomposition of Protein Tryptophan Fluorescence Spectra Into Log-Normal Components. II. The Statistical Proof of Discreteness of Tryptophan Classes in Proteins," *Biophysical J.*, 81:1710-1734 (2001).

Sastry et al., "Evaluation of Plasmid DNA Removal from Lentiviral Vectors by Benzonase Treatmetn," *Human Gene Therapy*, 15:221-226 (2004).

Schwille et al., "Molecular Dynamics in Living Cells Observed by Fluorescence Correlation Spectroscopy with One- and Two-Photon Excitation," *Biophy. J.*, 77:2251-2265 (1999).

Sonnleitner et al., "Imaging Individual Molecules by Two-Photon Exciation," *Chem. Phys. Lett.*, 300:221-226 (1999).

Tanaka et al., "Simple fluorescent enzyme immunoassay for detection and quantification of hepatitis C viremia," *J. of Hepatology*, 23: 742-745 (1995).

Verma et al., "Gene Therapy—Promises, Problems and Prospects," *Nature*, 389:239-242 (1997).

Wennmalm et al., "Conformational Fluctuations in Single DNA Molecules," *Proc. Natl. Acad. Sci. USA*,94:10641-10646 (1997).

Wennmalm et al., "UV-Fluorescence Correlation Spectroscopy of 2-Aminopurine," *Biol. Chem.*, 382:393-397 (2001).

www.sterlitech.com/generalfaq.htm.

Yu et al., "Unmasking Electronic Energy Transfer of Conjugated Polymers of Suppression of O2 Quenching," *Science*, 289:1327-1330 (2000).

Green et al., Human adenoviruses: growth, purification, and transfection assay, Meth. Enzymol., 58:425-435, 1979.

Kotani, Serum-free production of adenoviral vectors for gene therapy, Williamsburg BioProcessing Conference, Nov. 18-21, 1996.

Office Action, U.S. Appl. No. 08/975,519, United States Patent and Trademark Office, mailed Jun. 24, 1999.

Office Action, U.S. Appl. No. 08/975,519, United States Patent and Trademark Office, mailed Sep. 25, 1998.

Office Action, U.S. Appl. No. 09/203,078, United States Patent and Trademark Office, mailed Mar. 20, 2001.

Office Action, U.S. Appl. No. 09/203,078, United States Patent and Trademark Office, mailed Sep. 13, 2001.

Office Action, U.S. Appl. No. 09/203,078, United States Patent and Trademark Office, mailed Oct. 3, 2003.

Office Action, U.S. Appl. No. 09/203,078, United States Patent and Trademark Office, mailed Nov. 17, 2004.

Office Action, U.S. Appl. No. 09/556,570, United States Patent and Trademark Office, mailed Feb. 24, 2003.

Office Action, U.S. Appl. No. 09/556,570, United States Patent and Trademark Office, mailed Apr. 23, 2002.

Office Action, U.S. Appl. No. 09/556,570, United States Patent and Trademark Office, mailed Jun. 29, 2001.

Office Action, U.S. Appl. No. 10/033,491, United States Patent and Trademark Office, mailed Aug. 23, 2007.

Office Action, U.S. Appl. No. 10/033,491, United States Patent and Trademark Office, mailed Jul. 1, 2004.

Office Action, U.S. Appl. No. 10/033,491, United States Patent and Trademark Office, mailed Oct. 6, 2004.

Office Action, U.S. Appl. No. 10/033,491, United States Patent and Trademark Office, mailed Jul. 13, 2005.

Office Action, U.S. Appl. No. 10/033,491, United States Patent and Trademark Office, mailed Dec. 16, 2005.

Office Action, U.S. Appl. No. 10/033,491, United States Patent and Trademark Office, mailed May 18, 2006.

Office Action, U.S. Appl. No. 10/033,491, United States Patent and Trademark Office, mailed Aug. 8, 2006.

Office Action, U.S. Appl. No. 10/033,571, United States Patent and Trademark Office, mailed Mar. 16, 2007.

Office Action, U.S. Appl. No. 10/033,571, United States Patent and Trademark Office, mailed Jun. 22, 2004.

Office Action, U.S. Appl. No. 10/033,571, United States Patent and Trademark Office, mailed Oct. 21, 2004.

Office Action, U.S. Appl. No. 10/033,571, United States Patent and Trademark Office, mailed Jul. 11, 2005.

Office Action, U.S. Appl. No. 10/033,571, United States Patent and Trademark Office, mailed May 2, 2006.

Rowe et al., Complementation of adenovirus type 5 host range mutants by adenovirus type 12 in coinfected HeLa and BHK-21 cells, J. Virol., 38:191-197, 1994.

Wills et al., Development and characterization of recombinant adenoviruses encoding human p53 for gene therapy of cancer, Hum. Gene Ther., 5:1079-1088, 1994.

Communication pursuant to Article 96(2) EPC, EP 06012869.1, European Patent Office, Jun. 15, 2007.

Communication pursuant to Article 96(2) EPC, EP 06025694.8, European Patent Office, Jun. 14, 2007.

Green et al., Biochemical studies on adenovirus multiplication: kinetics of nucleic acid and protein synthesis in suspension cultures, Virology, 13:169-176, 1961.

Griffiths, Scaling up of animal cell cultures, Animal Cell Cultures: A Practical Approach, 2nd edition, edited by Freshney, 3:47-93, 1992.

Kawakubo et al., Tissue plasminogen activator (t-PA) production by a high density culture of weakly adherent human embryonic kidney cells using a polyurethane-foam packed-bed culture system, Appl. Microbiol. Biotechnol., 41:413-418, 1994.

Mann et al., 3rd General Meeting of ESACT, Oxford, Develop. Biol. Standard, 46:289-294, 1980.

Notice of Opposition to a European Patent, EP 0968284, European Patent Office, Sep. 12, 2007.

Wang et al., Studies on high-density cultivation of Vero cells with biosilon solid microcarrier, Chinese J. Biotechnol., 12:119-129, 1996.

Declaration under 37 C.F.R. § 1.132 of Dr. Peter Clarke with Exhibits 1-5, dated Oct. 26, 2007.

Declaration under 37 C.F.R. § 1.132 of Dr. Shuyuan Zhang with attached Exhibits, dated Oct. 29, 2007.

Office Action, U.S. Appl. No. 10/033,571, United States Patent and Trademark Office, mailed Feb. 5, 2008.

Office Action, U.S. Appl. No. 10/033,571, United States Patent and Trademark Office, mailed Feb. 22, 2008.

* cited by examiner

← DEFECTIVE VIRUS BAND (TITER: $3\times10^7$ PFU/ml)

← INTACT VIRUS BAND (TITER: $1\times10^{11}$ PFU/ml)

|  | TITER (PFU/ML) | VOL.(ml) | YEILD (PFU) | RECOVERY (%) | |
|---|---|---|---|---|---|
|  |  |  |  | STEP | ACC. |
| CUBE (LOW PERFUSION RATE KEEP GLUCOSE>1g/L) |  |  |  |  |  |
| ↓ 1% TWEEN-20-BUFFER A |  |  |  |  |  |
| HARVEST |  |  |  |  |  |
| ↓ CLARIFICATION AND FILTRATION (0.22μm) |  |  |  |  |  |
|  | $2.6 \times 10^9$ | 1900 | $4.9 \times 10^{12}$ |  |  |
| VIRUS SOLUTION |  |  |  |  |  |
| ↓ CONC./DIAF. (10-FOLD CONC., DIAF INTO 1M NaCl BUFFER A |  |  |  |  |  |
|  | $2.5 \times 10^{10}$ | 200 | $5 \times 10^{12}$ | 102% |  |
| CONC. SUP |  |  |  |  |  |
| ↓ BENZONASE TREATMENT (O/N, RT, 100μ/ml) |  |  |  |  |  |
| TREATED SUP |  |  |  |  |  |
| ↓ DILUTED WITH WATER TO CONDUCTIVITY= 22-25 mS/cm | $7 \times 10^9$ | 700 | $4.9 \times 10^{12}$ | 98% | 100% |
| DILUTED VIRUS SOLUTION |  |  |  |  |  |
| ↓ |  |  |  |  |  |
|  | $1.5 \times 10^{10}$ | 240 | $3.6 \times 10^{12}$ | 73% | 73% |
| PURIFIED VIRUS |  |  |  |  |  |
| ↓ CONC./DIAF (5-FOLD CONC) |  |  |  |  |  |
|  | $7 \times 10^{10}$ | 50 | $3.5 \times 10^{12}$ | 97% | 71% |
| FINAL PURIFIED PRODUCT |  |  |  |  |  |

FIG.23

METHOD FOR THE PRODUCTION AND PURIFICATION OF ADENOVIRAL VECTORS

The present application is a divisional of U.S. application Ser. No. 10/033,571, filed Dec. 27, 2001, which is a continuation of U.S. application Ser. No. 09/556,570, filed Apr. 24, 2000, now U.S. Pat. No. 6,726,907, which is a continuation of U.S. application Ser. No. 08/975,519, filed Nov. 20, 1997, now U.S. Pat. No. 6,194,191, which claims benefit of U.S. provisional application Ser. No. 60/031,329, filed Nov. 20, 1996. The entire text of the above-referenced disclosures are specifically incorporated by reference herein without disclaimer.

BACKGROUND OF THE INVENTION

1. Field of the Invention

The present invention relates generally to the fields of cell culture and virus production. More particularly, it concerns improved methods for the culturing of mammalian cells, infection of those cells with adenovirus and the production of infectious adenovirus particles therefrom.

2. Description of Related Art

Adenoviral vectors, which express therapeutic proteins, are currently being evaluated in the clinic for the treatment of a variety of cancer indications, including lung and head and neck cancers. As the clinical trials progress, the demand for clinical grade adenoviral vectors is increasing dramatically. The projected annual demand for a 300 patient clinical trial could reach approximately $6 \times 10^{14}$ PFU.

Traditionally, adenoviruses are produced in commercially available tissue culture flasks or "cellfactories." Virus infected cells are harvested and freeze-thawed to release the viruses from the cells in the form of crude cell lysate. The produced crude cell lysate (CCL) is then purified by double CsCl gradient ultracentrifugation. The typically reported virus yield from 100 single tray cellfactories is about $6 \times 10^{12}$ PFU. Clearly, it becomes unfeasible to produce the required amount of virus using this traditional process. New scaleable and validatable production and purification processes have to be developed to meet the increasing demand.

The purification throughput of CsCl gradient ultracentrifugation is so limited that it cannot meet the demand for adenoviral vectors for gene therapy applications. Therefore, in order to achieve large scale adenoviral vector production, purification methods other than CsCl gradient ultracentrifugation have to be developed. Reports on the chromatographic purification of viruses are very limited, despite the wide application of chromatography for the purification of recombinant proteins. Size exclusion, ion exchange and affinity chromatography have been evaluated for the purification of retroviruses, tick-borne encephalitis virus, and plant viruses with varying degrees of success (Crooks, et al., 1990; Aboud, et al, 1982; McGrath et al., 1978, Smith and Lee, 1978; O'Neil and Balkovic, 1993). Even less research has been done on the chromatographic purification of adenovirus. This lack of research activity may be partially attributable to the existence of the effective, albeit non-scalable, CsCl gradient ultracentrifugation purification method for adenoviruses.

Recently, Huyghe et al. (1996) reported adenoviral vector purification using ion exchange chromatography in conjunction with metal chelate affinity chromatography. Virus purity similar to that from CsCl gradient ultracentrifugation was reported. Unfortunately, only 23% of virus was recovered after the double column purification process. Process factors that contribute to this low virus recovery are the freeze/thaw step utilized by the authors to lyse cells in order to release the virus from the cells and the two column purification procedure.

Clearly, there is a demand for an effective and scaleable method of adenoviral vector production that will recover a high yield of product to meet the ever increasing demand for such products.

SUMMARY OF THE INVENTION

The present invention describes a new process for the production and purification of adenovirus. This new production process offers not only scalability and validatability but also virus purity comparable to that achieved using CsCl gradient ultracentrifugation.

Thus the present invention provides a method for producing an adenovirus comprising growing host cells in media at a low perfusion rate, infecting the host cells with an adenovirus, harvesting and lysing the host cells to produce a crude cell lysate, concentrating the crude cell lysate, exchanging buffer of crude cell lysate, and reducing the concentration of contaminating nucleic acids in the crude cell lysate.

In particular embodiments, the method further comprises isolating an adenoviral particle from the lysate using chromatography. In certain embodiments, the isolating consists essentially of a single chromatography step. In other embodiments, the chromatography step is ion exchange chromatography. In particularly preferred embodiments, the ion exchange chromatography is carried out at a pH range of between about 7.0 and about 10.0. In more preferred embodiments, the ion exchange chromatography is anion exchange chromatography. In certain embodiments the anion exchange chromatography utilizes DEAE, TMAE, QAE, or PEI. In other preferred embodiments, the anion exchange chromatography utilizes Toyopearl Super Q 650M, MonoQ, Source Q or Fractogel TMAE.

In certain embodiments of the present invention the glucose concentration in the media is maintained between about 0.7 and about 1.7 g/L. In certain other embodiments, the exchanging buffer involves a diafiltration step.

In preferred embodiments of the present invention, the adenovirus comprises an adenoviral vector encoding an exogenous gene construct. In certain such embodiments, the gene construct is operatively linked to a promoter. In particular embodiments, the promoter is SV40 IE, RSV LTR, β-actin or CMV IF adenovirus major late, polyoma F9-1, or tyrosinase. In particular embodiments of the present invention, the adenovirus is a replication-incompetent adenovirus. In other embodiments, the adenovirus is lacking at least a portion of the E1-region. In certain aspects, the adenovirus is lacking at least a portion of the E1A and/or E1B region. In other embodiments, the host cells are capable of complementing replication. In particularly preferred embodiments, the host cells are 293 cells.

In preferred a embodiment of the present invention it is contemplated that the exogenous gene construct encodes a therapeutic gene. For example, the therapeutic gene may encode antisense ras, antisense myc, antisense raf, antisense erb, antisense src, antisense fms, antisense jun, antisense trk, antisense ret, antisense gsp, antisense hst, antisense bcl antisense abl, Rb, CFTR, p16, p21, p27, p57, p73; C-CAM, APC, CTS-1, zac1, scFV ras, DCC, NF-1, NF-2, WT-1, MEN-I, MEN-II, BRCA1 VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF G-CSF, thymidine kinase or p53.

In certain aspects of the present invention, the cells may be harvested and lysed ex situ using a hypotonic solution, hypertonic solution, freeze-thaw, sonication, impinging jet, microfluidization or a detergent. In other aspects, the cells are harvested and lysed in situ using a hypotonic solution, hypertonic solution, or a detergent. As used herein the term "in situ" refers to the cells being located within the tissue culture apparatus for example CellCube™ and "ex situ" refers to the cells being removed from the tissue culture apparatus.

In particular embodiments, the cells are lysed and harvested using detergent. In preferred embodiments the detergent may be Thesit®, NP-40®, Tween-20®, Brij-58®, Triton X®-100 or octyl glucoside. In other aspects of the present invention lysis is achieved through autolysis of infected cells. In certain other aspects of the present invention the cell lysate is treated with Benzonase®, or Pulmozyme®.

In particular embodiments, the method further comprises a concentration step employing membrane filtration. In particular embodiments, the filtration is tangential flow filtration. In preferred embodiments, the filtration may utilize a 100 to 300K NMWC, regenerated cellulose, or polyether sulfone membrane.

The present invention also provides an adenovirus produced according to a process comprising the steps of growing host cells in media at a low perfusion rate, infecting the host cells with an adenovirus, harvesting and lysing the host cells to produce a crude cell lysate, concentrating the crude cell lysate, exchanging buffer of crude cell lysate, and reducing the concentration of contaminating nucleic acids in the crude cell lysate.

Other aspects of the present invention provide a method for the purification of an adenovirus comprising growing host cells, infecting the host cells with an adenovirus harvesting and lysing the host cells by contacting the cells with a detergent to produce a crude cell lysate, concentrating the crude cell lysate, exchanging buffer of crude cell lysate, and reducing the concentration of contaminating nucleic acids in the crude cell lysate.

In particular embodiments, the detergent may be Thesit®, NP-40®, Tween-20®, Brij-58®, Triton X-100® or octyl glucoside. In more particular embodiments the detergent is present in the lysis solution at a concentration of about 1% (w/v).

In other aspects of the present invention there is provided an adenovirus produced according to a process comprising the steps of growing host cells, infecting the host cells with an adenovirus, harvesting and lysing the host cells by contacting the cells with a detergent to produce a crude cell lysate, concentrating the crude cell lysate, exchanging buffer of crude cell lysate, and reducing the concentration of contaminating nucleic acids in the crude cell lysate.

In yet another embodiment, the present invention provides a method for the purification of an adenovirus comprising the steps of growing host cells in serum-free media; infecting said host cells with an adenovirus; harvesting and lysing said host cells to produce a crude cell lysate; concentrating said crude cell lysate; exchanging buffer of crude cell lysate; and reducing the concentration of contaminating nucleic acids in said crude cell lysate. In preferred embodiments, the cells may be grown independently as a cell suspension culture or as an anchorage-dependent culture.

In particular embodiments, the host cells are adapted for growth in serum-free media. In more preferred embodiments, the adaptation for growth in serum-free media comprises a sequential decrease in the fetal bovine serum content of the growth media. More particularly, the serum-free media comprises a fetal bovine serum content of less than 0.03% v/v.

In other embodiments, the method further comprises isolating an adenoviral particle from said lysate using chromatography. In preferred embodiments, the isolating consists essentially of a single chromatography step. More particularly, the chromatography step is ion exchange chromatography.

Also contemplated by the present invention is an adenovirus produced according to a process comprising the steps of growing host cells in serum-free media; infecting said host cells with an adenovirus; harvesting and lysing said host cells to produce a crude cell lysate; concentrating said crude cell lysate; exchanging buffer of crude cell lysate; and reducing the concentration of contaminating nucleic acids in said crude cell lysate.

The present invention further provides a 293 host cell adapted for growth in serum-free media. In certain aspects, the adaptation for growth in serum-free media comprises a sequential decrease in the fetal bovine serum content of the growth media. In particular embodiments, the cell is adapted for growth in suspension culture. In particular embodiments, the cells of the present invention are designated IT293SF cells. These cells were deposited with the American Tissue Culture Collection (ATCC) in order to meet the requirements of the Budapest Treaty on the international recognition of deposits of microorganisms for the purposes of patent procedure. The cells were deposited by Dr. Shuyuan Zhang on behalf of Introgen Therapeutics, Inc. (Houston, Tex.), on Nov. 17, 1997. IT293SF cell line is derived from an adaptation of 293 cell line into serum free suspension culture as described herein. The cells may be cultured in IS 293 serum-free media (Irvine Scientific. Santa Ana, Calif.) supplemented with 100 mg/L heparin and 0.1% pluronic F-68, and are permissive to human adenovirus infection.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A Thesit®. FIG. 3B Triton®X-100. FIG. 3C. NP-40®. FIG. 3D. Brij®80. FIG. 3E. Tween®20. Detergent concentration: 1% (w/v) lysis temperature: room temperature. (solid line $A_{260}$; dotted line $A_{280}$).

FIG. 8B fraction 4, FIG. 8C fraction 8. (solid line $A_{260}$; dotted line $A_{280}$).

FIG. 10A Crude virus solution. FIG. 10B Flow through. FIG. 10C. Peak number 1. FIG. 10D. Peak number 2. FIG. 10E. CsCl purified virus. (solid line $A_{260}$; dotted line $A_{280}$).

FIG. 16A HPLC profiles of virus fraction from first purification step. FIG. 16B HPLC profiles of virus fraction from second purification (solid line $A_{260}$; dotted line $A_{280}$).

FIG. 19A SDS-PAGE analysis. FIG. 19B Western blot for BSA. FIG. 19C nucleic acid slot blot to determine the contaminating nucleic acid concentration.

FIG. 20A, FIG. 20B, FIG. 20C, FIG. 20D, FIG. 20E and FIG. 20F. Capacity study of the Toyopearl SuperQ 650M resin. FIG. 20A Flow through from loading ratio of 1:1. FIG. 20B. Purified virus from loading ratio of 1:1. FIG. 20C Flow through of loading ratio of 2:1. FIG. 20D. Purified virus from the loading ratio of 2:1. FIG. 20E Flow through from loading ratio of 3:1. FIG. 20F. Purified virus from the loading ratio of 3:1. (solid line $A_{260}$; dotted line $A_{280}$).

FIG. 23. A production and purification flow chart for AdCMVp53.

DESCRIPTION OF ILLUSTRATIVE EMBODIMENTS

Figure 1A:
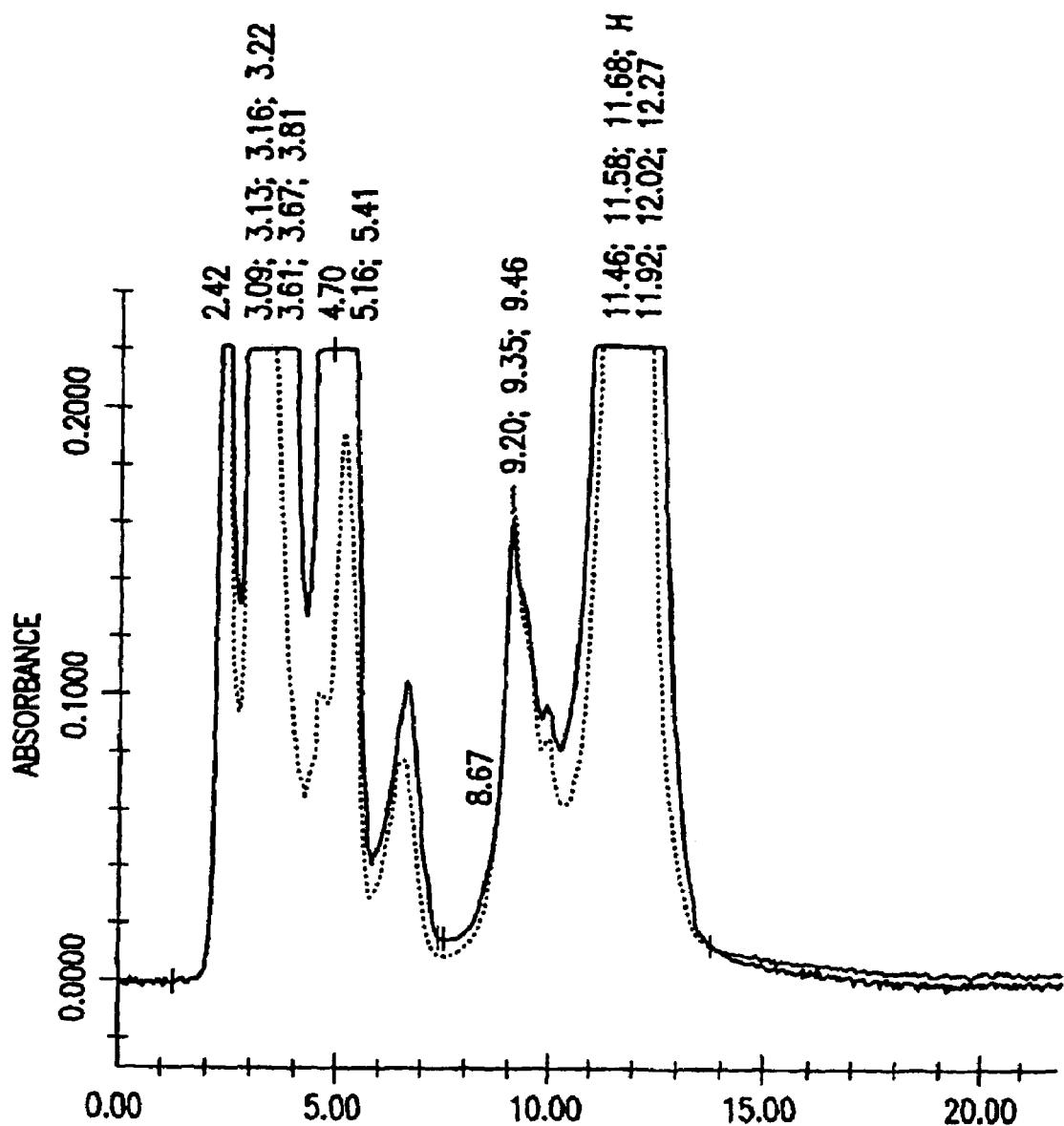
FIG. 1A and FIG. 1B. HPLC profiles of the viral solutions from production runs using medium perfusion rates characterized as "high" (FIG. 1A) and "low" (FIG. 1B).

It has been shown that adenoviral vectors can successfully be used in eukaryotic gene expression and vaccine development. Recently, animal studies have demonstrated that recombinant adenovirus could be used for gene therapy. Successful studies in administering recombinant adenovirus to different tissues have proven the effectiveness of adenoviral vectors in therapy. This success has led to the use of such vectors in human clinical trials. There now is an increased demand for the production of adenoviral vectors to be used in various therapies. The techniques currently available are insufficient to meet such a demand. The present invention provides methods for the production of large amounts of adenovirus for use in such therapies.

The present invention involves a process that has been developed for the production and purification of a replication deficient recombinant adenovirus. The production process is based on the use of a Cellcube™ bioreactor for cell growth and virus production. It was found that a given perfusion rate, used during cell growth and the virus production phases of culturing, has a significant effect on the downstream purification of the virus. More specifically, a low to medium perfusion rate improves virus production. In addition, lysis solution composed of buffered detergent, used to lyse cells in the Cellcube™ at the end of virus production phase, also improves the process. With these two advantages, the harvested crude virus solution can be purified using a single ion exchange chromatography run, after concentration/diafiltration and nuclease treatment to reduce the contaminating nucleic acid concentration in the crude virus solution. The column purified virus has equivalent purity relative to that of double CsCl gradient purified virus. The total process recovery of the virus product is 70±10%. This is a significant improvement over the results reported by Huyghe et at. (1996). Compared to double CsCl gradient ultracentrifugation, column purification has the advantage of being more consistent, scaleable, validatable, faster and less expensive. This new process represents a significant improvement in the technology for manufacturing of adenoviral vectors for gene therapy.

Therefore, the present invention is designed to take advantage of these improvements in large scale culturing systems and purification for the purpose of producing and purifying adenoviral vectors. The various components for such a system, and methods of producing adenovirus therewith, are set forth in detail below.

1. Host Cells
   A) Cells

In a preferred embodiment, the generation and propagation of the adenoviral vectors depend on a unique helper cell line, designated 293, which was transformed from human embryonic kidney cells by Adenovirus serotype 5 (Ad5) DNA fragments and constitutively expresses E1 proteins (Graham et al., 1977). Since the E3 region is dispensable from the Ad genome (Jones and Shenk, 1978), the current Ad vectors, with the help of 293 cells, carry foreign DNA in either the E1, the E3 or both regions (Graham and Prevec, 1991; Bett et al., 1994).

A first aspect of the present invention is the recombinant cell lines which express part of the adenoviral genome. These cells lines are capable of supporting replication of adenovirus recombinant vectors and helper viruses having defects in certain adenoviral genes, i.e., are "permissive" for growth of these viruses and vectors. The recombinant cell also is referred to as a helper cell because of the ability to complement defects in, and support replication of, replication-incompetent adenoviral vectors. The prototype for an adenoviral helper cell is the 293 cell line, which contains the adenoviral E1 region. 293 cells support the replication of adenoviral vectors lacking E1 functions by providing in trans the E1-active elements necessary for replication.

Helper cells according to the present invention are derived from a mammalian cell and, preferably, from a primate cell such as human embryonic kidney cell. Although various primate cells are preferred and human or even human embryonic kidney cells are most preferred any type of cell that is capable of supporting replication of the virus would be acceptable in the practice of the invention. Other cell types might include, but are not limited to Vero cells, CHO cells or any eukaryotic cells for which tissue culture techniques are established as long as the cells are adenovirus permissive. The term "adenovirus permissive" means that the adenovirus or adenoviral, vector is able to complete the entire intracellular virus life cycle within the cellular environment.

The helper cell may be derived from an existing cell line, e.g., from a 293 cell line, or developed de novo. Such helper cells express the adenoviral genes necessary to complement in trans deletions in an adenoviral genome or which supports replication of an otherwise defective adenoviral vector, such as the E1, E2, E4, E5 and late functions. A particular portion of the adenovirus genome, the E1 region, has already been used to generate complementing cell lines. Whether integrated or episomal, portions of the adenovirus genome lacking a viral origin of replication, when introduced into a cell line, will not replicate even when the cell is superinfected with wild-type adenovirus. In addition, because the transcription of the major late unit is after viral DNA replication, the late functions of adenovirus cannot be expressed sufficiently from a cell line. Thus, the E2 regions, which overlap with late functions (L1-5), will be provided by helper viruses and not by the cell line. Typically, a cell line according to the present invention will express E1 and/or E4.

As used herein, the term "recombinant" cell is intended to refer to a cell into which a gene, such as a gene from the adenoviral genome, or from another cell, has been introduced. Therefore, recombinant cells are distinguishable from naturally-occurring cells which do not contain a recombinantly-introduced gene. Recombinant cells are thus cells having a gene or genes introduced through "the hand of man."

Replication is determined by contacting a layer of uninfected cells, or cells infected with one or more helper viruses, with virus particles, followed by incubation of the cells. The formation of viral plaques, or cell free areas in the cell layer, is the result of cell lysis caused by the expression of certain viral products. Cell lysis is indicative of viral replication.

Examples of other useful mammalian cell lines that may be used with a replication competent virus or converted into complementing host cells for use with replication deficient virus are Vero and HeLa cells and cell lines of Chinese hamster ovary, W138, BHK, COS-7, HepG2, 3T3, RIN and MDCK cells.

B) Growth in Selection Media

In certain embodiments, it may be useful to employ selection systems that preclude growth of undesirable cells. This may be accomplished by virtue of permanently transforming a cell line with a selectable marker or by transducing or infecting a cell line with a viral vector that encodes a selectable marker. In either situation, culture of the transformed/transduced cell with an appropriate drug or selective compound will result in the enhancement, in the cell population, of those cells carrying the marker.

Examples of markers include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; and hygro, that confers resistance to hygromycin.

C. Growth in Serum Weaning

Serum weaning adaptation of anchorage-dependent cells into serum-fee suspension cultures have been used for the production of recombinant proteins (Berg, 1993) and viral vaccines (Perrin, 1995). There have been few reports on the adaptation of 293A cells into serum-free suspension cultures until recently. Gilbert reported the adaptation of 293A cells into serum-free suspension cultures for adenovirus and recombinant protein production (Gilbert, 1996). Similar adaptation method had been used for the adaptation of A549 cells into serum-free suspension culture for adenovirus production (Morris et al., 1996). Cell-specific virus yields in the adapted suspension cells, however, are about 5-10-fold lower than those achieved in the parental attached cells.

Using the similar serum weaning procedure, the inventors have successfully adapted the 293A cells into serum-free suspension culture (293SF cells). In this procedure, the 293 cells were adapted to a commercially available 293 media by sequentially lowering down the FBS concentration in T-flasks. Briefly, the initial serum concentration in the media was approximately 10% FBS DMEM media in T-75 flask and the cells were adapted to serum-free IS 293 media in T-flasks by lowering down the FBS concentration in the media sequentially. After 6 passages in T-75 flasks the FBS % was estimated to be about 0.0190% and the 293 cells. The cells were subcultured two more times in the T flasks before they were transferred to spinner flasks. The results described herein below show that cells grow satisfactorily in the serum-free medium (IS293 medium, Irvine Scientific, Santa Ana, Calif.). Average doubling time of the cells were 18-24 h achieving stationary cell concentrations in the order of 4-10× $10^6$ cells/ml without medium exchange.

D. Adaptation of Cells for Suspension Culture

Two methodologies have been used to adapt 293, cells into suspension cultures. Graham adapted 293A cells into suspension culture (293N3S cells) by 3 serial passages in nude mice (Graham, 1987). The suspension 293N3S cells were found to be capable of supporting E1 adenoviral vectors. However, Gamier et al. (1994) observed that the 293N35 cells had a relatively long initial lag phase in suspension, a low growth rate, and a strong tendency to clump.

The second method that has been used is a gradual adaptation of 293A cells into suspension growth (Cold Spring Harbor Laboratories, 293S cells). Garnier et al. (1994) reported the use of 293S cells for production of recombinant proteins from adenoviral vectors. The authors found that 293S cells were much less clumpy in calcium-free media and a fresh medium exchange at the time of virus infection could significantly increase the protein production it was found that glucose was the limiting factor in culture without medium exchange.

In the present invention, the 293 cells adapted for growth in serum-flee conditions were adapted into a suspension culture. The cells were transferred in a serum-free 250 mL spinner suspension culture (100 mL working volume) for the suspension culture at an initial cell density of between about 1.18E+5 vc/mL and about 5.22E+5 vc/mL. The media may be supplemented with heparin to prevent aggregation of cells. This cell culture systems allows for some increase of cell density whilst cell viability is maintained. Once these cells are growing in culture, they cells are subcultured in the spinner flasks approximately 7 more passages. It may be noted that the doubling time of the cells is progressively reduced until at the end of the successive passages the doubling time is about 1.3 day, i.e. comparable to 1.2 day of the cells in 10% A FBS media in the attached cell culture. In the serum-free IS 293 media supplemented with heparin almost all the cells existed as individual cells not forming aggregates of cells in the suspension culture.

2. Cell Culture Systems

The ability to produce infectious viral vectors is increasingly important to the pharmaceutical industry, especially in the context of gene therapy. Over the last decade, advances in biotechnology have led to the production of a number of important viral vectors that have potential uses as therapies, vaccines and protein production machines. The use of viral vectors in mammalian cultures has advantages over proteins produced in bacterial or other lower lifeform hosts in their ability to post-translationally process complex protein structures such as disulfide-dependent folding and glycosylation.

Development of cell culture for production of virus vectors has been greatly aided by the development in molecular biology of techniques for design and construction of vector systems highly efficient in mammalian cell cultures, a battery of useful selection markers, gene amplification schemes and a more comprehensive understanding of the biochemical and cellular mechanisms involved in procuring the final biologically-active molecule from the introduced vector.

Frequently, factors which affect the downstream (in this case, beyond the cell lysis) side of manufacturing scale-up were not considered before selecting the cell line as the host for the expression system. Also, development of bioreactor systems capable of sustaining very high density cultures for prolonged periods of time have not lived up to the increasing demand for increased production at lower costs.

The present invention will take advantage of the recently available bioreactor technology. Growing cells according to the present invention in a bioreactor allows for large scale production of fully biologically-active cells capable of being infected by the adenoviral vectors of the present invention. By operating the system at a low perfusion rate and applying a different scheme for purification of the infecting particles, the invention provides a purification strategy that is easily scale-able to produce large quantities of highly purified product.

Bioreactors have been widely used for the production of biological products from both suspension and anchorage dependent animal cell cultures. The most widely used producer cells for adenoviral vector production are anchorage dependent human embryonic kidney cells (293 cells). Bioreactors to be developed for adenoviral vector production should have the characteristic of high volume-specific culture surface area in order to achieve high producer cell density and high virus yield. Microcarrier cell culture in stirred tank bioreactor provides very high volume-specific culture surface area and has been used for the production of viral vaccines (Griffiths, 1986). Furthermore, stirred tank bioreactors have industrially been proven to be scaleable. The multiplate Cellcube™ cell culture system manufactured by Corning-Costar also offers a very high volume-specific culture surface area Cells grow on both sides of the culture plates hermetically sealed together in the shape of a compact cube. Unlike stirred tank bioreactors, the Cellcube™ culture unit is disposable. This is very desirable at the early stage production of clinical product because of the reduced capital expenditure, quality control and quality assurance costs associated with disposable systems. In consideration of the advantages offered by the different systems, both the stirred tank bioreactor and the Cellcube™ system were evaluated for the production of adenovirus.

A) Anchorage-dependent Versus Non-anchorage-dependent Cultures.

Animal and human cells can be propagated in vitro in two modes: as non-anchorage dependent cells growing freely in suspension throughout the bulk of the culture; or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. Large scale suspension culture based on microbial (bacterial and yeast) fermentation technology has clear advantages for the manufacturing of mammalian cell products. The processes are relatively simple to operate and straightforward to scale up. Homogeneous conditions can be provided in the reactor which allows for precise monitoring and control of temperature, dissolved oxygen, and pH, and ensure that representative samples of the culture can be taken.

However, suspension cultured cells cannot always be used in the production of biologicals. Suspension cultures are still considered to have tumorigenic potential and thus their use as substrates for production put limits on the use of the resulting products in human and veterinary applications (Petricciani, 1985; Larsson, 1987). Viruses propagated in suspension cultures as opposed to anchorage-dependent cultures can sometimes cause rapid changes in viral markers, leading to reduced immunogenicity (Bahnemann, 1980). Finally, sometimes even recombinant cell lines can secrete considerably higher amounts of products when propagated as anchorage-dependent cultures as compared with the same cell line in suspension (Nilsson and Mosbach, 1987). For these reasons, different types of anchorage-dependent cells are used extensively in the production of different biological products.

B) Reactors and Processes for Suspension.

Large scale suspension culture of mammalian cultures in stirred tanks was undertaken. The instrumentation and controls for bioreactors adapted, along with the design of the fermentors, from related microbial applications. However, acknowledging the increased demand for contamination control in the slower growing mammalian cultures, improved aseptic designs were quickly implemented, improving dependability of these reactors. Instrumentation and controls are basically the same as found in other fermentors and include agitation, temperature, dissolved oxygen, and pH controls. More advanced probes and autoanalyzers for on-line and off-line measurements of turbidity (a function of particles present), capacitance (a function of viable cells present), glucose/lactate, carbonate/bicarbonate and carbon dioxide are available. Maximum cell densities obtainable in suspension cultures are relatively low at about $2-4\times10^6$ cells/ml of medium (which is less than 1 mg dry cell weight per ml), well below the numbers achieved in microbial fermentation.

Two suspension culture reactor designs are most widely used in the industry due to their simplicity and robustness of operation—the stirred reactor and the airlift reactor. The stirred reactor design has successfully been used on a scale of 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical nixing. Typically, the height-to-diameter ratio is 10:1. The airlift reactor scales up relatively easily, has good mass transfer of gasses and generates relatively low shear forces.

Most large-scale suspension cultures are operated as batch or fed-batch processes because they are the most straightforward to operate and scale up. However, continuous processes based on chemostat or perfusion principles are available.

A batch process is a closed system in which typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a fed-batch process is still a closed system because cells, products and waste products are not removed.

In what is still a closed system, perfusion of fresh medium through the culture can be achieved by retaining the cells with a variety of devices (e.g. fine mesh spin filter, hollow fiber or flat plate membrane filters, settling tubes). Spin filter cultures can produce cell densities of approximately $5 \times 10^7$ cells/ml. A true open system and the simplest perfusion process is the chemostat in which there is an inflow of medium and an outflow of cells and products. Culture medium is fed to the reactor at a predetermined and constant rate which maintains the dilution rate of the culture at a value less than the maximum specific growth rate of the cells (to prevent washout of the cell mass from the reactor). Culture fluid containing cells and cell products and byproducts is removed at the same rate.

C) Non-perfused Attachment Systems.

Traditionally, anchorage-dependent cell cultures are propagated on the bottom of small glass or plastic vessels. The restricted surface-to-volume ratio offered by classical and traditional techniques, suitable for the laboratory scale, has created a bottleneck in the production of cells and cell products on a large scale. In an attempt to provide systems that offer large accessible surfaces for cell growth in small culture volume, a number of techniques have been proposed: the roller bottle system, the stack plates propagator, the spiral film bottles, the hollow fiber system, the packed bed, the plate exchanger system, and the membrane tubing reel. Since these systems are non-homogeneous in their nature, and are sometimes based on multiple processes, they suffer from the following shortcomings—limited potential for scale-up, difficulties in taking cell samples, limited potential for measuring and controlling key process parameters and difficulty in maintaining homogeneous environmental conditions throughout the culture.

Despite these drawbacks, a commonly used process for large scale anchorage-dependent cell production is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling. With frequent media changes, roller bottle cultures can achieve cell densities of close to $0.5 \times 10^6$ cells/cm$^2$ (corresponding to approximately $10^9$ cell/bottle or almost $10^7$ cell/ml of culture media).

D) Cultures on Microcarriers

In an effort to overcome the shortcomings of the traditional anchorage-dependent culture processes, van Wezel (1967) developed the concept of the microcarrier culturing systems. In this system, cells are propagated on the surface of small solid particles suspended in the growth medium by slow agitation. Cells attach to the microcarriers and grow gradually to confluency on the microcarrier surface. In fact, this large scale culture system upgrades the attachment dependent culture from a single disc process to a unit process in which both monolayer and suspension culture have been brought together. Thus, combining the necessary surface for a cell to grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products. Cell yields are up to $1-2 \times 10^7$ cells/ml when cultures are propagated in a perfused reactor mode. Second, cells can be propagated in one unit process vessels instead of using many small low-productivity vessels (i.e., flasks or dishes). This results in far better nutrient utilization and a considerable saving of culture medium. Moreover, propagation in a single reactor leads to reduction in need for facility space and in the number of handling steps required per cell, thus reducing labor cost and risk of contamination. Third, the well-mixed and homogeneous microcarrier suspension culture makes it possible to monitor and control environmental conditions (e.g., pH, pO$_2$, and concentration of medium components), thus leading to more reproducible cell propagation and product recovery. Fourth, it is possible to take a representative sample for microscopic observation, chemical testing, or enumeration. Fifth, since microcarriers settle out of suspension quickly, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension E) Microencapsulation of Mammalian Cells One method which has shown to be particularly useful for culturing mammalian cells is microencapsulation. The mammalian cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. Lim (1982, U.S. Pat. No. 4,352,883, incorporated herein by reference,) describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquefied by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150-1500 µm in diameter, are easily retained in a perfused reactor using a fine-meshed screen. The ratio of capsule volume to total media volume can be maintained from as dense as 1:2 to 1:10. With intracapsular cell densities of up to $10^8$, the effective cell density in the culture is $1-5 \times 10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for implantation.

The current invention includes cells which are anchorage-dependent in nature. 293 cells, for example, are anchorage-dependent, and when grown in suspension, the cells will attach to each other and grow in clumps, eventually suffocating cells in the inner core of each clump as they reach a size that leaves the core cells unsustainable by the culture conditions. Therefore, an efficient means of large-scale culture of anchorage-dependent cells is needed in order to effectively employ these cells to generate large quantities of adenovirus.

F) Perfused Attachment Systems

Perfused attachment systems are a preferred form of the present invention. Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential.

The current use of perfused culture is in response to the challenge of growing cells at high densities (i.e., $0.1-5 \times 10^8$ cells/ml). In order to increase densities beyond $2-4 \times 10^6$ cells/ml, the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

The development of a perfused packed-bed reactor using a bed matrix of a non-woven fabric has provided a means for maintaining a perfusion culture at densities exceeding $10^8$ cells/ml of the bed volume (CelliGen™, New Brunswick Scientific, Edison, N J; Wang et al., 1992; Wang et al., 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 µm to 100 µm, providing for a high internal volume with "pore" volumes corresponding to 1 to 20 times the volumes of individual cells.

In comparison to other culturing systems, this approach offers several significant advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and can be produced in low-protein medium which facilitates subsequent purification steps. Also, the unique design of this reactor system offers an easier way to scale up the reactor. Currently, sizes up to 30 liter are available. One hundred liter and 300 liter versions are in development and theoretical calculations support up to a 1000 liter reactor. This technology is explained in detail in WO 94/17178 (Aug. 4, 1994, Freedman et al), which is hereby incorporated by reference in its entirety.

The Cellcube™ (Corning-Costar) module provides a large styrenic surface area for the immobilization and growth of substrate attached cells. It is an integrally encapsulated sterile single-use device that has a series of parallel culture plate joined to create thin sealed laminar flow spaces between adjacent plates.

The Cellcube™ module has inlet and outlet ports that are diagonally opposite each other and help regulate the flow of media. During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Cells within the system reach a higher density of solution (cells/ml) than in traditional culture systems. Many typically used basal media are designed to support $1-2 \times 10^6$ cells/ml/day. A typical Cellcube™, run with an 85,000 $cm^2$ surface, contains approximately 6 L media within the module. The cell density often exceeds $10^7$ cells/mL in the culture vessel. At confluence, 2-4 reactor volumes of media are required per day.

The timing and parameters of the production phase of cultures depends on the type and use of a particular cell line. Many cultures require a different media for production than is required for the growth phase of the culture. The transition from one phase to the other will likely require multiple washing steps in traditional cultures. However, the Cellcube™ system employs a perfusion system. On of the benefits of such a system is the ability to provide a gentle transition between various operating phases. The perfusion system negates the need for traditional wash steps that seek to remove serum components in a growth medium.

In an exemplary embodiment of the present invention, the CellCube™ system is used to grow cells transfected with AdCMVp53. 293 cells were inoculated into the Cellcube™ according to the manufacturer's recommendation. Inoculation cell densities were in the range of $1\text{-}1.5\times10^4/\text{cm}^2$. Cells were allowed to grow for 7 days at 37° C. under culture conditions of pH=7.20, DO=60% air saturation. The medium perfusion rate was regulated according to the glucose concentration in the Cellcube™. One day before viral infection, medium for perfusion was changed from a buffer comprising 10% FBS to a buffer comprising 2% FBS. On day 8, cells were infected with virus at a multiplicity of infection (MOI) of 5. Medium perfusion was stopped for 1 hr immediately after infection then resumed for the remaining period of the virus production phase. Culture was harvested 45-48 hr post-infection. Of course these culture conditions are exemplary and may be varied according to the nutritional needs and growth requirements of a particular cell line. Such variation may be performed without undue experimentation and are well within the skill of the ordinary person in the art.

G) Serum-Free Suspension Culture

In particular embodiments, adenoviral vectors for gene therapy are produced from anchorage-dependent culture of 293 cells (293A cells) as described above. Scale-up of adenoviral vector production is constrained by the anchorage-dependency of 293A cells. To facilitate scale-up and meet future demand for adenoviral vectors, significant efforts have been devoted to the development of alternative production processes that are amenable to scale-up. Methods include growing 293A cells in microcarrier cultures and adaptation of 293A producer cells into suspension cultures. Microcarrier culture techniques have been described above. This technique relies on the attachment of producer cells onto the surfaces of microcarriers which are suspended in culture media by mechanical agitation. The requirement of cell attachment may present some limitations to the scaleability of microcarrier cultures.

Until the present application there have been no reports on the use of 293 suspension cells for adenoviral vector production for gene therapy. Furthermore, the reported suspension 293 cells require the presence of 5-10% FBS in the culture media for optimal cell growth and virus production. Historically, presence of bovine source proteins in cell culture media has been a regulatory concerns, especially recently because of the outbreak of Bovine Spongiform Encephalopathy (BSE) in some countries. Rigorous and complex downstream purification process has to be developed to remove contaminating proteins and any adventitious viruses from the final product. Development of serum-free 293 suspension culture is deemed to be a major process improvement for the production of adenoviral vector for gene therapy.

Results of virus production in spinner flasks and a 3 L stirred tank bioreactor indicate that cell specific virus productivity of the 293SF cells was approximately $2.5\times10^4$ vp/cell, which is approximately 60-901% of that from the 293A cells. However, because of the higher stationary cell concentration, volumetric virus productivity from the 293SF culture is essentially equivalent to that of the 293A cell culture. The inventors also observed that virus production increased significantly by carrying out a fresh medium exchange at the time of virus infection. The inventors are going to evaluate the limiting factors in the medium.

These findings allow for a scaleable, efficient, and easily validatable process for the production adenoviral vector. This adaptation method is not limited to 293A cells only and will be equally useful when applied to other adenoviral vector producer cells.

3. Methods of Cell Harvest and Lysis

Adenoviral infection results in the lysis of the cells being infected. The lytic characteristics of adenovirus infection permit two different modes of virus production. One is harvesting infected cells prior to cell lysis. The other mode is harvesting virus supernatant after complete cell lysis by the produced virus. For the latter mode, longer incubation times are required in order to achieve complete cell lysis. This prolonged incubation time after virus infection creates a serious concern about increased possibility of generation of replication competent adenovirus (RCA), particularly for the current first generation adenoviral vectors (E1-deleted vector). Therefore, harvesting infected cells before cell lysis was chosen as the production mode of choice. Table 1 lists the most common methods that have been used for lysing cells after cell harvest.

TABLE 1

Methods used for cell lysis

| Methods | Procedures | Comments |
| --- | --- | --- |
| Freeze-thaw | Cycling between dry ice and 37° C. water bath | Easy to carry out at lab scale. High cell lysis efficiency Not scaleable Not recommended for large scale manufacturing |
| Solid Shear | French Press Hughes Press | Capital equipment investment Virus containment concerns Lack of experience |
| Detergent lysis | Non-ionic detergent solutions such as Tween, Triton, NP-40, etc. | Easy to carry out at both lab and manufacturing scale Wide variety of detergent choices Concerns of residual detergent in finished product |
| Hypotonic solution lysis | water, citric buffer | Low lysis efficiency |
| Liquid Shear | Homogenizer Impinging Jet Microfluidizer | Capital equipment investment Virus containment concerns Scaleability concerns |
| Sonication | ultrasound | Capital equipment investment Virus containment concerns Noise pollution Scaleability concern |

A) Detergents

Cells are bounded by membranes. In order to release components of the cell, it is necessary to break open the cells. The most advantageous way in which this can be accomplished, according to the present invention, is to solubilize the membranes with the use of detergents. Detergents are amphipathic molecules with an apolar end of aliphatic or aromatic nature and a polar end which may be charged or uncharged. Detergents are more hydrophilic than lipids and thus have greater water solubility than lipids. They allow for the dispersion of water insoluble compounds into aqueous media and are used to isolate and purify proteins in a native form.

Detergents can be denaturing or non-denaturing. The former can be anionic such as sodium dodecyl sulfate or cationic such as ethyl trimethyl ammonium bromide. These detergents totally disrupt membranes and denature the protein by breaking protein-protein interactions. Non denaturing detergents can be divided into non-anionic detergents such as Triton®X-100, bile salts such as cholates and zwitterionic detergents such as CHAPS. Zwitterionics contain both cationic and anion groups in the same molecule, the positive electric charge is neutralized by the negative charge on the same or adjacent molecule.

Denaturing agents such as SDS bind to proteins as monomers and the reaction is equilibrium driven until saturated. Thus, the free concentration of monomers determines the necessary detergent concentration. SDS binding is cooperative i.e. the binding of one molecule of SDS increase the probability of another molecule binding to that protein, and alters proteins into rods whose length is proportional to their molecular weight Non-denaturing agents such as Triton®X-100 do not bind to native conformations nor do they have a cooperative binding mechanism. These detergents have rigid and bulky apolar moieties that do not penetrate into water soluble proteins. They bind to the hydrophobic parts of proteins. Triton®X100 and other polyoxyethylene nonanionic detergents are inefficient in breaking protein-protein interaction and can cause artifactual aggregations of protein. These detergents will, however, disrupt protein-lipid interactions but are much gentler and capable of maintaining the native form and functional capabilities of the proteins.

Detergent removal can be attempted in a number of ways. Dialysis works well with detergents that exist as monomers. Dialysis is somewhat ineffective with detergents that readily aggregate to form micelles because they micelles are too large to pass through dialysis. Ion exchange chromatography can be utilized to circumvent this problem. The disrupted protein solution is applied to an ion exchange chromatography column and the column is then washed with buffer minus detergent. The detergent will be removed as a result of the equilibration of the buffer with the detergent solution. Alternatively the protein solution may be passed through a density gradient. As the protein sediments through the gradients the detergent will come off due to the chemical potential.

Often a single detergent is not versatile enough for the solubilization and analysis of the milieu of proteins found in a cell. The proteins can be solubilized in one detergent and then placed in another suitable detergent for protein analysis. The protein detergent micelles formed in the first step should separate from pure detergent micelles. When these are added to an excess of the detergent for analysis, the protein is found in micelles with both detergents. Separation of the detergent-protein micelles can be accomplished with ion exchange or gel filtration chromatography, dialysis or buoyant density type separations.

Triton®X-Detergents: This family of detergents (Triton®X-100, X114 and NP-40) have the same basic characteristics but are different in their specific hydrophobic-hydrophilic nature. All of these heterogeneous detergents have a branched 8-carbon chain attached to an aromatic ring. This portion of the molecule contributes most of the hydrophobic nature of the detergent. Triton®X detergents are used to solublize membrane proteins under non-denaturing conditions. The choice of detergent to solubilize proteins will depend on the hydrophobic nature of the protein to be solubilized. Hydrophobic proteins require hydrophobic detergents to effectively solubilize them.

Triton®X-100 and NP-40 are very similar in structure and hydrophobicity and are interchangeable in most applications including cell lysis, delipidation protein dissociation and membrane protein and lipid solubilization. Generally 2 mg detergent is used to solubilize 1 mg membrane protein or 10 mg detergent/1 mg of lipid membrane. Triton®X-114 is useful for separating hydrophobic from hydrophilic proteins.

Brij® Detergents: These are similar in structure to Triton®X detergents in that they have varying lengths of polyoxyethylene chains attached to a hydrophobic chain. However, unlike Triton®X detergents, the Brij® detergents do not have an aromatic ring and the length of the carbon chains can vary. The Brij® detergents are difficult to remove from solution using dialysis but may be removed by detergent removing gels. Brij®58 is most similar to Triton®X100 in its hydrophobic/hydrophilic characteristics. Brij®-35 is a commonly used detergent in HPLC applications.

Dializable Nonionic Detergents: η-Octyl-β-D-glucoside (octylglucopyranoside) and η-Octyl-β-D-thioglucoside (octylthioglucopyranoside, OTG) are nondenaturing nonionic detergents which are easily dialyzed from solution. These detergents are useful for solubilizing membrane proteins and, have low TV absorbances at 280 nm. Octylglucoside has a high CMC of 23-25 mM and has been used at concentrations of 1.1-1.2% to solubilize membrane proteins.

Octylthioglucoside was first synthesized to offer an alternative to octylglucoside. Octylglucoside is expensive to manufacture and there are some inherent problems in biological systems because it can be hydrolyzed by β-glucosidase.

Tween® Detergents: The Tween® detergents are nondenaturing, nonionic detergents. They are polyoxyethylene sorbitan esters of fatty acids. Tween® 20 and Tween® 80 detergents are used as blocking agents in biochemical applications and are usually added to protein solutions to prevent nonspecific binding to hydrophobic materials such as plastics or nitrocellulose. They have been used as blocking agents in ELISA and blotting applications. Generally, these detergents are used at concentrations of 0.01-1.0% to prevent nonspecific binding to hydrophobic materials.

Tween® 20 and other nonionic detergents have been shown to remove some proteins from the surface of nitrocellulose. Tween® 80 has been used: to solubilize membrane proteins, present nonspecific binding of protein to multiwell plastic tissue culture plates and to reduce nonspecific binding by serum proteins and biotinylated protein A to polystyrene plates in ELISA.

The difference between these detergents is the length of the fatty acid chain. Tween® 80 is derived from oleic acid with a $C_{18}$ chain while Tween® 20 is derived from lauric acid with a $C_{12}$ chain. The longer, fatty acid chain makes the Tween® 80 detergent less hydrophilic than Tween® 20 detergent. Both detergents are very soluble in water.

The Tween® detergents are difficult to remove from solution by dialysis, but Tween® 20 can be removed by detergent removing gels. The polyoxyethylene chain found in these detergents makes them subject to oxidation (peroxide formation) as is true with the Triton® X and Brij® series detergents.

Zwitterionic Detergents: The zwitterionic detergent, CHAPS, is a sulfobetaine derivative of cholic acid. This zwitterionic detergent is useful for membrane protein solubilization when protein activity is important. This detergent is useful over a wide range of pH (pH 2-12) and is easily removed from solution by dialysis due to high CMCs (8-10 mM). This detergent has low absorbances at 280 nm making it useful when protein monitoring at this wavelength is necessary. CHAPS is compatible with the BCA Protein Assay and can be removed from solution by detergent removing gel. Proteins can be iodinated in the presence of CHAPS CHAPS has been successfully used to solubilize intrinsic membrane proteins and receptors and maintain the functional capability of the protein. When cytochrome P-450 is solubilized in either Triton® X-100 or sodium cholate aggregates are formed.

B) Non-Detergent Methods

Various non-detergent methods, though not preferred, may be employed in conjunction with other advantageous aspects of the present invention:

Freeze-Thaw: This has been a widely used technique for lysis cells in a gentle and effective manner. Cells are generally frozen rapidly in, for example, a dry ice/ethanol bath until completely frozen, then transferred to a 37° C. bath until completely thawed. This cycle is repeated a number of times to achieve complete cell lysis.

Sonication: High frequency ultrasonic oscillations have been found to be useful for cell disruption. The method by which ultrasonic waves break cells is not fully understood but it is known that high transient pressures are produced when suspensions art subjected to ultrasonic vibration. The main disadvantage with this technique is that considerable amounts of heat are generated. In order to minimize heat effects specifically designed glass vessels are used to hold the cell suspension. Such designs allow the suspension to circulate away from the ultrasonic probe to the outside of the vessel where it is cooled as the flask is suspended in ice.

High Pressure Extrusion: This is a frequently used method to disrupt microbial cell. The French pressure cell employs pressures of $10.4 \times 10^7$ Pa (16,000 p.s.i) to break cells open. These apparatus consists of a stainless steel chamber which opens to the outside by means of a needle valve. The cell suspension is placed in the chamber with the needle valve in the closed position. After inverting the chamber, the valve is opened and the piston pushed in to force out any air in the chamber. With the valve in the closed position, the chamber is restored to its original position, placed on a solid based and the required pressure is exerted on the piston by a hydraulic press. When the pressure has been attained the needle valve is opened fractionally to slightly release the pressure and as the cells expand they burst. The valve is kept open while the pressure is maintained so that there is a trickle of ruptured cell which may be collected.

Solid Shear Methods: Mechanical shearing with abrasives may be achieved in Mickle shakers which oscillate suspension vigorously (300-3000 time/min) in the presence of glass beads of 500 nm diameter. This method may result in organelle damage. A more controlled method is to use a Hughes press where a piston forces most cells together with abrasives or deep frozen paste of cells through a 0.25 mm diameter slot in the pressure chamber. Pressures of up to $5.5 \times 10^7$ Pa (8000 p.s.i.) may be used to lyse bacterial preparations.

Liquid Shear Methods: These methods employ blenders, which use high speed reciprocating or rotating blades, homogenizers which use an upward/downward motion of a plunger and ball and microfluidizers or impinging jets which use high velocity passage through small diameter tubes or high velocity impingement of two fluid streams. The blades of blenders are inclined at different angles to permit efficient mixing. Homogenizers are usually operated in short high speed bursts of a few seconds to minimize local heat. These techniques are not generally suitable for microbial cells but even very gentle liquid shear is usually adequate to disrupt animal cells.

Hypotonic/Hypertonic Methods: Cells are exposed to a solution with a much lower (hypotonic) or higher (hypertonic) solute concentration. The difference in solute concentration creates an osmotic pressure gradient. The resulting flow of water into the cell in a hypotonic environment causes the cells to swell and burst. The flow of water out of the cell in a hypertonic environment causes the cells to shrink and subsequently burst.

4. Methods of Concentration and Filtration

One aspect of the present invention employs methods of crude purification of adenovirus from a cell lysate. These methods include clarification, concentration and diafiltration. The initial step in this purification process is clarification of the cell lysate to remove large particulate matter, particularly cellular components, from the cell lysate. Clarification of the lysate can be achieved using a depth filter or by tangential flow filtration. In a preferred embodiment of the present invention, the cell lysate is passed through a depth filter, which consists of a packed column of relatively non-adsorbent material (e.g. polyester resins, sand, diatomeceous earth, colloids, gels, and the like). In tangential flow filtration (TFF), the lysate solution flows across a membrane surface which facilitates back diffusion of solute from the membrane surface into the bulk solution. Membranes are generally arranged within various types of filter apparatus including open channel plate and frame, hollow fibers, and tubules.

After clarification and prefiltration of the cell lysate, the resultant virus supernatant is first concentrated and then the buffer is exchanged by diafiltration. The virus supernatant is concentrated by tangential flow filtration across an ultrafiltration membrane of 100-300K nominal molecular weight cutoff. Ultrafiltration is a pressure-modified convective process that uses semi-permeable membranes to separate species by molecular size, shape and/or charge. It separates solvents from solutes of various sizes, independent of solute molecular size. Ultrafiltration is gentle, efficient and can be used to simultaneously concentrate and desalt solutions. Ultrafiltration membranes generally have two distinct layers: a thin (0.1-1.5 μm), dense skin with a pore diameter of 10-400 angstroms and an open substructure of progressively larger voids which are largely open to the permeate side of the ultrafilter. Any species capable of passing through the pores of the skin can therefore freely pass through the membrane. For maximum retention of solute, a membrane is selected that has a nominal molecular weight cut-off well below that of the species being retained. In macromolecular concentration, the membrane enriches the content of the desired biological species and provides filtrate cleared of retained substances. Microsolutes are removed convectively with the solvent. As concentration of the retained solute increases, the ultrafiltration rate diminishes.

Diafiltration, Or buffer exchange, using ultrafilters is an ideal way for removal and exchange of salts, sugars, non-aqueous solvents separation of free from bound species, removal of material of low molecular weight, or rapid change of ionic and pH environments. Microsolutes are removed most efficiently by adding solvent to the solution being ultrafiltered at a rate equal to the ultrafiltration rate. This washes microspecies from the solution at constant volume, purifying the retained species. The present invention utilizes a diafiltration step to exchange the buffer of the virus supernatant prior to Benzonase® treatment.

5. Viral Infection

The present invention employs, in one example, adenoviral infection of cells in order to generate therapeutically significant vectors. Typically, the virus will simply be exposed to the appropriate host cell under physiologic conditions, permitting uptake of the virus. Though adenovirus is exemplified, the present methods may be advantageously employed with other viral vectors, as discussed below.

A) Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. Elimination of large potions of the adenoviral genome, and providing the delete gene products in trans, by helper virus and/or helper cells, allows for the insertion of large portions of heterologous DNA into the vector. This strategy also will result in reduced toxicity and immunogenicity of the adenovirus gene products.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194-385 bp (0.5-1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (E1A) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

B) Retrovirus

Although adenoviral infection of cells for the generation of therapeutically significant vectors is a preferred embodiments of the present invention, it is contemplated that the present invention may employ retroviral infection of cells for the purposes of generating such vectors. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env— that code for capsid proteins, polymerase enzyme, and envelope components, respectively. A sequence found upstream from the gag gene, termed Y, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Y components is constructed (Mann et al., 1983). When a recombinant plasmid containing a human cDNA, together with the retroviral LTR and Y sequences is introduced into this cell line (by calcium phosphate precipitation for example), the Y sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of galactose residues to the viral envelope. This modification could permit the specific infection of cells such as hepatocytes via asialoglycoprotein receptors should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

C) Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984) and herpesviruses may be employed. These viruses offer several features for use in gene transfer into various mammalian cells.

6. Engineering of Viral Vectors

In certain embodiments, the present invention further involves the manipulation of viral vectors. Such methods involve the use of a vector construct containing, for example, a heterologous DNA encoding a gene of interest and a means for its expression, replicating the vector in an appropriate helper cell, obtaining viral particles produced therefrom, and infecting cells with the recombinant virus particles. The gene could simply encode a protein for which large quantities of the protein arm desired, i.e., large scale in vitro production methods. Alternatively, the gene could be a therapeutic gene, for example to treat cancer cells, to express immunomodulatory genes to fight viral infections, or to replace a gene's function as a result of a genetic defect. In the context of the gene therapy vector, the gene will be a heterologous DNA, meant to include DNA derived from a source other than the viral genome which provides the backbone of the vector. Finally, the virus may act as a live viral vaccine and express an antigen of interest for the production of antibodies thereagainst. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA may also include a regulatory sequence which may be derived from one source and the gene from a different source.

A) Therapeutic Genes p53 currently is recognized as a tumor suppressor gene (Montenarh, 1992). High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers (Mercer, 1992). It is mutated in over 50% of human NSCLC (Hollestein et al, 1991) and in a wide spectrum of other tumors.

The p53 gene encodes a 393-amino-acid phosphoprotein that can form complexes, with host proteins such as large-T antigen and E1B. The protein is found in normal tissues and cells, but at concentrations which are generally minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus p53 can act as a negative regulator of cell growth (Weinberg, 1991) and may directly suppress uncontrolled cell growth or directly or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992) p53 appears dominant over the mutant gene and will select against proliferation when transfected into cells with the mutant gene. Normal expression of the transfected p53 is not detrimental to normal cells with endogenous wild-type p53. Thus, such constructs might be taken up by normal cells without adverse effects. It is thus proposed that the treatment of p53-associated cancers with wild-type p53 expression constructs will reduce the number of malignant cells or their growth rate. Furthermore, recent studies suggest that some p53 wild-type tumors are also sensitive to the effects of exogenous p53 expression.

The major transitions of the eukaryotic cell cycle are triggered by cyclin-dependent kinases, or CDK's. One CDK, cyclin-dependent kinase 4 (CDK4), regulates progression through the $G_1$ phase. The activity of this enzyme may be to phosphorylate. Rb at late $G_1$. The activity of CDK4 is controlled by an activating subunit, D-type cyclin, and by an inhibitory subunit, e.g. $p16^{INK4}$, which has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein p16 also is known to regulate the function of CDK6.

$p16^{INK4}$ belongs to a newly described class of CDK-inhibitory proteins that also includes $p16^B$, $p21^{WAF1, CIP1, SDII}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994a; Kamb et al., 1994b; Mori et al., 1994; Okamoto et al., 1994; Nobori et al., 1995; Orlow et. al., 1994; Arap et al., 1995). Restoration of wild-type $p16^{INK4}$ function by transfection with a plasmid expression vector reduced colony formation by some human cancer cell lines (Okamoto, 1994; Arap, 1995).

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993a; 1993b and 1993c) demonstrated that the first Ig domain of C-CAM is critical for cell adhesion activity.

Cell adhesion molecules, or CAMs are known to be involved in a complex network of molecular interactions that regulate organ development and cell differentiation (Edelman, 1985). Recent data indicate that aberrant expression of CAMs may be involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumor growth in vitro and in vivo.

Other tumor suppressors that may be employed according to the present invention include RB, APC, DCC, NF-1, NF-2, WT-1, MEN-I, MEN-II, zac1, p73, BRCA1, VHL, FCC, MMAC1, MCC, p16, p21, p57, C-CAM, p27 and BRCA2. Inducers of apoptosis, such as Bax, Bak, Bcl-$X_s$, Bik, Bid, Harakiri, Ad E1B, Bad and ICE-CED3 proteases, similarly could find use according to the present invention.

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

Hormones are another group of gene that may be used in the vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1-40), parathyroid hormone-related protein (107-139) (PTH-rP), parathyroid hormone-related protein (107-111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, alpha melanocyte stimulating hormone (alpha-MSH), atrial natriuretic factor (5-28) (ANF), amylin, amyloid P component (SAP-1), corticotropin releasing hormone (CRH), growth hormone releasing factor (GHRF), luteinizing hormone-releasing hormone (LHRH), neuropeptide Y, substance K (neurokinin A), substance P and thyrotropin releasing hormone (TRH).

Other classes of genes that are contemplated to be inserted into the vectors of the present invention include interleukins and cytokines. Interleukin 1 (IL-1), IL-2, IL-3, IL-4, IL-5, IL-6, IL-7, IL-8, IL-9, IL-10, IL-11 IL-12, GM-CSF and G-CSF.

Examples of diseases for which the present viral vector would be useful include, but are not limited to, adenosine deaminase deficiency, human blood clotting factor IX deficiency in hemophilia B, and cystic fibrosis, which would involve the replacement of the cystic fibrosis transmembrane receptor gene. The vectors embodied in the present invention could also be used for treatment of hyperproliferative disorders such as rheumatoid arthritis or restenosis by transfer of genes encoding angiogenesis inhibitors or cell cycle inhibitors. Transfer of prodrug activators such as the HSV-TK gene can be also be used in the treatment of hyperploiferative disorders, including cancer.

B) Antisense Constructs

Oncogenes such as ras, myc, neu, raf erb, src, fms, jun, trk, ret, gsp, hst, bcl and abl also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementarity rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" refers to an RNA-based enzyme capable of targeting and cleaving particular base sequences in oncogene DNA and RNA. Ribozymes can either be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

C) Antigens for Vaccines

Other therapeutics genes might include genes encoding antigens such as viral antigens, bacterial antigens, fungal antigens or parasitic antigens. Viruses include picornavirus, coronavirus, togavirus, flavirviru, rhabdovirus, paramyxovirus, orthomyxovirus, bunyavirus, arenvirus, reovirus, retrovirus, papovavirus, parvovirus, herpesvirus, poxvirus, hepadnavirus, and spongiform virus. Preferred viral targets include influenza, herpes simplex virus 1 and 2, measles, small pox, polio or HIV. Pathogens include trypanosomes, tapeworms, roundworms, helminths. Also, tumor markers, such as fetal antigen or prostate specific antigen, may be targeted in this manner. Preferred examples include HIV env proteins and hepatitis B surface antigen Administration of a vector according to the present invention for vaccination purposes would require that the vector-associated antigens be sufficiently non-immunogenic to enable long term expression of the transgene, for which a strong immune response would be desired. Preferably, vaccination of an individual would only be required infrequently, such as yearly or biennially, and provide long term immunologic protection against the infectious agent.

D) Control Regions

In order for the viral vector to effect expression of a transript encoding a therapeutic gene, the polynucleotide encoding the therapeutic gene will be under the transcriptional control of a promoter and a polyadenylation signal. A "promoter" refers to a DNA sequence recognized by the synthetic machinery of the host cell, or introduced synthetic machinery, that is required to initiate the specific transcription of a gene. A polyadenylation signal refers to a DNA sequence recognized by the synthetic machinery of the host cell, or introduced synthetic machinery, that is required to direct the addition of a series of nucleotides on the end of the mRNA transcript for proper processing and trafficking of the transcript out of the nucleus into the cytoplasm for translation. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements arm inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter-that is employed to control the expression of a therapeutic gene is not believed to be critical, so long as it is capable of expressing the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter. A list of promoters is provided in the Table 2.

TABLE 2

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins(GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |

TABLE 2-continued

| PROMOTER |
| --- |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

The promoter further may be characterized as an inducible promoter. An inducible promoter is a promoter which is inactive or exhibits low activity except in the presence of an inducer substance. Some examples of promoters that may be included as a part of the present invention include, but are not limited to, MT II, MMTV, Colleganse, Stromelysin, SV40, Murine MX gene, α-2-Macroglobulin, MHC class I gene h-2kb, HSP70, Proliferin, Tumor Necrosis Factor, or Thyroid Stimulating Hormone α gene. The associated inducers are shown in Table 3. It is understood that any inducible promoter may be used in the practice of the present invention and that all such promoters would fall within the spirit and scope of the claimed invention.

TABLE 3

| Element | Inducer |
| --- | --- |
| MT II | Phorbol Ester(TPA) |
|  | Heavy metals |
| MMTV (mouse mammary tumor virus) | Glucocorticoids |
| β-Interferon | poly(rI)X |
|  | poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |

In various embodiments, the human cytomegalovirus (CMV) immediate early gene promoter, the SV40 early promoter and the Rous sarcoma virus long terminal repeat can be used to obtain high-level expression of the polynucleotide of interest. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of the therapeutic gene.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base (EPDB)) could also be used to drive expression of a particular construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. Such polyadenylation signals as that from SV40, bovine growth hormone, and the herpes simplex virus thymidine kinase gene have been found to function well in a number of target cells.

7. Methods of Gene Transfer

In order to create the helper cell lines of the present invention, and to create recombinant adenovirus vectors for use therewith, various genetic (i.e. DNA) constructs must be delivered to a cell. One way to achieve this is via viral transductions using infectious viral particles, for example, by transformation with an adenovirus vector of the present invention. Alternatively, retroviral or bovine papilloma virus may be employed, both of which permit permanent transformation of a host cell with a gene(s) of interest. In other situations, the nucleic acid to be transferred is not infectious, i.e., contained in an infectious virus particle. This genetic material must rely on non-viral methods for transfer.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet farther embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularity applicable for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other expression constructs which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

8. Removing Nucleic Acid Contaminants

The present invention employs nucleases to remove contaminating nucleic acids. Exemplary nucleases include Benzonase®, Pulmozyme®; or any other DNase or RNase commonly used within the art.

Enzymes such as Benzonaze® degrade nucleic acid and have no proteolytic activity. The ability of Benzonase® to rapidly hydrolyze nucleic acids makes the enzyme ideal for reducing cell lysate viscosity. It is well known that nucleic acids may adhere to cell derived particles such as viruses. The adhesion may interfere with separation due to agglomeration, change in size of the particle or change in particle charge, resulting in little if any product being recovered with a given purification scheme. Benzonase® is well suited for reducing the nucleic acid load during purification, thus eliminating the interference and improving yield.

As with all endonucleases, Benzonase® hydrolyzes internal phosphodiester bonds between specific nucleotides. Upon complete digestion, all free nucleic acids present in solution are reduced to oligonucleotides 2 to 4 bases in length.

9. Purification Techniques

The present invention employs a number of different purification to purify adenoviral vectors of the present invention. Such techniques include those based on sedimentation and chromatography and are described in more detail herein below.

A) Density Gradient Centrifugation

There are two methods of density gradient centrifugation, the rate zonal technique and the isopycnic (equal density) technique, and both can be used when the quantitative separation of all the components of a mixture of particles is required. They are also used for the determination of buoyant densities and for the estimation of sedimentation coefficients.

Particle separation by the rate zonal technique is based upon differences in size or sedimentation rates. The technique involves carefully layering a sample solution on top of a performed liquid density gradient, the highest density of which exceeds that of the densest particles to be separated. The sample is then centrifuged until the desired degree of separation is effected, i.e., for sufficient time for the particles to travel through the gradient to form discrete zones or bands which are spaced according to the relative velocities of the particles. Since the technique is time dependent, centrifugation must be terminated before any of the separated zones pellet at the bottom of the tube. The method has been used for the separation of enzymes, hormones, RNA-DNA hybrids, ribosomal subunits, subcellular organelles, for the analysis of size distribution of samples of polysomes and for lipoprotein fractionations.

The sample is layered on top of a continuous density gradient which spans the whole range of the particle densities which are to be separated. The maximum density of the gradient, therefore, must always exceed the density of the most dense particle. During centrifugation, sedimentation of the particles occurs until the buoyant density of the particle and the density of the gradient are equal (i.e., where $p_p=p_m$ in equation 2.12). At this point no further sedimentation occurs, irrespective of how long centrifugation continues, because the particles are floating on a cushion of material that has a density greater than their own.

Isopycnic centrifugation, in contrast to the rate zonal technique, is an equilibrium method, the particles banding to form zones each at their own characteristic buoyant density. In cases where, perhaps, not all the components in a mixture of particles are required, a gradient range can be selected in which unwanted components of the mixture will sediment to the bottom of the centrifuge tube whilst the particles of interest sediment to their respective isopycnic positions. Such a technique involves a combination of both the rate zonal and isopycnic approaches.

Isopycnic centrifugation depends solely upon the buoyant density of the particle and not its shape or size and is independent of time. Hence soluble proteins, which have a very similar density (e.g., $p=1.3$ g cm$^{-3}$ in sucrose solution), cannot usually be separated by this method, whereas subcellular organelles (e.g., Golgi apparatus, $p=1.11$ g cm$^{-3}$, mitochondria, $p=1.19$ g cm$^{-3}$ and peroxisomes, $p=1.23$ g cm$^{-3}$ in sucrose solution) can be effectively separated.

As an alternative to layering the particle mixture to be separated onto a preformed gradient, the sample is initially mixed with the gradient medium to give a solution of uniform density, the gradient 'self-forming', by sedimentation equilibrium, during centrifugation. In this method (referred to as the equilibrium isodensity method), use is generally made of the salts of heavy metals (e.g., caesium or rubidium), sucrose, colloidal silica or Metrizamide.

The sample (e.g., DNA) is mixed homogeneously with, for example, a concentrated solution of caesium chloride. Centrifugation of the concentrated caesium chloride solution results in the sedimentation of the CsCl molecules to form a concentration gradient and hence a density gradient. The sample molecules (DNA), which were initially uniformly distributed throughout the tube now either rise or sediment until they reach a region where the solution density is equal to their own buoyant density, i.e. their isopycnic position, where they will band to form zones. This technique suffers from the disadvantage that often very long centrifugation times (e.g., 36 to 48 hours) are required to establish equilibrium. However, it is commonly used in analytical centrifugation to determine the buoyant density of a particle, the base composition of double stranded DNA and to separate linear from circular forms of DNA.

Many of the separations can be improved by increasing the density differences between the different forms of DNA by the incorporation of heavy isotope (e.g., $^{15}$N) during biosynthesis, a technique used by Leselson and Stahl to elucidate the mechanism of DNA replication in *Esherichia coli*, or by the binding of heavy metal ions or dyes such as ethidium bromide. Isopycnic gradients have also been used to separate and purify viruses and analyze human plasma lipoproteins.

B) Chromatography

In certain embodiments of the invention, it will be desirable to produce purified adenovirus. Purification techniques are well known to those of skill in the art. These techniques tend to involve the fractionation of the cellular milieu to separate the adenovirus particles from other components of the mixture. Having separated adenoviral particles from the other components, the adenovirus may be purified using chromatographic and electrophoretic techniques to achieve complete purification. Analytical methods particularly suited to the preparation of a pure adenovrial particle of the present invention are ion-exchange chromatography, size exclusion chromatography; polyacrylamide gel electrophoresis. A particularly efficient purification method to be employed in conjunction with the present invention is HPLC.

Certain aspects of the present invention concern the purification, and in particular embodiments, the substantial purification, of an adenoviral particle. The term "purified" as used herein, is intended to refer to a composition, isolatable from other components, wherein the adenoviral particle is purified to any degree relative to its naturally-obtainable form. A purified adenoviral particle therefore also refers to an adenoviral component, free from the environment in which it may naturally occur.

Generally, "purified" will refer to an adenoviral particle that has been subjected to fractionation to remove various other components, and which composition substantially retains its expressed biological activity. Where the term "substantially purified" is used, this designation will refer to a composition in which the particle, protein or peptide forms the major component of the composition, such as constituting about 50% or more of the constituents in the composition.

Various methods for quantifying the degree of purification of a protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

There is no general requirement that the adenovirus, always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater -fold purification than the same technique utilizing a low pressure chromatography system. Methods exhibiting a lower degree of relative purification may have advantages in total recovery of protein product, or in maintaining the activity of an expressed protein.

Of course, it is understood that the chromatographic techniques and other purification techniques known to those of skill in the art may also be employed to purify proteins expressed by the adenoviral vectors of the present invention. Ion exchange chromatography and high performance liquid chromatography are exemplary purification techniques employed in the purification of adenoviral particles and are described in further detail herein below.

Ion-Exchange Chromatography. The basic principle of ion-exchange chromatography is that the affinity of a substance for the exchanger depends on both the electrical properties of the material and the relative affinity of other charged substances in the solvent. Hence, bound material can be eluted by changing the pH, thus altering the charge of the material, or by adding competing materials, of which salts are but one example. Because different substances have different electrical properties, the conditions for release vary with each bound molecular species. In general, to get good separation, the methods of choice are either continuous ionic strength gradient elution or stepwise elution. (A gradient of pH alone is not often used because it is difficult to set up a pH gradient without simultaneously increasing ionic strength.) For an anion exchanger, either pH and ionic strength are gradually increased or ionic strength alone is increased. For a cation exchanger, both pH and ionic strength are increased. The act choice of the elution procedure is usually a result of trial and error and of considerations of stability. For example, for unstable materials, it is best to maintain fairly constant pH.

An ion exchanger is a solid that has chemically bound charged groups to which ions are electrostatically bound; it can exchange these ions for ions in aqueous solution. Ion exchangers can be used in column chromatography to separate molecules according to charge; actually other features of the molecule are usually important so that the chromatographic behavior is sensitive to the charge density, charge distribution, and the size of the molecule.

The principle of ion-exchange chromatography is that charged molecules adsorb to ion exchangers reversibly so that molecules can be bound or eluted by changing the ionic environment. Separation on ion exchangers is usually accomplished in two stages: first, the substances to be separated are bound to the exchanger, using conditions that give stable and tight binding; then the column is eluted with buffers of different pH, ionic strength, or composition and the components of the buffer compete with the bound material for the binding sites.

An ion exchanger is usually a three-dimensional network or matrix that contains covalently linked charged groups. If a group is negatively charged, it will exchange positive ions and is a cation exchanger. A typical group used in cation exchangers is the sulfonic group, $SO_3^-$. If an $H^+$ is bound to the group, the exchanger is said to be in the acid form; it can, for example, exchange on $H^+$ for one $Na^+$ or two $H^+$ for one $Ca^{2+}$. The sulfonic acid group is called a strongly acidic cation exchanger. Other commonly used groups are phenolic hydroxyl and carboxyl, both weakly acidic cation exchangers. If the charged group is positive—for example, a quaternary amino group—it is a strongly basic anion exchanger. The most common weakly basic anion exchangers are aromatic or aliphatic amino groups.

The matrix can be made of various material. Commonly used materials are dextran, cellulose, agarose and copolymers of styrene and vinylbenzene in which the divinylbenzene both cross-links the polystyrene strands and contains the charged groups. Table 4 gives the composition of many ion exchangers.

The total capacity of an ion exchanger measures its ability to take up exchangeable groups per milligram of dry weight. This number is supplied by the manufacturer and is important because, if the capacity is exceeded, ions will pass through the column without binding.

TABLE 4

| Matrix | Exchanger | Functional Group | Tradename |
|---|---|---|---|
| Dextran | Strong Cationic | Sulfopropyl | SP-Sephadex |
| | Weak Cationic | Carboxymethyl | CM-Sephadex |
| | Strong Anionic | Diethyl-(2-hydroxypropyl)-aminoethyl | QAE-Sephadex |
| | Weak Anionic | Diethylaminoethyl | DEAE-Sephadex |
| Cellulose | Cationic | Carboxymethyl | CM-Cellulose |
| | Cationic | Phospho | P-cel |
| | Anionic | Diethylaminoethyl | DEAE-cellulose |
| | Anionic | Polyethylenimine | PEI-Cellulose |
| | Anionic | Benzoylated-naphthoylated, deiethylaminoethyl | DEAE(BND)-cellulose |
| | Anionic | p-Aminobenzyl | PAB-cellulose |
| Styrene-divinyl-benzene | Strong Cationic | Sulfonic acid | AG 50 |
| | Strong Anionic | | AG 1 |
| | Strong Cationic + Strong Anionic | Sulfonic acid + Tetramethylammonium | AG 501 |
| Acrylic | Weak Cationic | Carboxylic | Bio-Rex 70 |
| Phenolic | Strong Cationic | Sulfonic acid | Bio-Rex 40 |
| Expoxyamine | Weak Anionic | Tertiary amino | AG-3 |

The available capacity is the capacity under particular experimental conditions (i.e., pH, ionic strength). For example, the extent to which an ion exchanger is charged depends on the pH (the effect of pH is smaller with strong ion exchangers). Another factor is ionic strength because small ions near the charged groups compete with the sample molecule for these groups. This competition is quite effective if the sample is a macromolecule because the higher diffusion coefficient of the small ion means a greater number of encounters. Clearly, as buffer concentration increases, competition becomes keener.

The porosity of the matrix is an important feature because the charged groups are both inside and outside the matrix and because the matrix also acts as a molecular sieve. Large molecules may be unable to penetrate the pores; so the capacity will decease with increasing molecular dimensions. The porosity of the polystyrene-based resins is determined by the amount of cross-linking by the divinylbenzene (porosity decreases with increasing amounts of divinylbenzene). With the Dowex and AG series, the percentage of divinylbenzene is indicated by a number after an X—hence, Dowex 50-X8 is 8% divinylbenzene Ion exchangers come in a variety of particle sizes, called mesh size. Finer mesh means an increased surface-to-volume ration and therefore increased capacity and decreased time for exchange to occur for a given volume of the exchanger. On the other hand, fine mesh means a slow flow rate, which can increase diffusional spreading. The use of very fine particles, approximately 10 μm in diameter and high pressure to maintain an adequate flow is called high-performance or high-pressure liquid chromatography or simply HPLC.

Such a collection of exchangers having such different properties—charge, capacity, porosity, mesh—makes the selection of the appropriate one for accomplishing a particular separation difficult. How to decide on the type of column material and the conditions for binding and elution is described in the following Examples.

There are a number of choice to be made when employing ion exchange chromatography as a technique. The first choice to be made is whether the exchanger is to be anionic or cationic. If the materials to be bound to the column have a single charge (i.e., either plus or minus), the choice is clear. However, many substances (e.g., proteins, viruses), carry both negative and positive charges and the net charge depends on the pH. In such cases, the primary factor is the stability of the substance at various pH values. Most proteins have a pH range of stability (i.e., in which they do not denature) in which they are either positively or negatively charged. Hence, if a protein is stable at pH values above the isoelectric point, an anion exchanger should be used; if stable at values below the isoelectric point, a cation exchanger is required.

The choice between strong and weak exchangers is also based on the effect of pH on charge and stability. For example, if a weakly ionized substance that requires very low or high pH for ionization is chromatographed, a strong ion exchanger is called for because it functions over the entire pH range. However, if the substance is labile, weak ion exchangers are preferable because strong exchangers are often capable of distorting a molecule so much that the molecule denatures. The pH at which the substance is stable must, of course, be matched to the narrow range of pH in which a particular weak exchanger is charged. Weak ion exchangers are also excellent for the separation of molecules with a high charge from those with a small charge, because the weakly charged ions usually fail to bind. Weak exchangers also show greater resolution of substances if charge differences are very small. If a macromolecule has a very strong charge, it may be impossible to elute from a strong exchanger and a weak exchanger again may be preferable. In general, weak exchangers are more useful than strong exchangers.

The Sephadex and Bio-gel exchangers offer a particular advantage for macromolecules that are unstable in low ionic strength. Because the cross-links in these materials maintain the insolubility of the matrix even if the matrix is highly polar, the density of ionizable groups can be made several times greater than is possible with cellulose ion exchangers. The increased charge density means increased affinity so that adsorption can be carried out at higher ionic strengths. On the other hand, these exchangers retain some of their molecular sieving properties so that sometimes molecular weight differences annul the distribution caused by the charge differences; the molecular sieving effect may also enhance the separation.

Small molecules are best separated on matrices with small pore size (high degree of cross-linking) because the available capacity is large, whereas macromolecules need large pore size. However, except for the Sephadex type, most ion exchangers do not afford the opportunity for matching the porosity with the molecular weight.

The cellulose ion exchangers have proved to be the best for purifying large molecules such as proteins and polynucleotides. This is because the matrix is fibrous, and hence all functional groups are on the surface and available to even the largest molecules. In may cases however, beaded forms such as DEAE-Sephacel and DEAE-Biogel P are more useful because there is a better flow rate and the molecular sieving effect aids in separation.

Selecting a mesh size is always difficult. Small mesh size improves resolution but decreases flow rate, which increases zone spreading and decreases resolution. Hence, the appropriate mesh size is usually determined empirically.

Because buffers themselves consist of ions, they can also exchange, and the pH equilibrium can be affected. To avoid these problems, the rule of buffers is adopted: use cationic buffers with anion exchangers and anionic buffers with cation exchangers. Because ionic strength is a factor in binding, a buffer should be chosen that has a high buffering capacity so that its ionic strength need not be too high. Furthermore, for best resolution, it has been generally found that the ionic conditions used to apply the sample to the column (the so-called starting conditions) should be near those used for eluting the column.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

10. Pharmaceutical Compositions and Formulations

When purified according to the methods set forth above, the viral particles of the present invention will be administered, in vitro, ex vivo or in vivo is contemplated. Thus, it will be desirable to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the expression construct and nucleic acid, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The viral particles of the present invention may include classic pharmaceutical preparations for use in therapeutic regimens, including their administration to humans. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal, or intravenous injection. Such compositions would normally be administered as pharmaceutically acceptable compositions that include physiologically acceptable carriers, buffers or other excipients. For application against tumors, direct intratumoral injection, inject of a resected tumor bed, regional (i.e., lymphatic) or general administration is contemplated. It also may be desired to perform continuous perfusion over hours or days via a catheter to a disease site, e.g., a tumor or tumor site.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations which are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal, for example (i) inhibition of tumor cell proliferation, (ii) elimination or killing of tumor cells, (iii) vaccination, or (iv) gene transfer for long term expression of a therapeutic gene. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the result desired. Multiple gene therapeutic regimens are expected, especially for adenovirus.

In certain embodiments of the present invention, an adenoviral vector encoding a tumor suppressor gene will be used to treat cancer patients. Typical amounts of an adenovirus vector used in gene therapy of cancer is $10^3$-$10^{15}$ PFU/dose, ($10^3$, $10^4$, $10^5$, $10^6$, $10^7$, $10^8$, $10^9$, $10^{10}$, $10^{11}$, $10^{12}$, $10^{13}$, $10^{14}$, $10^{15}$) wherein the dose may be divided into several injections at different sites within a solid tumor. The treatment regimen also may involve several cycles of administration of the gene transfer vector over a period of 3-10 weeks. Administration of the vector for longer periods of time from months to years may be necessary for continual therapeutic benefit.

In another embodiment of the present invention, an adenoviral vector encoding a therapeutic gene may be used to vaccinate humans or other mammals. Typically, an amount of virus effective to produce the desired effect, in this case vaccination, would be administered to a human or mammal so that long term expression of the transgene is achieved and a strong host immune response develops. It is contemplated that a series of injections, for example, a primary injection followed by two booster injections, would be sufficient to induce an long term immune response. A typical dose would be from $10^6$ to $10^{15}$ PFU/injection depending on the desired result. Low doses of antigen generally induce a strong cell-mediated response, whereas high doses of antigen generally induce an antibody-mediated immune response. Precise amounts of the therapeutic composition also depend on the judgment of the practitioner and are peculiar to each individual.

11. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

A) Cells 293 cells (human epithelial embryonic kidney cells) from the Master Cell Bank were used for the studies.

B) Media

Dulbecco's modified Eagle's medium (DMEM, 4.5 g/L glucose)+10% fetal bovine serum (FBS) was used for the cell growth phase. For the virus production phase, the FBS concentration in DMEM was lowered to 2%.

C) Virus

AdCMVp53 is a genetically engineered, replication-incompetent human type 5 adenovirus expressing the human wild type p53 protein under control of the cytomegalovirus (CMV) immediate early promoter.

D) Celligen Bioreactor

A Celligen bioreactor (New Brunswick Scientific, Co. Inc.) with 5 L total volume (3.5 L working volume) was used to produce virus supernatant using microcarrier culture. 13 g/L glass coated microcarrier (SoloHill) was used for culturing cells in the bioreactor.

E) Production of Virus Supernatant in the Celligen Bioreactor 293 cells from master cell bank (MCB) were thawed and expanded into Cellfactories (Nunc). Cells were generally split at a confluence of about 85-90%. Cells were inoculated into the bioreactor at an inoculation concentration of $1 \times 10^5$ cells/ml. Cells were allowed to attach to the microcarriers by intermittent agitation. Continuous agitation at a speed of 30 rpm was started 6-8 hr post cell inoculation. Cells were cultured for 7 days with process parameters set at pH=7.20, dissolved oxygen (DO)=60% of air saturation, temperature=37° C. On day 8, cells were infected with AdCMVp53 at an MOI of 5. Fifty hr post virus infection, agitation speed was increased from 30 rpm to 150 rpm to facilitate cell lysis and release of the virus into the supernatant. The virus supernatant was harvested 74 hr post-infection. The virus supernatant was then filtered for further concentration/diafiltration.

F) Cellcube™ Bioreactor System

A Cellcube™ bioreactor system (Coring-Costar) was also used for the production of AdCMVp53 virus. It is composed of a disposable cell culture module, an oxygenator, a medium recirculation pump and a medium pump for perfusion. The cell culture module used has a culture surface area of 21,550 $cm^2$ (1 mer).

G) Production of Virus in the Cellcube™

293 cells from master cell bank (MCB) were thawed and expanded into Cellfactories (Nunc). Cells were generally split at a confluence of about 85-90%. Cells were inoculated into the Cellcube™ according to the manufacturer's recommendation. Inoculation cell densities were in the range of $1\text{-}1.5 \times 10^4/cm^2$. Cells were allowed to grow for 7 days at 37° C. under culture conditions of pH=7.20, DO=60% air saturation. Medium perfusion rate was regulated according to the glucose concentration in the Cellcube™. One day before viral infection, medium for perfusion was changed from DMEM+10% FBS to DMEM+2% FBS. On day 8, cells were infected with AdCMVp53 virus at a multiplicity of infection (MOI) of 5. Medium perfusion was stopped for 1 hr immediately after infection then resumed for the remaining period of the virus production phase. Culture was harvested 45-48 hr post-infection.

H) Lysis Solution

Tween-20 (Fisher Chemicals) at a concentration of 1% (v/v) in 20 mM Tris+0.25 M NaCl+1 mM $MgCl_2$, pH=7.50 buffer was used to lyse cells at the end of the virus production phase in the Cellcube™.

I) Clarification and Filtration

Virus supernatant from the Celligen bioreactor and virus solution from the Cellcube™ were first clarified using a depth filter (Preflow, GelmanSciences), then was filtered through a 0.8/0.22 μm filter (SuporCap 100, GelmanSciences).

J) Concentration/Diafiltration

Tangential flow filtration (TFF) was used to concentrate and buffer exchange the virus supernatant from the Celligen bioreactor and the virus solution from the Cellcube™. A Pellicon II mini cassette (Millipore) of 300 K nominal molecular weight cut off (NMWC) was used for the concentration and diafiltration. Virus solution was first concentrated 10-fold. This was followed by 4 sample volume of buffer exchange against 20 mM Tris+1.0 M NaCl+1 mM $MgCl_2$, pH=9.00 buffer using the constant volume diafiltration method.

Similar concentration/diafiltration was carried out for the column purified virus. A Pellicon II mini cassette of 100 K NMWC was used instead of the 300 K NMWC cassette. Diafiltration was done against 20 mM-Tris+0.25 M NaCl+1 mM $MgCl_2$, pH=9.00 buffer or Dulbecco's phosphate buffered saline (DPBS).

K) Benzonase Treatment

The concentrated/diafiltrated virus solution was treated with Benzonase™ (American International Chemicals) at a concentration of 100 u/ml, room temperature overnight to reduce the contaminating nucleic acid concentration in the virus solution.

L) CsCl Gradient Ultracentrifugation

Crude virus solution was purified using double CsCl gradient ultracentrifugation using a SW40 rotor in a Beckman ultracentrifuge (XL-90). First, 7 ml of crude virus solution was overlaid on top of a step CsCl gradient made of equal volume of 2.5 ml of 1.25 g/ml and 1.40 g/ml CsCl solution, respectively. The CsCl gradient was centrifuged at 35,000 rpm for 1 hr at room temperature. The virus band at the gradient interface was recovered. The recovered virus was then further purified through a isopicnic CsCl gradient. This was done by mixing the virus solution with at least 1.5-fold volume of 1.33 g/ml CsCl solution. The CsCl solution was centrifuged at 35,000 rpm for at least 18 hr at room temperature. The lower band was recovered as the intact virus. The virus was immediately dialyzed against 20 mM Tris+1 mM $MgCl_2$, pH=7.50 buffer to remove CsCl. The dialyzed virus was stored at −70° C. for future use.

M) Ion Exchange Chromatography (IEC) Purification

The Benzonase treated virus solution was purified using IEC. Strong anionic resin Toyopearl SuperQ 650M (Tosohaas) was used for the purification. A FPLC system (Pharmacia) with a XK16 column (Pharmacia) were used for the initial method development. Further scale-up studies were carried out using a BioPilot system (Pharmacia) with a XK 50 column (Pharmacia). Briefly, the resin was packed into the columns and sanitized with 1 N NaOH, then charged with buffer B which was followed by conditioning with buffer A. Buffers A and B were composed of 20 mM Tris+0.25 M NaCl+1 mM $MgCl_2$, pH=9.00 and 20 mM Tris+2M NaCl+1 mM $MgCl_2$, pH=9.00, respectively. Viral solution sample was loaded onto the conditioned column, followed by washing the column with buffer A until the UV absorption reached base line. The purified virus was eluted from the column by using a 10 column volume of linear NaCl gradient.

A) HPLC Analysis

A HPLC analysis procedure was developed for evaluating the efficiency of virus production and purification. Tris(hydroxymethyl)aminomethane (tris) was obtained from Fisher-Biotech (Cat# BP154-1; Fair Lawn, N.J., U.S.A.); sodium chloride (NaCl) was obtained from Sigma (Cat# S-7653, St. Louis, Mo., U.S.A.). Both were used directly without further purification. HPLC analyses were performed on an Analytical Gradient System from Beckman, with Gold Workstation Software (126 binary pump and 168 diode array detector) equipped with an anion-exchange column from TosoHaas (7.5 cm×7.5 mm ID, 10 μm particle size, Cat# 18257). A 1-ml Resource Q (Pharmacia) anion-exchange column was used to evaluate the method developed by. Huyghe et al. using their HEPES buffer system. This method was only tried for the Bioreactor system.

The buffers used in the present HPLC system were Buffer A: 10 mM tris buffer, pH 9.0. Buffer. B: 1.5 M NaCl in buffer A, pH 9.0. The buffers were filtered through a 0.22 μm bottle top filter by Corning (Cat# 25970-33). All of the samples were filtered through a 0.8/0.22 μm Acrodisc PF from Gelman Sciences (Cat# 4187) before injection.

The sample is injected onto the HPLC column in a 60-100 μl volume. After injection, the column (TosoHaas) is washed with 20% B for 3 min at a flow rate of 0.75 ml/min. A gradient is then started, in which B is increased from 20% to 50% over 6 min. Then the gradient is changed from 50% to 100% B over 3 min, followed by 100% B for 6 min. The salt concentration is then changed back stepwise to 20% again over 4 min, and maintained at 20% B for another 6 min. The retention time of the Adp53 is 9.5±0.3 min with $A_{260}/A_{280} \cong 1.26 \pm 0.03$. Cleaning of the column after each chromatographic run is accomplished by injecting 100 μl of 0.15 M NaOH and then running the gradient.

Example 2

Effect of Medium Perfusion Rate in Cellcube™ on Virus Production and Purification For a perfusion cell culture system, such as the Cellcube™, medium perfusion rate plays an important role on the yield and quality of product. Two different medium perfusion strategies were examined. One strategy was to keep the glucose concentration in the Cellcube™ $\geq 2$ g/L (high perfusion rate). The other one was to keep the glucose concentration $\geq 1$ g/L (low medium perfusion rate).

No significant changes in the culture parameters, such as pH, DO, was observed between the two different perfusion rates. Approximately equivalent amount of crude viruses (before purification) were produced after harvesting using 1% Tween-20 lysis solution as shown in Table 5. However, dramatic difference was seen on the HPLC profiles of the viral solutions from the high and low medium perfusion rate production runs.

TABLE 5

Effect of medium glucose concentration on virus yield

| Glucose concentration (g/L) | $\geq 2.0$ | $\geq 1.0$ |
|---|---|---|
| Crude virus yield (PFU) | $4 \times 10^{12}$ | $4.9 \times 10^{12}$ |

Figure 1B:
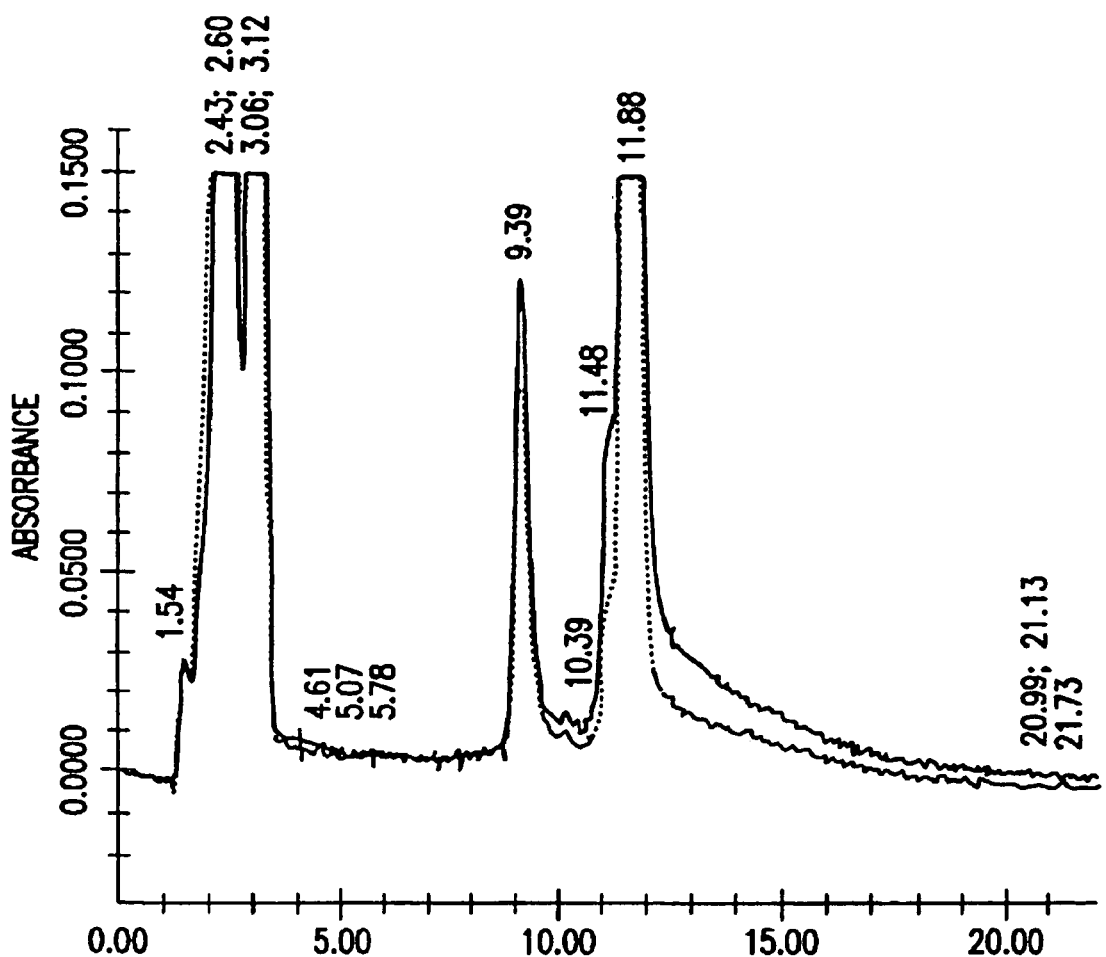

As shown in FIG. 1, a very well separated virus peak (retention time 9.39 min) was produced from viral solution using low medium perfusion rate. It was found that virus with adequate purity and biological activity was attained after a single step ion exchange chromatographic purification of the virus solution produced under low medium perfusion rate. On the other hand, no separated virus peak in the retention time of 9.39 min was observed from viral solution produced using high medium perfusion rate. This suggests that contaminants which have the same elution profile as the virus were produced under high medium perfusion rate. Although the nature of the contaminants is not yet clear, it is expected that the contaminants are related to the increased extracellular matrix protein production under high mediums perfusion rate (high serum feeding) from the producer cells. This poor separation characteristic seen on the HPLC created difficulties for process IEC purification as shown in the following Examples. As a result, medium perfusion rate used during the cell growth and the virus production phases in the Cellcube™ has a significant effect on the downstream IEC purification of the virus. Low medium perfusion rate is recommended. This not only produces easy to purify crude product but also offers more cost-effective production due to the reduced medium consumption.

Example 3

Methods of Cell Harvest and Lysis

Based on previous experience, the inventors first evaluated the freeze-thaw method. Cells were harvested from the Cellcube™ 45-48 hr post-infection. First, the Cellcube™ was isolated from the culture system and the spent medium was drained. Then, 50 mM EDTA solution was pumped into the Cube to detach the cells from the culture surface. The cell suspension thus obtained was centrifuged at 1,500 rpm (Beckman GS-6KR) for 10 min. The resultant cell pellet was resuspended in Dulbecco's phosphate buffered saline (DPBS). The cell suspension was subjected to 5 cycles of freeze/thaw between 37° C. water bath and dry-ice ethanol bath to release virus from the cells. The crude cell lysate (CCL) thus generated was analyzed on HPLC.

Figure 2:
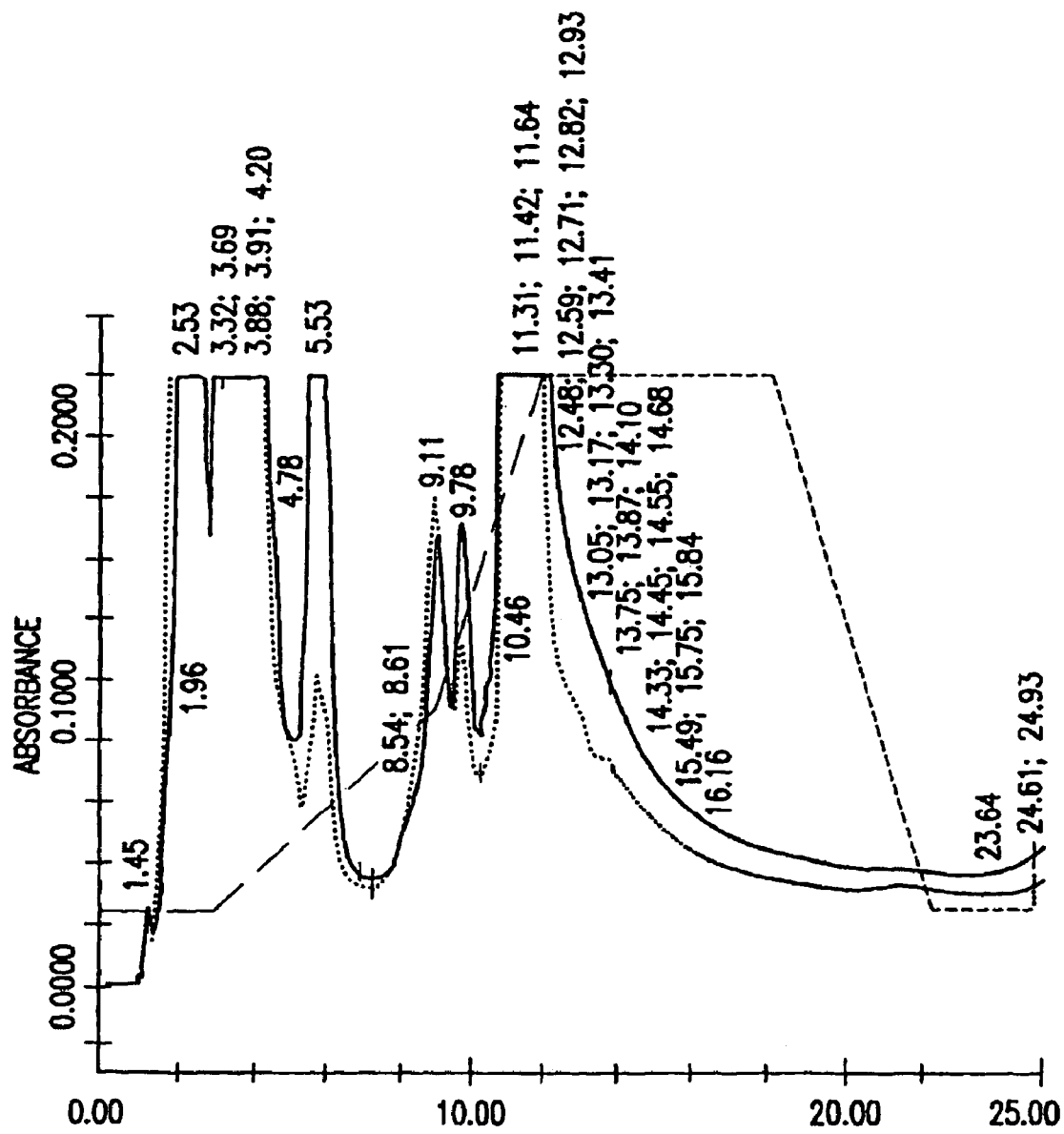
FIG. 2. The HPLC profile of crude cell lysate (CCL) from CellCube™ (solid line $A_{260}$; dotted line $A_{280}$).
Figure 3A:
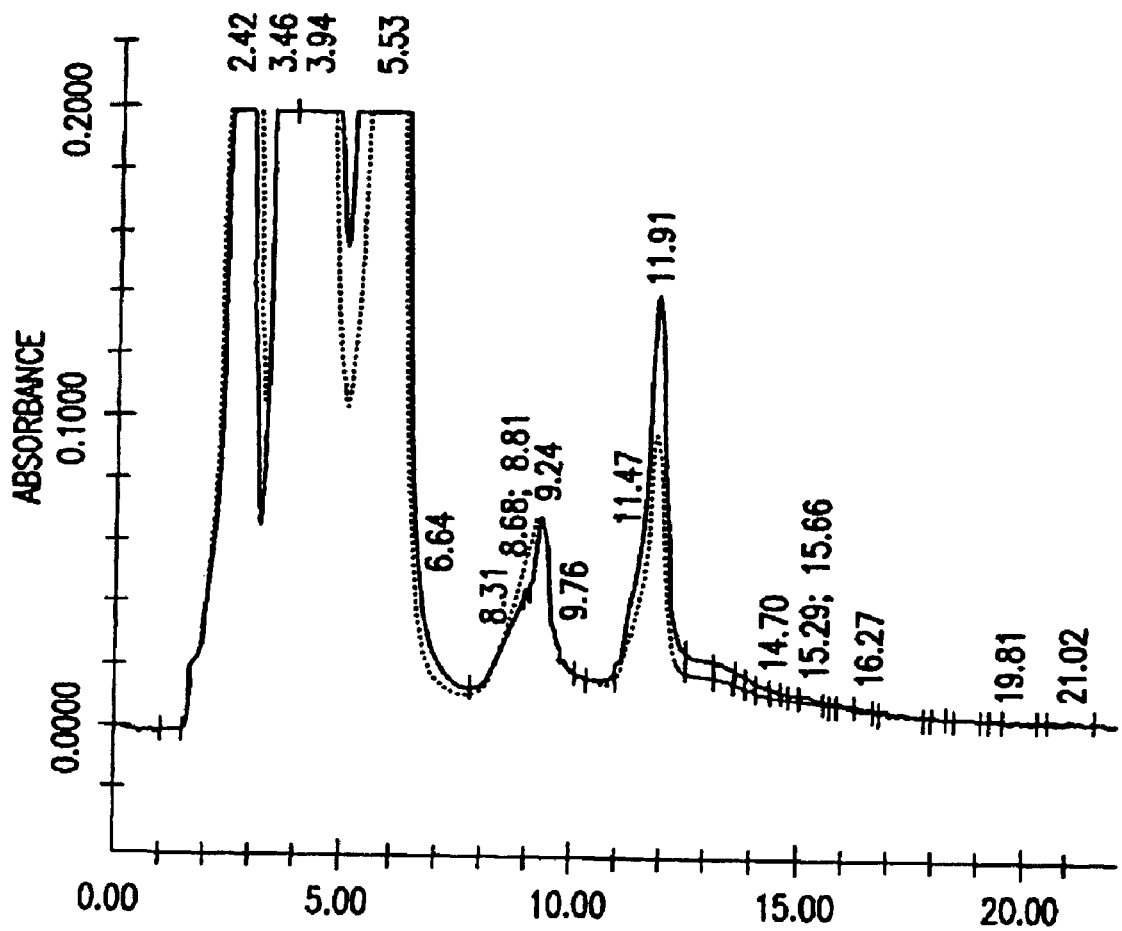
FIG. 3A, FIG. 3B, FIG. 3C, FIG. 3D and FIG. 3E. The HPLC profiles of lysis solutions from CellCube™ using different detergents.
Figure 3B:
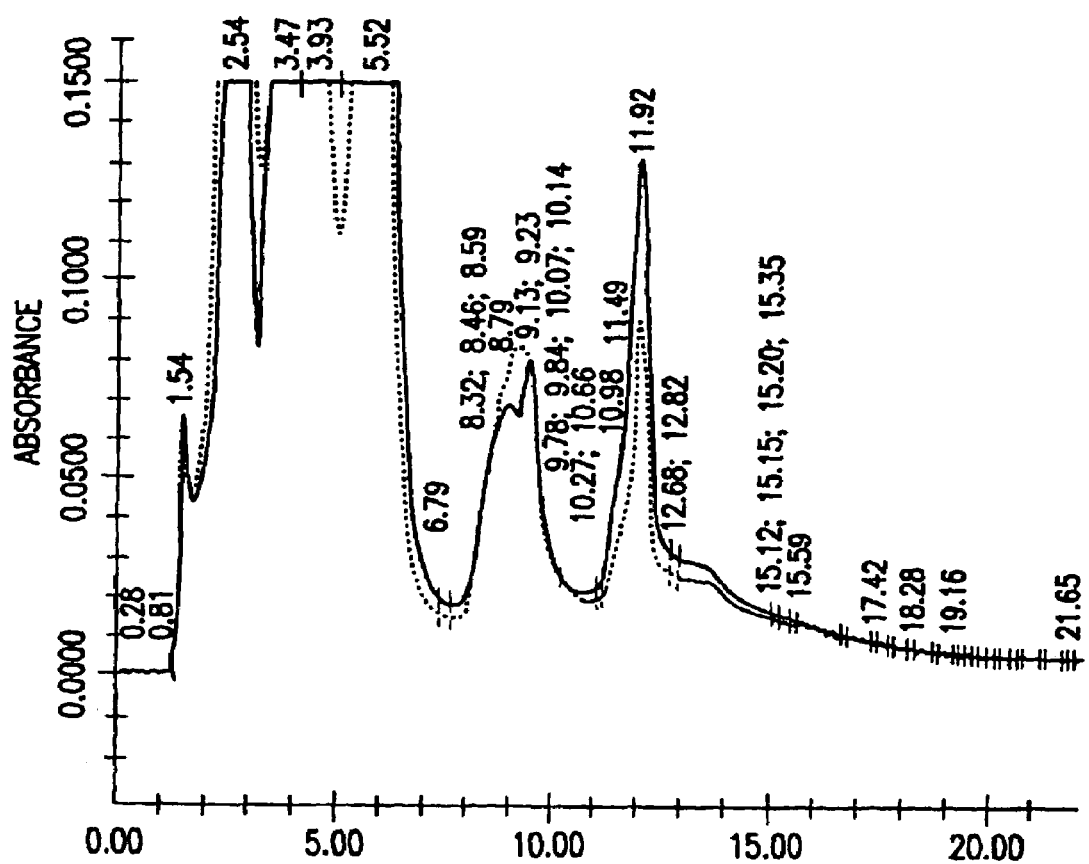
Figure 3C:
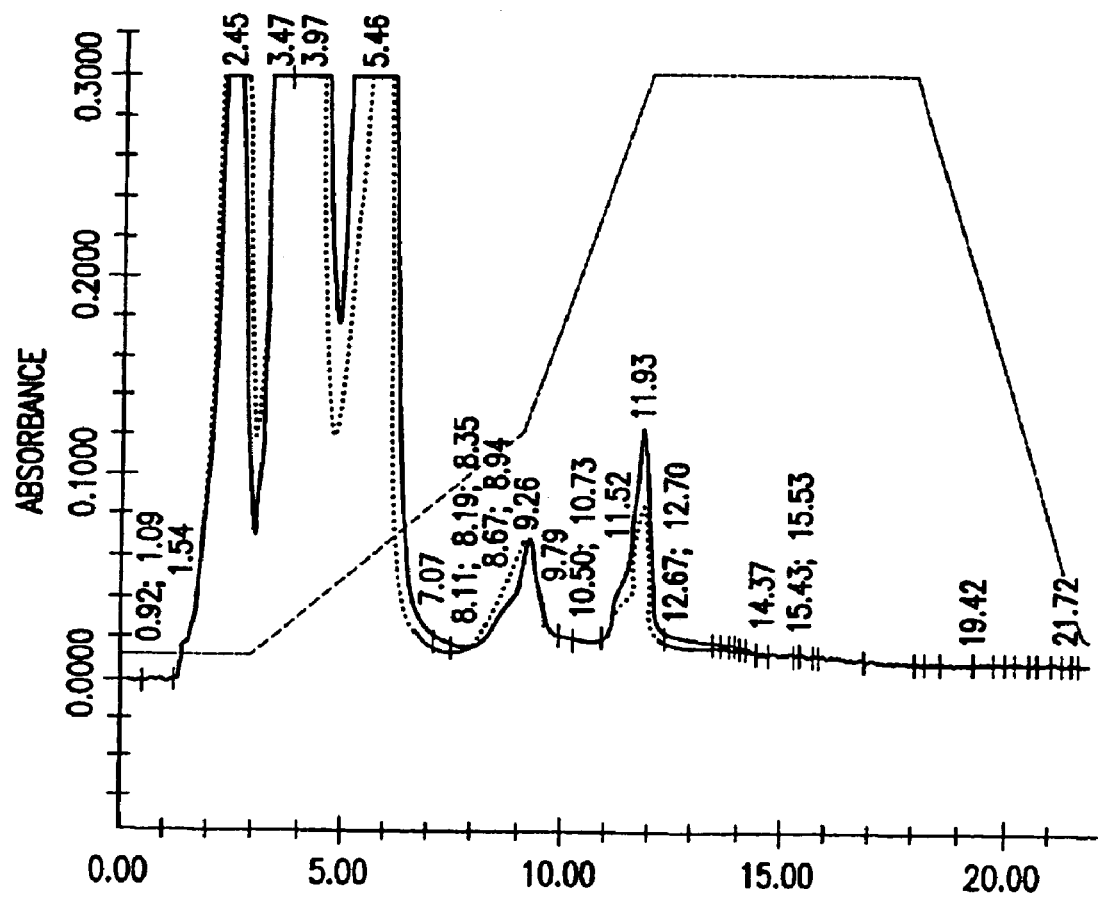
Figure 3D:
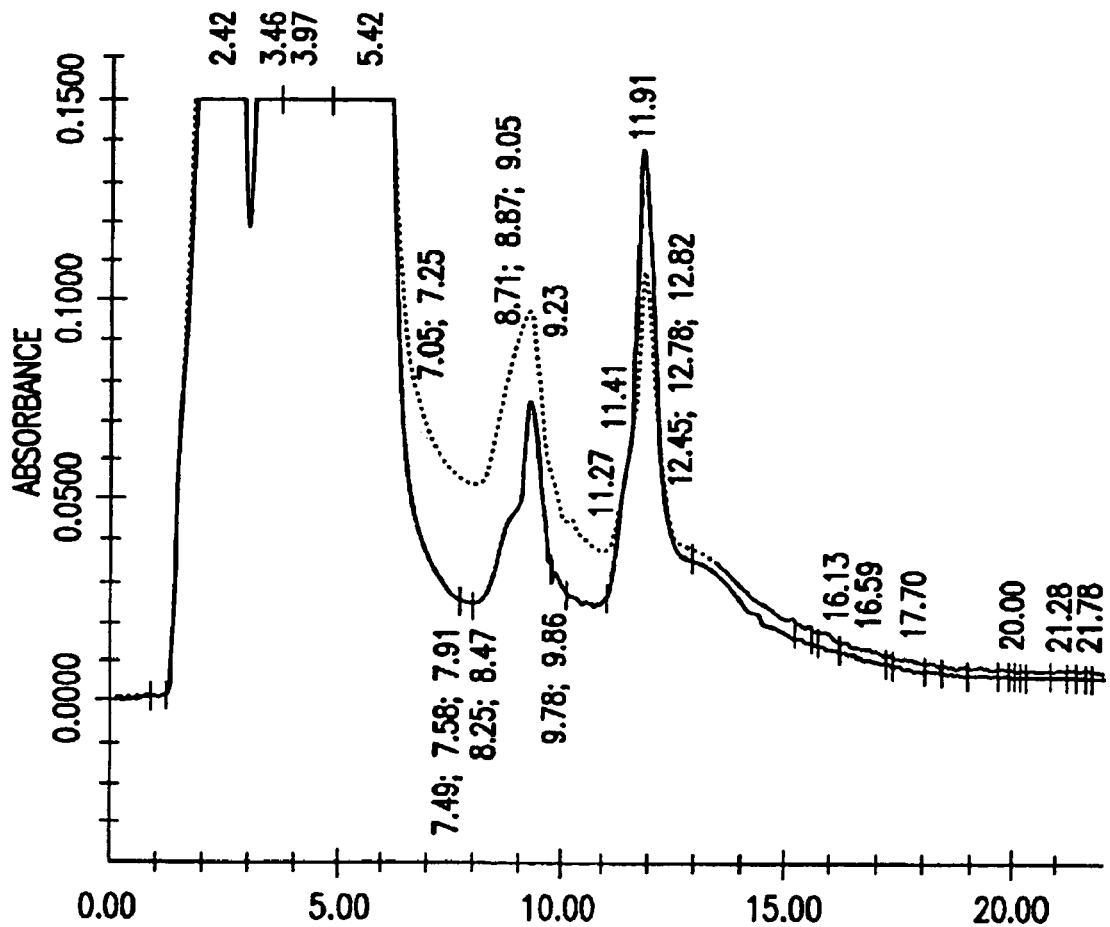
Figure 3E:
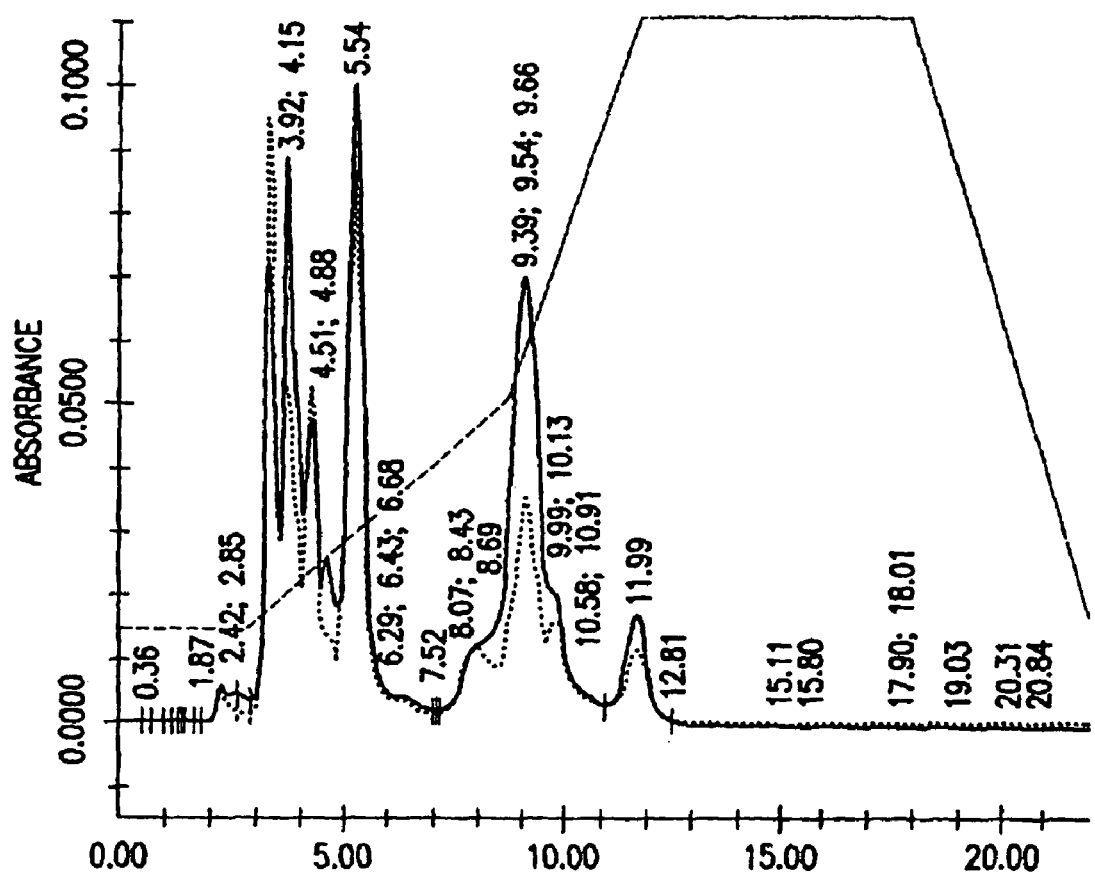

FIG. 2 shows the HPLC profile. No virus peak is observed at retention time of 9.32 min. Instead, two peaks at retention times of 9.11 and 9.78 min are produced. This profile suggests that the other contaminants having similar elution time as the virus exist in the CCL and interfere with the purification of the virus. As a result, very low purification efficiency was observed when the CCL was purified by IEC using FPLC.

In addition to the low purification efficiency, there was a significant product loss during the cell harvest step into the EDTA solution as indicated in Table 6. Approximately 20% of the product was lost into the EDTA solution which was discarded. In addition, about 24% of the crude virus product is present in the spent medium which was also discarded. Thus, only 56% of the crude virus product is in the CCL. Furthermore, freeze-thaw is a process of great variation and very limited scaleability. A more efficient cell lysis process with less product loss needed to be developed.

TABLE 6

Loss of virus during EDTA harvest of cells from Cellcube ™

| | Waste Spent Medium | EDTA harvest Solution | Crude product Crude cell lysate | Total crude product (PFU) |
|---|---|---|---|---|
| Volume (ml) | 2800 | 2000 | 82 | — |
| Titer (PFU/ml) | $2.6 \times 10^8$ | $3 \times 10^8$ | $2 \times 10^{10}$ | — |
| Total virus (PFU) | $7.2 \times 10^{11}$ | $6 \times 10^{11}$ | $1.64 \times 10^{12}$ | $3 \times 10^{12}$ |
| Percentage | 24% | 20% | 56% | |

Data was generated from 1 mer Cellcube ™.

TABLE 7

Evaluation of non-ionic detergents for cell lysis

| Detergents | Concentrations (w/v) | Chemistry | Comments |
|---|---|---|---|
| Thesit | 1% 0.5% 0.1% | Dodecylpoly(ethylene glycol ether)$_n$, n = 9-10 | Large Precipitate |
| NP-40 | 1% 0.5% 0.1% | Ethylphenolpoly (ethylene-glycolether)$_n$ n = 9-11 | Large precipitate |
| Tween-20 | 1% 0.5% 0.1% | Poly(oxyethylene)$_n$-sorbitan-monolaurate n = 20 | Small precipitate |
| Brij-58 | 1% 0.5% 0.1% | Cetylpoly (ethyleneglycolether)$_n$ n = 20 | Cloudy Solution |
| Triton X-100 | 1% 0.5% 0.1% | Octylphenolpoly(ethyleneglycolether)$_n$ n = 10 | Large precipitate |

Detergents have been used to lyse cells to release intracellular organelles. Consequently, the inventors evaluated the detergent lysis method for the release of adenovirus. Table 7 lists the 5 different non-ionic detergents that were evaluated for cell lysis. Cells were harvested from the Cellcube™ 48 hr post-infection using 50 mM EDTA. The cell pellet was resuspended in the different detergents at various concentrations listed in Table 7.

Cell lysis was carried out at either room temperature or on ice for 30 min. Clear lysis solution was obtained after centrifugation to remove the precipitate and cellular debris. The lysis solutions were treated with Benzonase and then analyzed by HPLC. FIG. 3 shows the HPLC profiles of lysis solutions from the different detergents. Thesit and NP-40 performed similarly as Triton X-100. Lysis solution generated from 1% Tween-20 gave the best virus resolution with the least virus resolution being observed with Brij-58. More efficient cell lysis was found at detergent concentration of 1% (w/v). Lysis temperature did not contribute significantly to the virus resolution under the detergent concentrations examined. For the purpose of process simplicity, lysis at room temperature is recommended. Lysis solution composed of 1% Tween-20 in 20 mM Tris+0.25M NaCl+1 mM MgCl$_2$, pH=7.50 was employed for cell lysis and virus harvest in the Cellcube™.

Example 4

Effects of Concentration/diafiltration on Virus Recovery

Virus solution from the lysis step was clarified and filtered before concentration/diafiltration. TFF membranes of different NMWCs, including 100K, 300K, 500K, and 1000K, were evaluated for efficient concentration/diafiltration. The highest medium flux with minimal virus loss to the filtrate was obtained with a membrane of 300K NMWC. Bigger NMWC membranes offered higher medium flux, but resulted in greater virus loss to the filtrate, while smaller NMWC membranes achieved an insufficient medium flux. Virus solution was first concentrated 10-fold, which was followed by 4 sample volumes of diafiltration against 20 mM Tris+0.25 M NaCl+1 mM MgCl$_2$, pH=9.00 buffer using the constant volume method. During the concentration/diafiltration process, pressure drop across the membrane was kept ≦5 psi. Consistent, high level virus recovery was demonstrated during the concentration/diafiltration step as indicated in Table 8.

TABLE 8

Concentration/diafiltration of crude virus solution

|  | Titer (PFU/ml) | | Volume (ml) | | Total virus (PFU) | | Recovery | |
| --- | --- | --- | --- | --- | --- | --- | --- | --- |
|  | Run #1 | Run #2 | Run #1 | Run #2 | Run #1 | Run #2 | Run #1 | Run #2 |
| Before conc./diafl. | $2.6 \times 10^9$ | $2 \times 10^9$ | 1900 | 2000 | $4.9 \times 10^{12}$ | $4 \times 10^{12}$ | | |
| Post conc./diafl. | $2.5 \times 10^{10}$ | $1.7 \times 10^{10}$ | 200 | 200 | $5 \times 10^{12}$ | $3.4 \times 10^{12}$ | 102% | 85% |
| Conc. Factor | | | 9.5 | 10 | | | | |
| Filtrate | $5 \times 10^5$ | $1 \times 10^6$ | 3000 | 3000 | $1.5 \times 10^9$ | $3 \times 10^9$ | | |

Example 5

Effect of Salt Addition on Benzonase Treatment

Virus solution after concentration/diafiltration was treated with Benzonase (nuclease) to reduce the concentration of contaminating nucleic acid in virus solution. Different working concentrations of Benzonase, which included 50, 100, 200, 300 units/ml, were evaluated for the reduction of nucleic acid concentrations. For the purpose of process simplicity, treatment was carried out at room temperature overnight. Significant reduction in contaminating nucleic acid that is hybridizable to human genomic DNA probe was seen after Benzonase treatment.

Figure 4A:
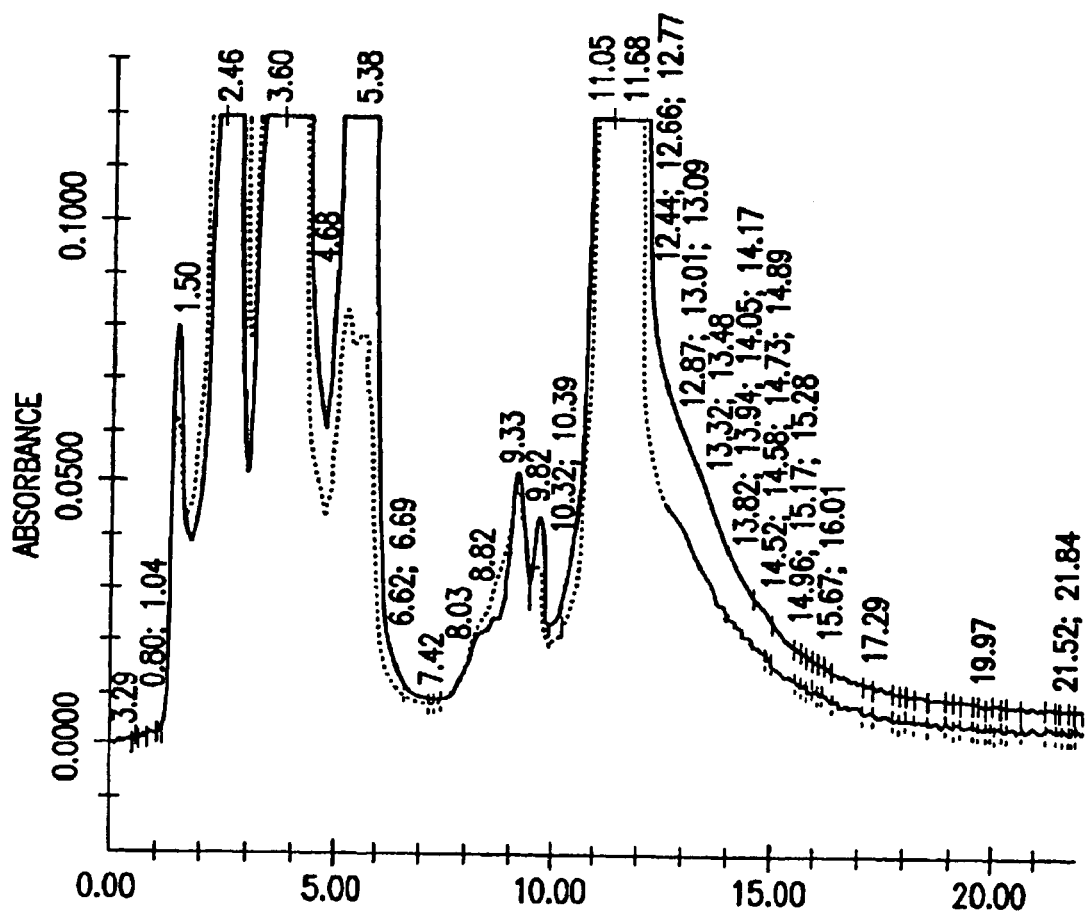
FIG. 4A and FIG. 4B. The HPLC profiles of virus solution before (FIG. 4A) and after (FIG. 4B) Benzonase treatment, (solid line $A_{260}$; dotted line $A_{280}$).
Figure 4B:
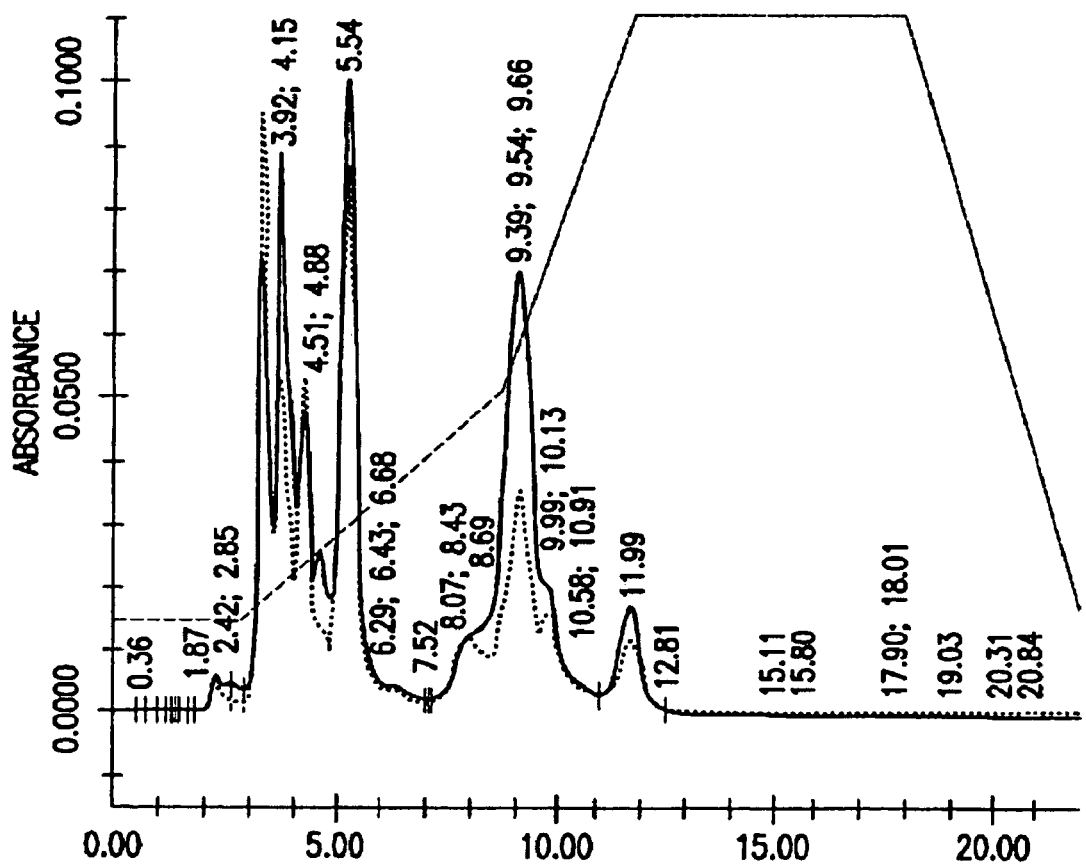

Table 9 shows the reduction of nucleic acid concentration before and after Benzonase treatment. Virus solution was analyzed on HPLC before and after Benzonase treatment. As shown in FIG. 4A and FIG. 4B, dramatic reduction in the contaminating nucleic acid peak was observed after Benzonase treatment. This is in agreement with the result of the nucleic acid hybridization assay. Because of the effectiveness, a Benzonase concentration of 100 u/ml was employed for the treatment of the crude virus solution.

TABLE 9

Reduction of contaminating nucleic acid concentration in virus solution

|  | Before Treatment | After Treatment | Reduction |
| --- | --- | --- | --- |
| Contaminating nucleic acid concentration | 200 µg/ml | 10 ng/ml | $2 \times 10^4$-fold |

Treatment condition: Benzonase concentration: 100 u/ml, temperature: room temperature, time: overnight.

Considerable change in the HPLC profile was observed, pre- and post-Benzonase treatment. No separated virus peak was detected at retention time of 9.33 min after Benzonase treatment. At the same time, a major peak with high 260 nm adsorption at retention time of 9.54 min was developed. Titer assay results indicated that Benzonase treatment did not negatively affect the virus titer and virus remained intact and infectious after Benzonase treatment. It was reasoned that cellular nucleic acid released during the cell lysis step interacted with virus and either formed aggregates with the virus or adsorbed onto the virus surface during Benzonase treatment.

Figure 5:
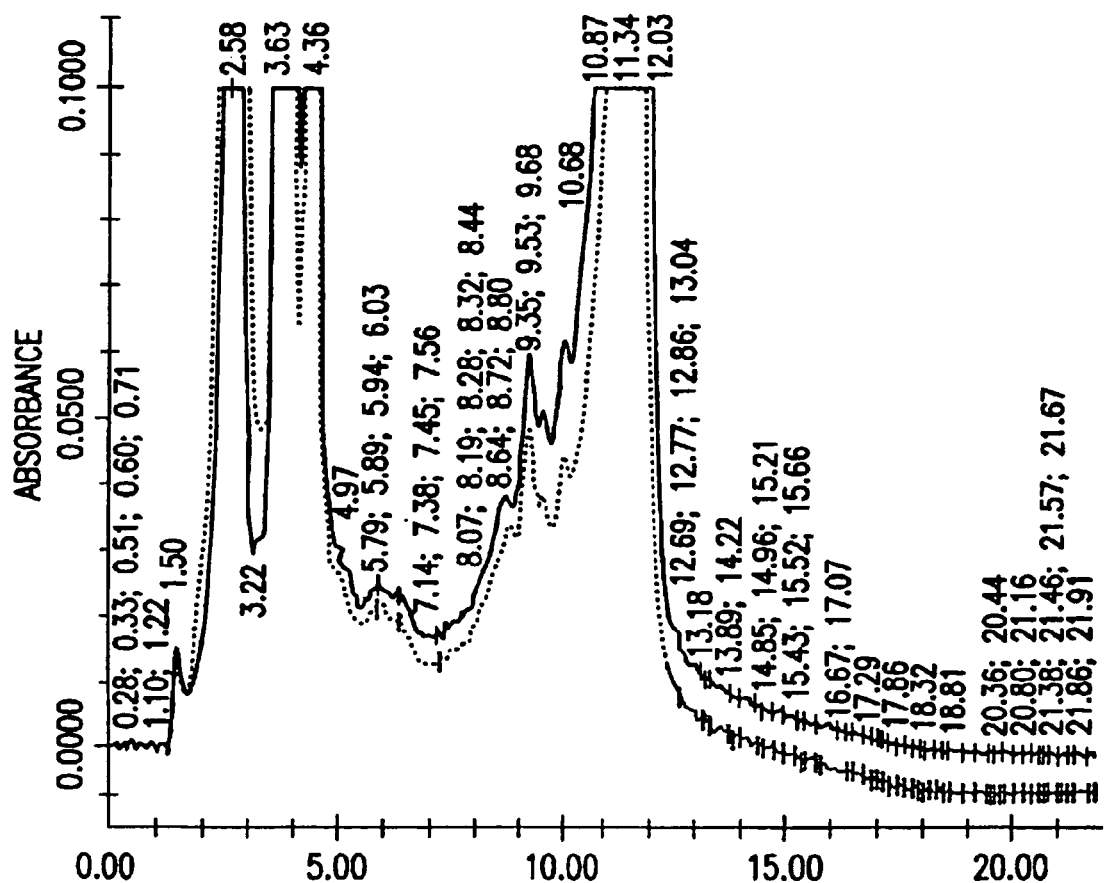
FIG. 5. The HPLC profile of virus solution after Benzonase treatment in the presence of 1 M NaCl. (solid line $A_{260}$; dotted line $A_{280}$).

To minimize the possible nucleic acid virus interaction during Benzonase treatment, different concentrations of NaCl was added into the virus solution before Benzonase treatment. No dramatic change in the HPLC profile occurred after Benzonase treatment in the presence of 1 M NaCl in the virus solution. FIG. 5 shows the HPLC profile of virus solution after Benzonase treatment in the presence of 1M NaCl. Unlike that shown in FIG. 4B, virus peak at retention time of 9.35 min still exists post Benzonase treatment. This result indicates that the presence of 1M NaCl prevents the interaction of nucleic acid with virus during Benzonase treatment and facilitates the further purification of virus from contaminating nucleic acid.

Example 6

Ion Exchange Chromatographic Purification

The presence of negative charge on the surface of adenovirus at physiological pH conditions prompted evaluation of anionic ion exchangers for adenovirus purification. The strong anionic ion exchanger Toyopearl Super Q 650M was used for the development of a purification method. The effects of NaCl concentration and pH of the loading buffer (buffer A) on virus purification was evaluated using the FPLC system.

A) Method Development

For ion exchange chromatography, buffer pH is one of the most important parameters and can have dramatic influence on the purification efficiency. In reference to the medium pH and conductivity used during virus production, the inventors formulated 20 mM Tris+1 mM $MgCl_2$+0.2M NaCl, pH=7.50 as buffer A. A XK16 column packed with Toyopearl SuperQ 650M with a height of 5 cm was conditioned with buffer A.

A sample of 5 ml of Benzonase treated concentrated/diafiltrated virus supernatant from the Celligen bioreactor was loaded onto the column. After washing the column, elution was carried out with a linear gradient of over 10 column volumes of buffer B formulation to reach mM Tris+1 mM $MgCl_2$+2M NaCl, pH=7.50.

Figure 6:
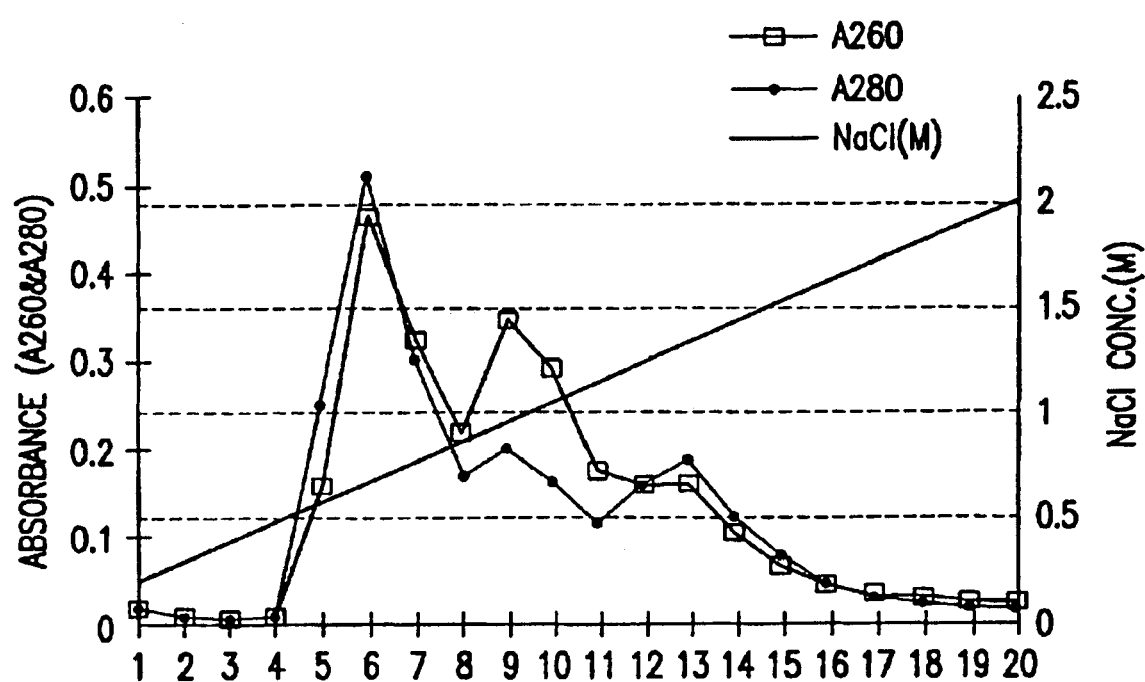
FIG. 6. Purification of AdCMVp53 virus under buffer A condition of 20 mM Tris +1 mM $MgCl_2$+0.2M NaCl, pH=7.5.
Figure 7:
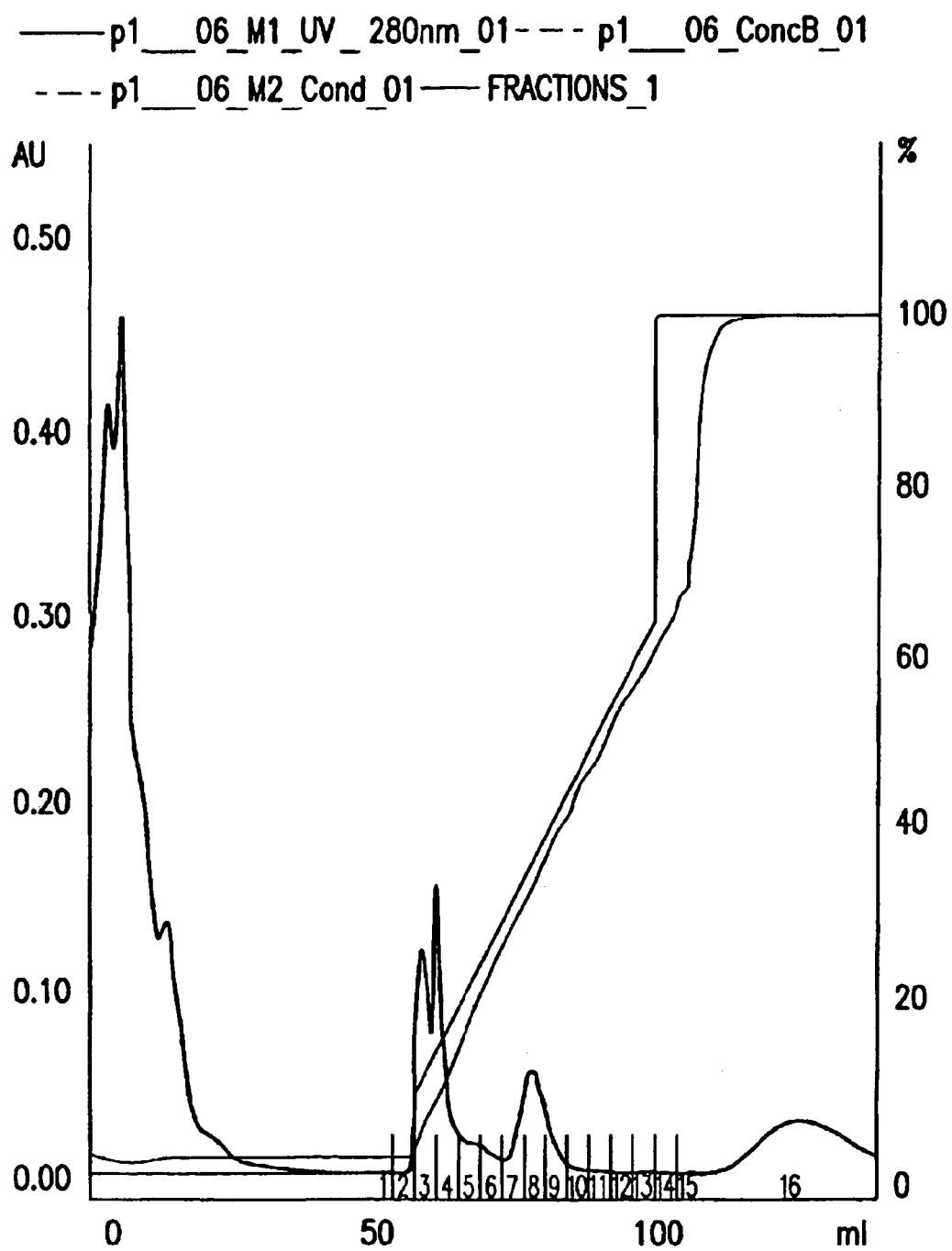
FIG. 7. Purification of AdCMVp53 virus under buffer A condition of 20 mM Tris+1 mM $MgCl_2$+0.2M NaCl, pH=9.0.

FIG. 6 shows the elution profile. Three peaks were observed during elution without satisfactory separation among them. Control study performed with 293 cell conditioned medium (with no virus) showed that the first two peaks are virus related. To further improve the separation efficiency, the effect of buffer pH was evaluated. Buffer pH was increased to 9.00 while keeping other conditions constant. Much improved separation, as shown in FIG. 7, was observed as compared to that of buffer pH of 7.50. Fractions #3, #4, and #8 were analyzed on HPLC.

Figure 8A:
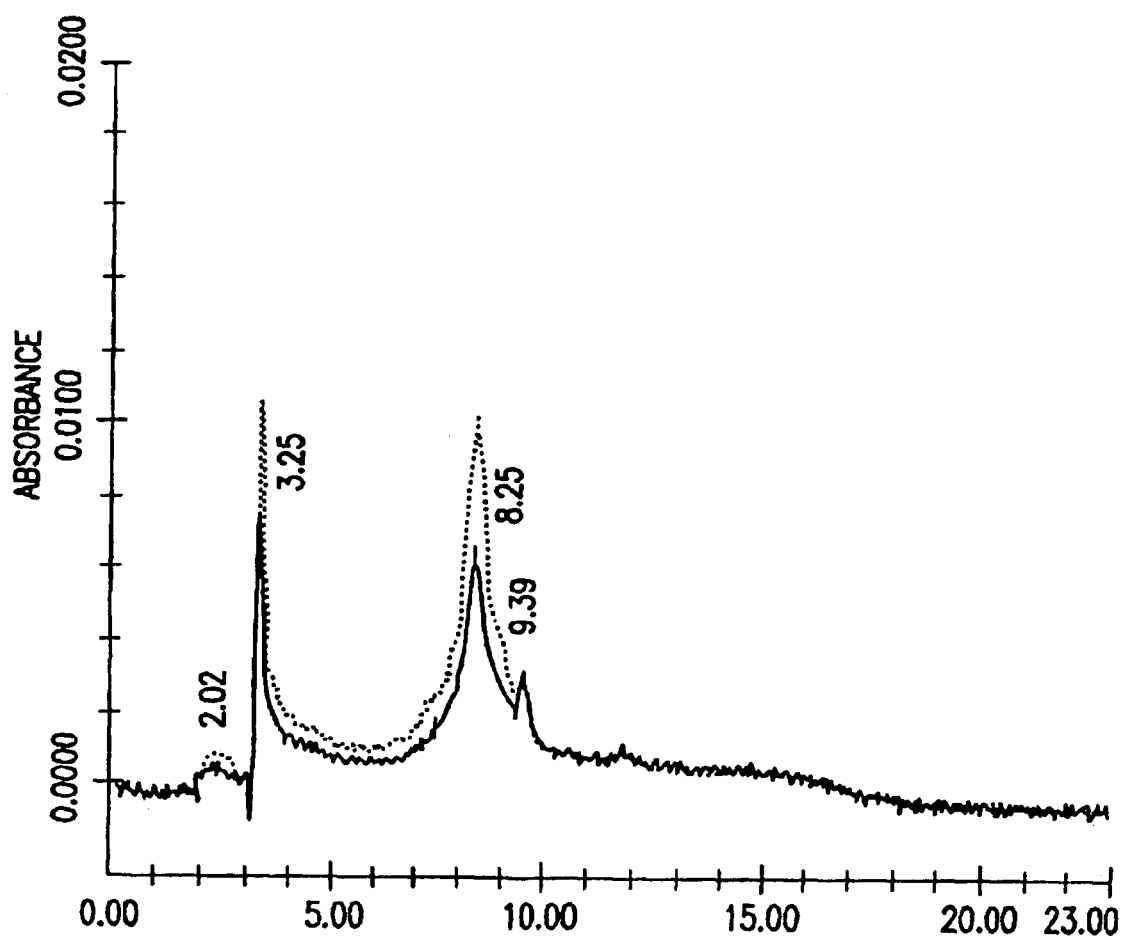
FIG. 8A, FIG. 8B, and FIG. 8C. HPLC analysis of fractions obtained during purification FIG. 8A fraction 3.
Figure 8B:
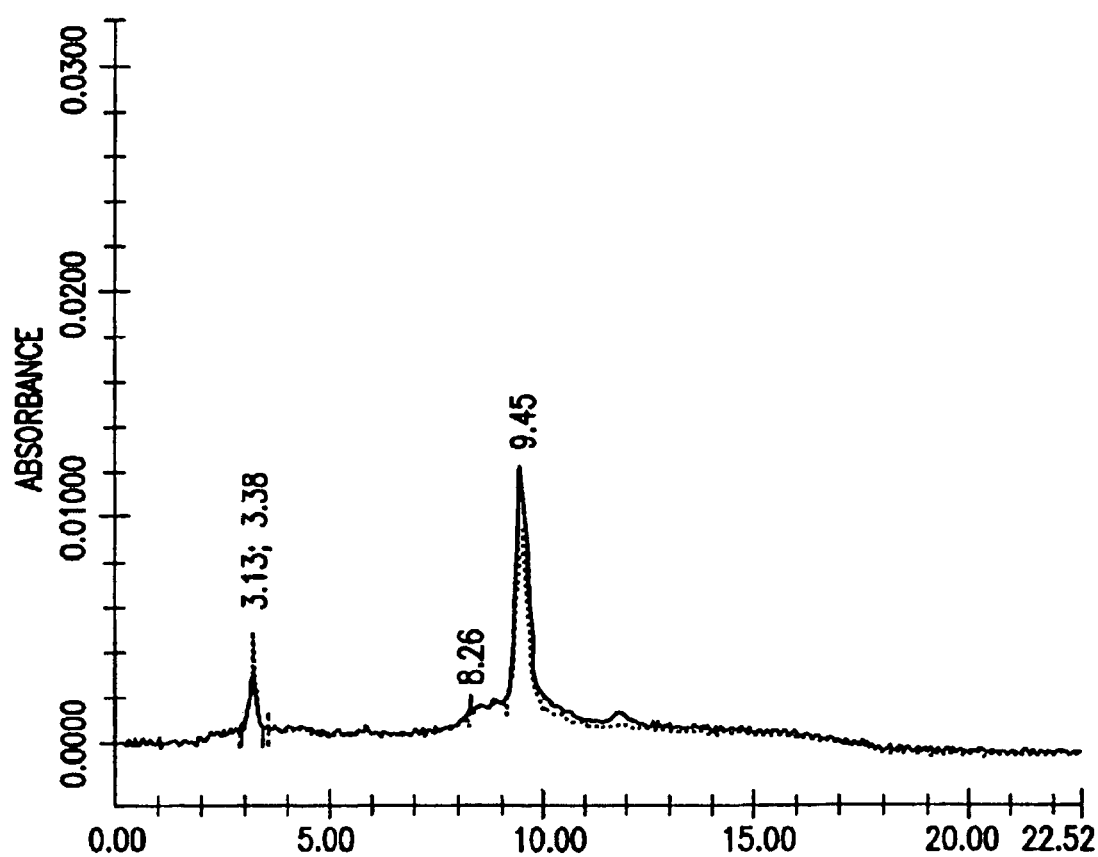
Figure 8C:
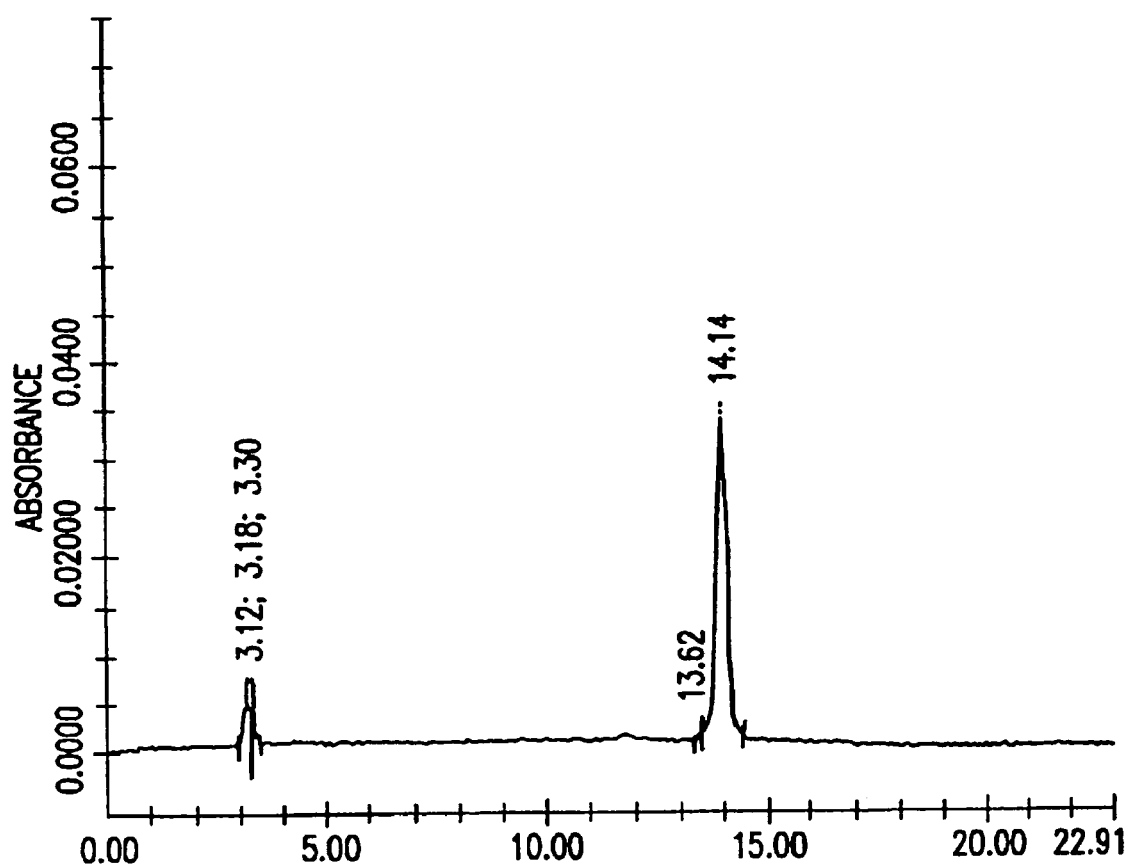

As shown in FIG. 8, the majority of virus was found in fraction #4, with no virus being detected in fractions #3 and #8. Fraction #8 was found to be mainly composed of contaminating nucleic acid. However, the purification was still not optimal. There is overlap between fractions #3 and #4 with contaminants still detected in fraction #4.

Figure 9:
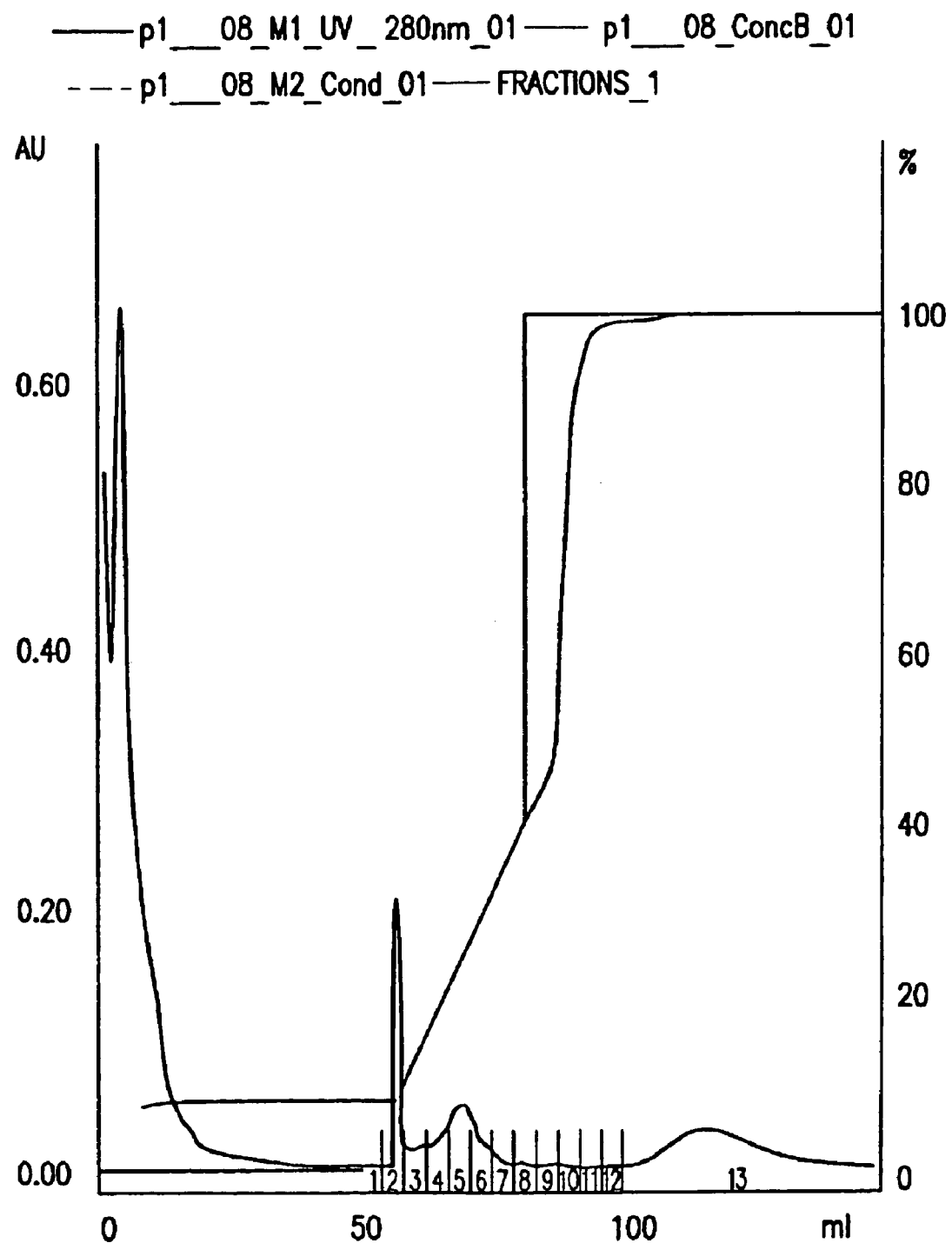
FIG. 9. Purification of AdCMVp53 virus under buffer A condition of 20 mM Tris+1 mM $MgCl_2$+0.3M NaCl, pH=9.
Figure 10A:
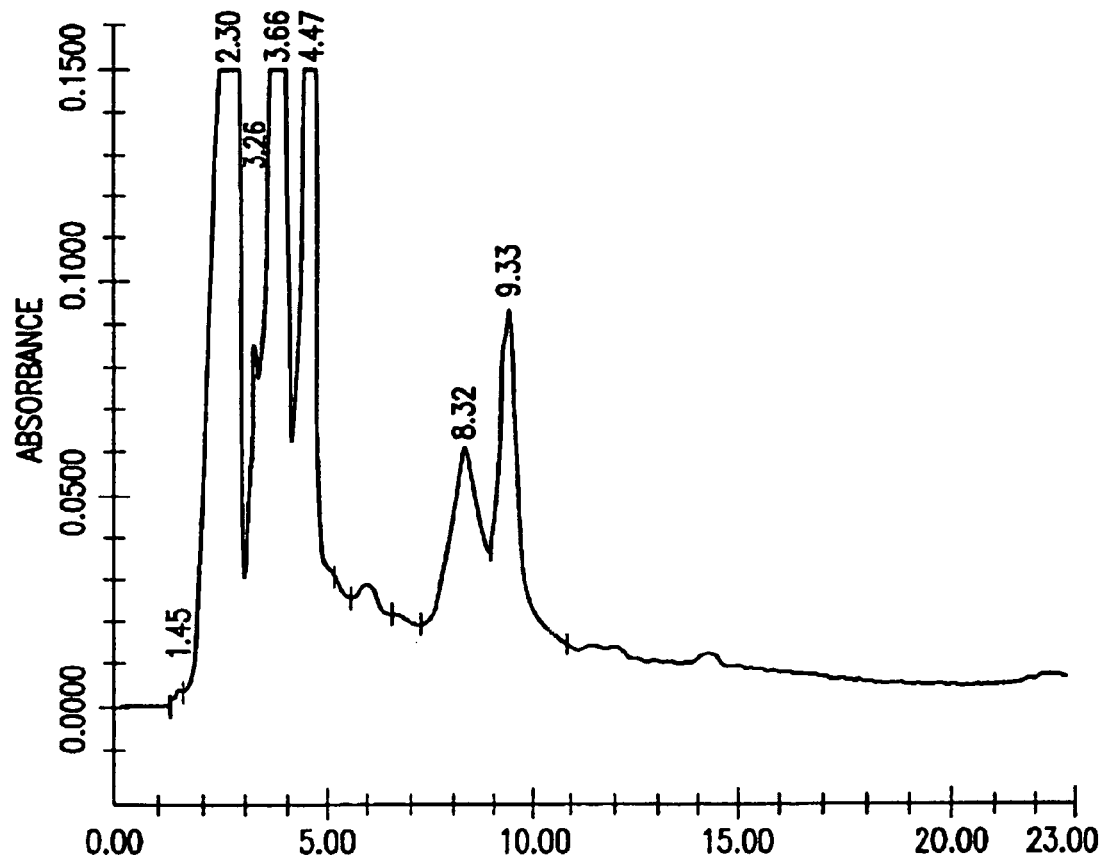
FIG. 10A, FIG. 10B, FIG. 10C, FIG. 10D and FIG. 10E. HPLC analysis of crude virus fractions obtained during purification and CsCl gradient purified virus.
Figure 10B:
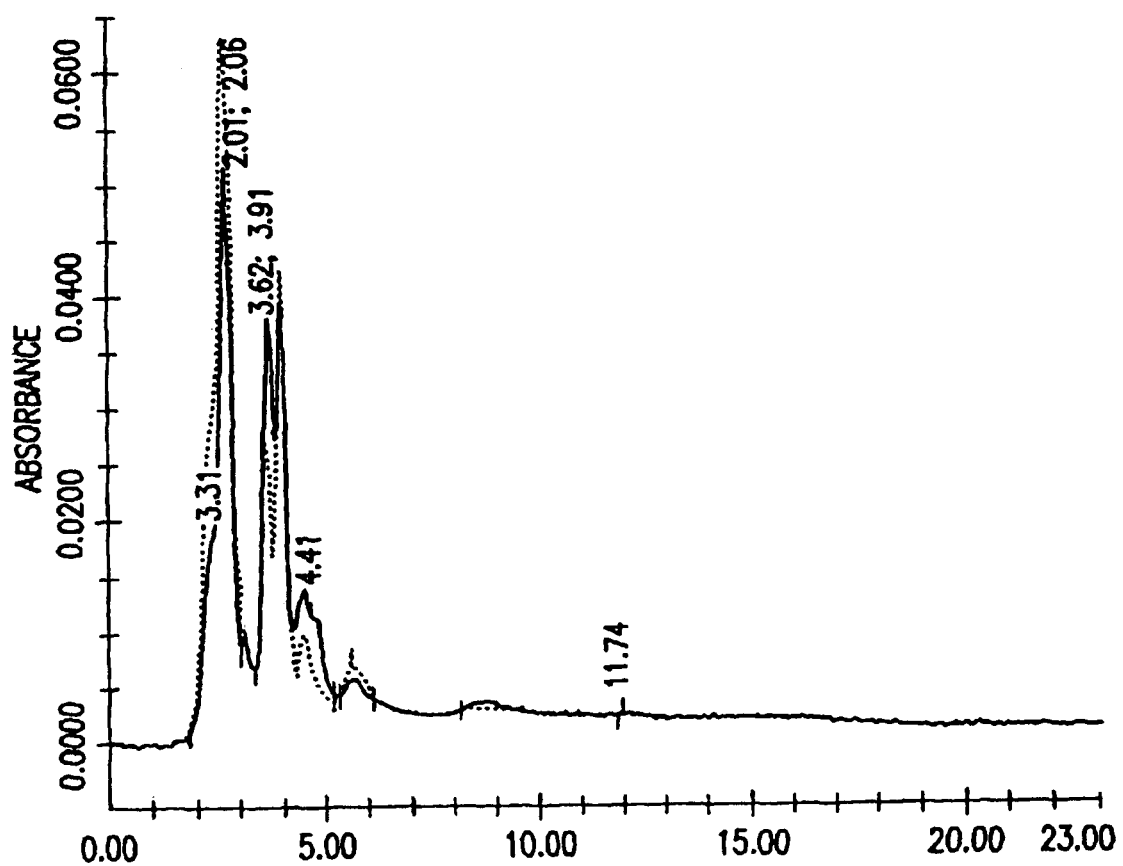
Figure 10C:
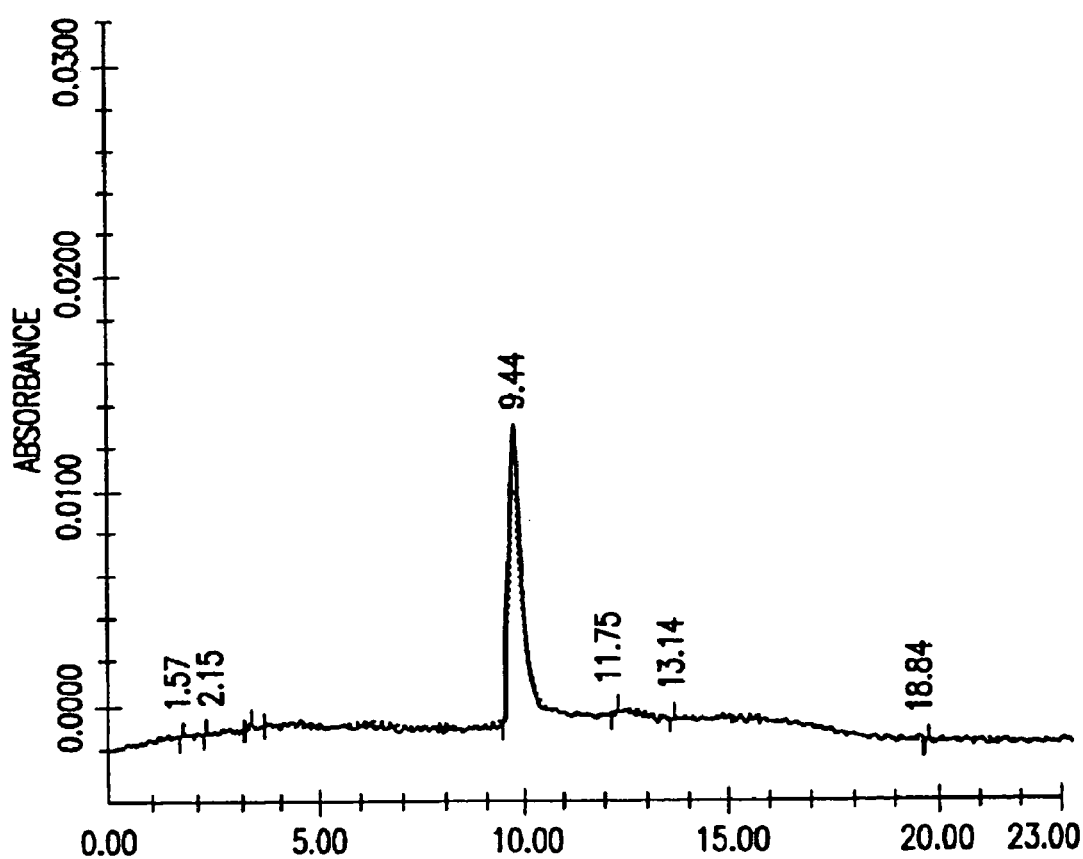
Figure 10D:
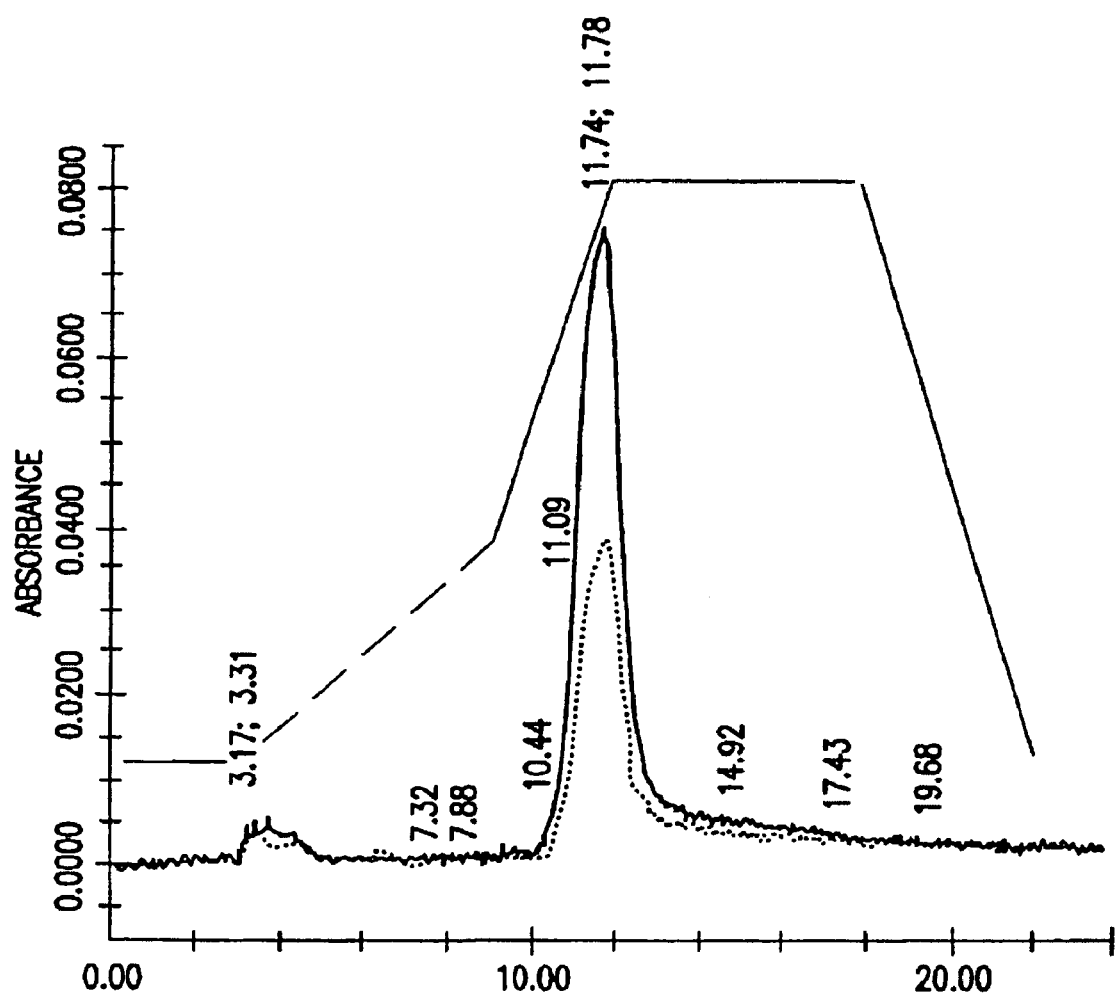
Figure 10E:
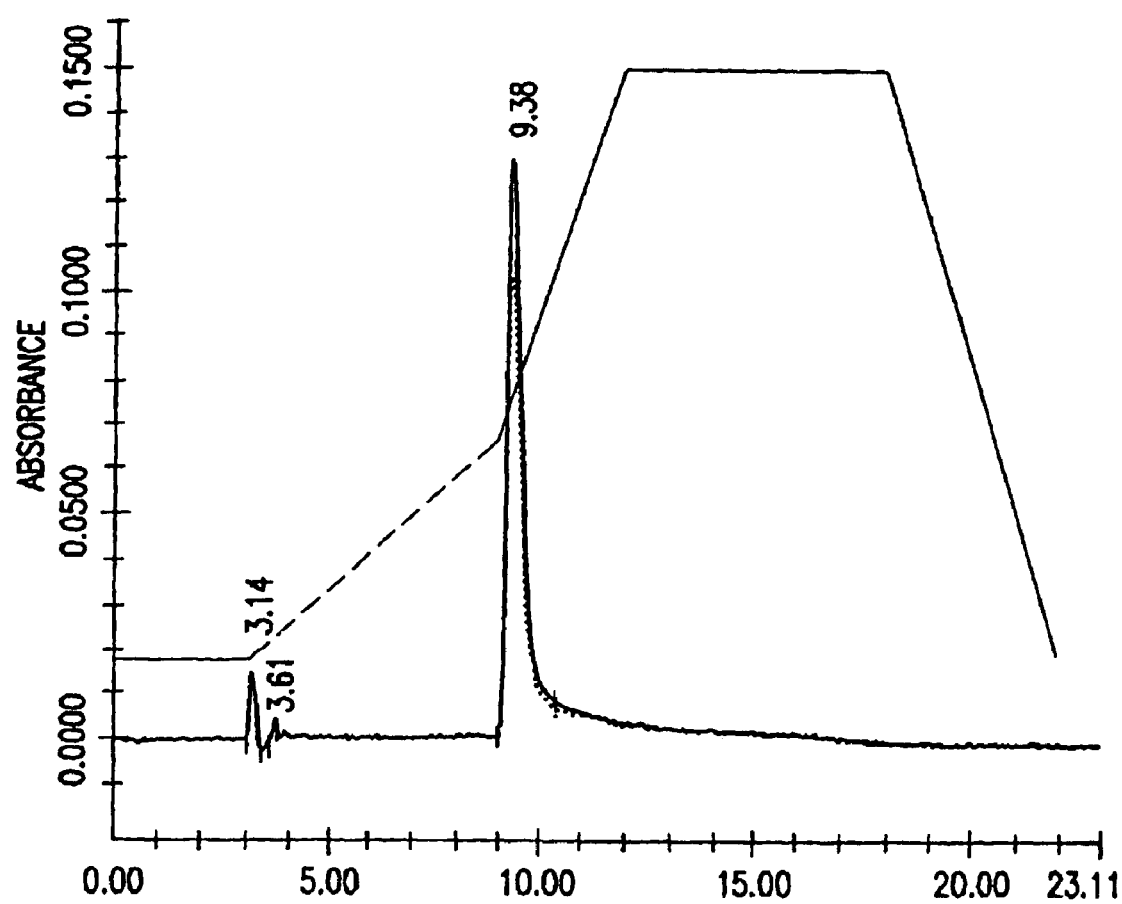

Based on the chromatogram in FIG. 7, it was inferred that further improvement of virus purification could be achieved by increasing the salt concentration in buffer A. As a result, the contaminants present in the fraction #3, which is prior to the virus peak, can be shifted to the flow through faction. The NaCl concentration in buffer A was increased to 0.3 M while keeping other conditions constant. FIG. 9 shows the elution profile under the condition of 0.3 M NaCl in buffer A.

Dramatic improvement in purification efficiency was achieved. As expected the contaminant peak observed in FIG. 7 was eliminated under the increased salt condition. Samples from crude virus sup, flow through, peak #1, and peak #2 were analyzed on HPLC and the results are shown in FIG. 10. No virus was detected in the flow through fraction. The majority of the contaminants present in the crude material were found in the flow through. HPLC analysis of peak #1 showed a single well defined virus peak. This HPLC profile is equivalent to that obtained from double CsCl gradient purified virus. Peaks observed at retention times of 3.14 and 3.61 min in CsCl gradient purified virus are glycerol related peaks. The purified virus has a A260/A280 ratio of 1.27±0.03. This similar to the value of double CsCl gradient purified virus as well as the results reported by Huyghe et al. (1996). Peak #2 is composed mainly of contaminating nucleic acid. Based on the purification result, the inventors proposed the following method for IEC purification of adenovirus sup from the bioreactor.

Buffer A: 20 mM Tris+1 mM MgCl$_2$+0.3M NaCl, pH=9.00

Buffer B: 20 mM Tris+1 mM MgCl$_2$+2M NaCl, pH=9.00

Elution: 10 column volume linear gradient

B) Method Scale-Up

Figure 11:
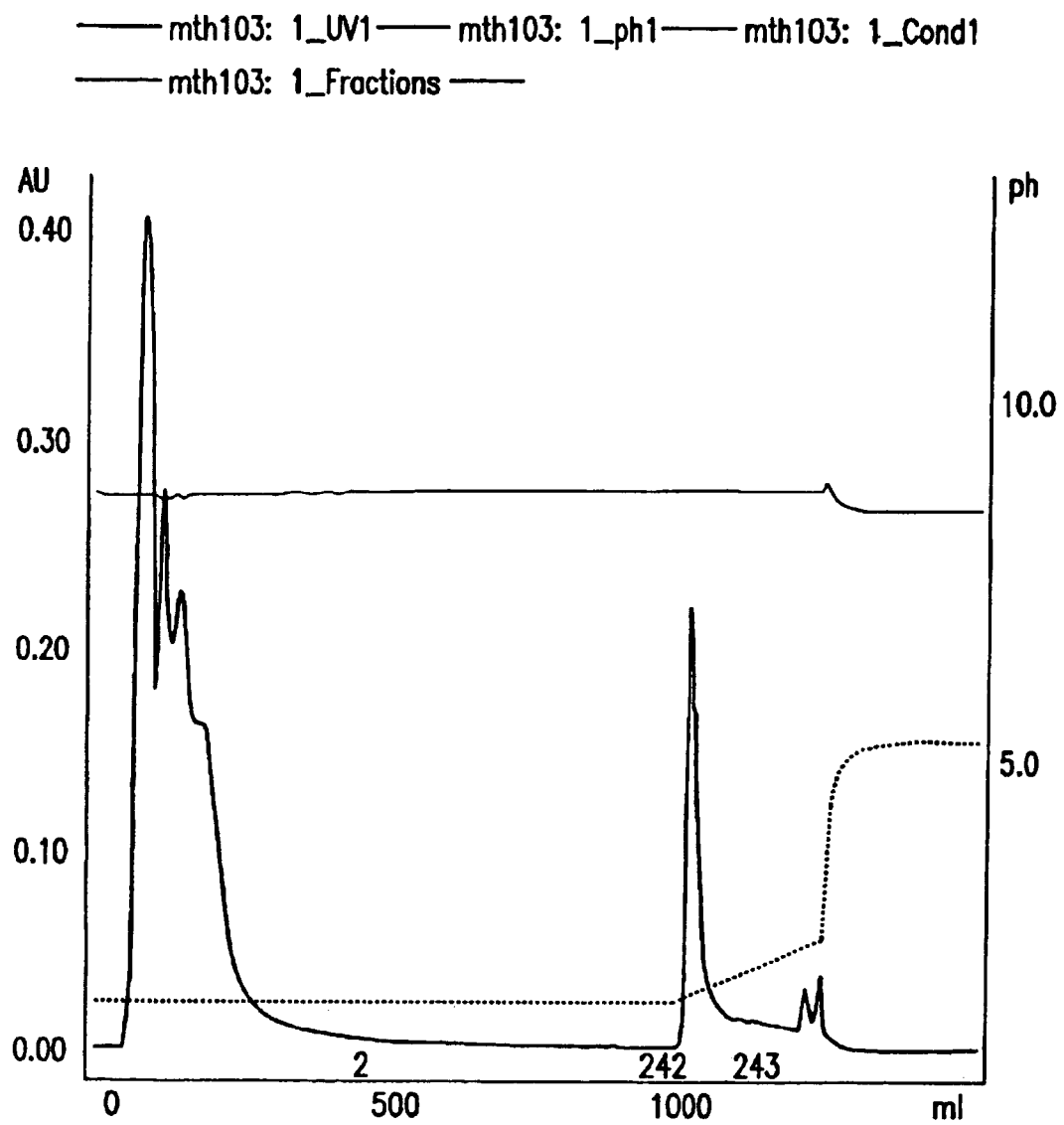
FIG. 11. HPLC purification profile from a 5 cm id column.

Following the development of the method, purification was scaled-up from the XK16 column (1.6 cm I.D.) to a XK50 column (5 cm I.D., 10-fold scale-up) using the same purification method. A similar elution profile was achieved on the XK50 column as shown in FIG. 11. The virus fraction was analyzed on HPLC, which indicated equivalent virus purity to that obtained from the XK16 column.

During the scale-up studies, it was found that it was more convenient and consistent to use conductivity to quantify the salt concentration in buffer A. The optimal conductivity of buffer A is in the range of 25±2 mS/cm at approximately room temperature (21° C.). Samples produced during the purification process together with double CsCl purified virus were analyzed on SDS-PAGE.

Figure 12:
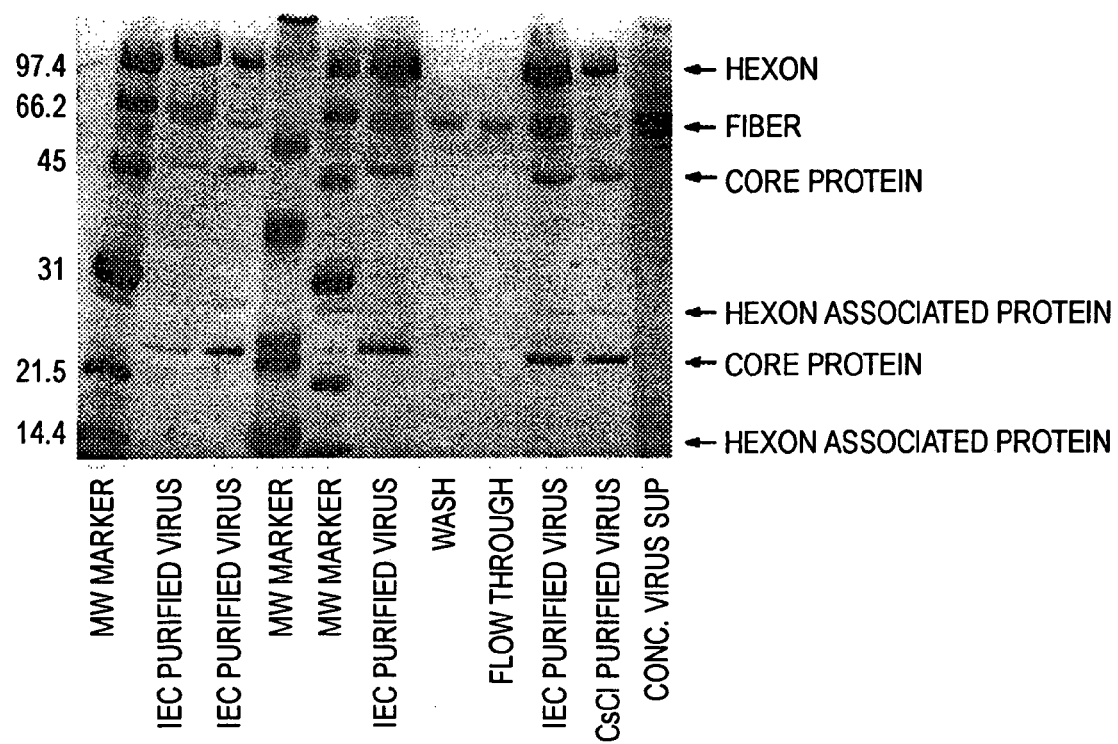
FIG. 12. The major adenovirus structure proteins detected on SDS-PAGE.
Figure 13:
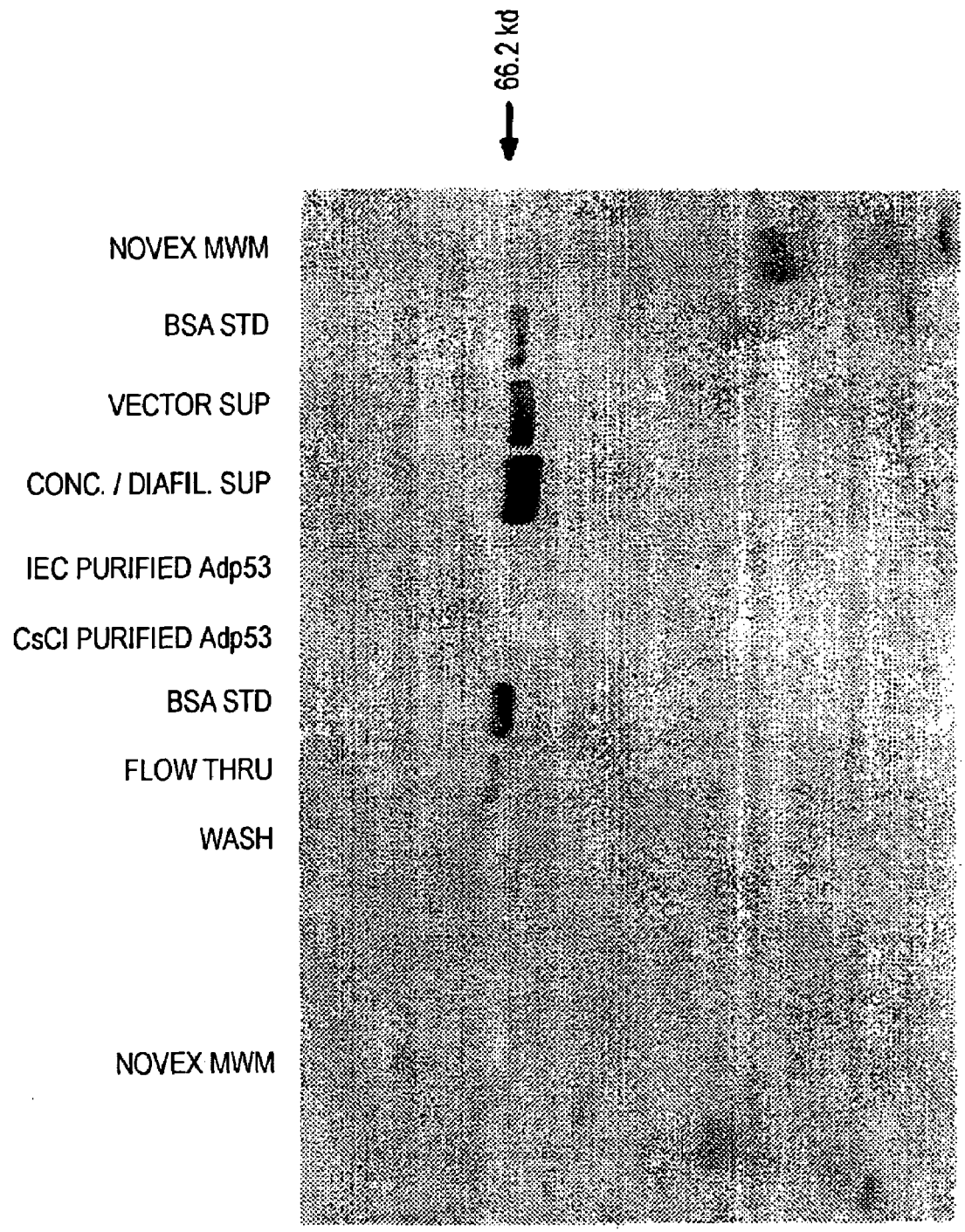
FIG. 13. The BSA concentration in the purified virus as detected level of the western blot assay.

As shown in FIG. 12, all the major adenovirus structure proteins are detected on the SDS-PAGE. The IEC purified virus shows equivalent staining as that of the double CsCl purified virus. Significant reduction in bovine serum albumin (BSA) concentration was achieved during purification. The BSA concentration in the purified virus was below the detection level of the western blot assay as shown in FIG. 13.

The reduction of contaminating nucleic acid concentration in virus solution during the purification process was determined using nucleic acid slot blot. $^{32}$P labeled human genomic DNA was used as the hybridization probe (because 293 cells are human embryonic kidney cells). Table 10 shows the nucleic acid concentration at different stages of the purification process. Nucleic acid concentration in the final purified virus solution was reduced to 60 pg/ml, an approximate 3.6×10$^6$-fold reduction compared to the initial virus supernatant. Virus titer and infectious to total particle ratio were determined for the purified virus and the results were compared to that from double CsCl purification in Table 9. Both virus recovery and particle/PFU ratio are very similar between the two purification methods. The titer of the column purified virus solution can be further increased by performing a concentration step.

TABLE 10

Removal of contaminating nucleic acids during purification

| Steps during purification | Contaminating nucleic acid concentration |
|---|---|
| Virus supernatant from bioreactor | 220 µg/ml |
| Concentrated/diafiltrated sup | 190 µg/ml |
| Sup post Benzonase treatment (O/N, RT, 100 u/ml) | 10 ng/ml |
| Purified virus from column | 210 pg/ml |
| Purified virus post concentration/diafiltration | 60 pg/ml |
| CsCl purified virus | 800 pg/ml |

Example 7

Other Purification Methods

In addition to the strong anionic ion exchange chromatography, other modes of chromatographic methods, were also evaluated for the purification of AdCMVp53 virus (e.g. size exclusion chromatography, hydrophobic interaction chromatography, cation exchange chromatography, or metal ion affinity chromatography). Compared to the Toyopearl Super Q, all those modes of purification offered much less efficient purification with low product recovery. Therefore, Toyopearl Super Q resin is recommended for the purification of AdCMVp53. However, other quaternary ammonium chemistry based strong anionic exchangers are likely to be suitable for the purification of AdCMVp53 with some process modifications.

Example 8

Purification of Crude AdCMVp53 Virus Generated from Cellcube™

Two different production methods were developed to produce AdCMVp53 virus. One was based on microcarrier culture in a stirred tank bioreactor. The other was based on a Cellcube™ bioreactor. As described above, the purification method was developed using crude virus supernatant generated from the stirred tank bioreactor. It was realized that although the same medium, cells and viruses were used for virus production in both the bioreactor and the Cellcube™, the culture surface onto which cells attached was different.

In the bioreactor, cells were grown on a glass coated microcarrier, while in the Cellcube™ cells were grown on proprietary treated polystyrene culture surface. Constant medium perfusion was used in the Cellcube™, on the other hand, no medium perfusion was used in the bioreactor. In the Cellcube™, the crude virus product was harvested in the form of virally infected cells, which is different from the virus supernatant harvested from the bioreactor.

Figure 14:
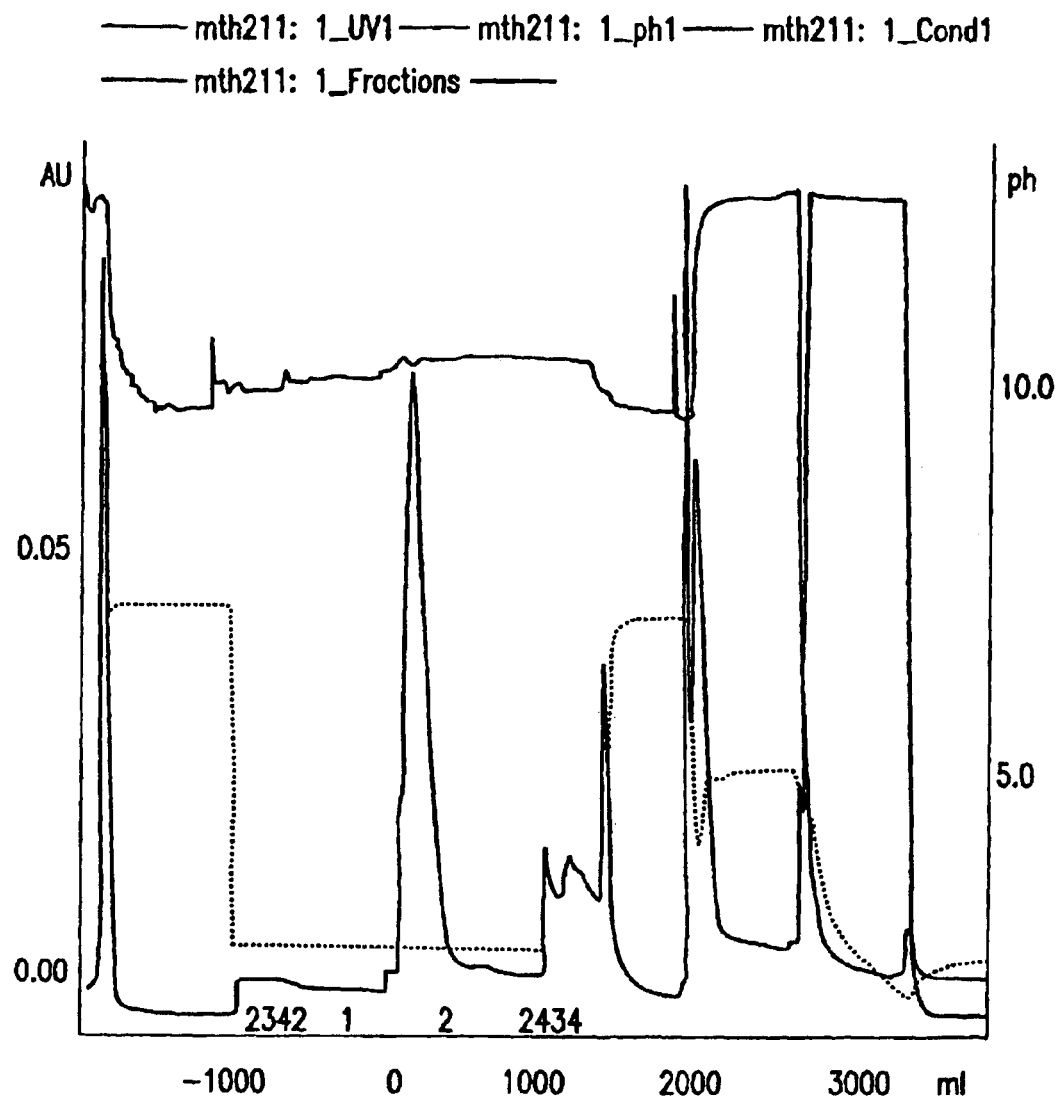
FIG. 14. The chromatogram for the crude cell lysate material generated from the CellCube™.

Crude cell lysate (CCL), produced after 5 cycles freeze-thaw of the harvested virally infected cells, was purified by IEC using the above described method. Unlike the virus supernatant from the bioreactor, no satisfactory purification was achieved for the CCL material generated from the Cellcube™. FIG. 14 shows the chromatogram. The result suggests that crude virus solution generated from the Cellcube™ by freeze-thawing harvested cells is not readily purified by the IEC method.

Other purification methods, including hydrophobic interaction and metal chelate chromatography, were examined for the purification of virus in CCL. Unfortunately, no improvement in purification was observed by either method. Considering the difficulties of purification of virus in CCL and the disadvantages associated with a freeze-thaw step in the production process, the inventors decided to explore other cell lysis methods.

A) Purification of Crude Virus Solution in Lysis Buffer

As described in Examples 1 and 3, HPLC analysis was used to screen different detergent lysis methods. Based on the HPLC results, 1% Tween-20 in 20 mM Tris+0.25 M NaCl+1 mM $MgCl_2$, pH=7.50 buffer was employed as the lysis buffer. At the end of the virus production phase, instead of harvesting the infected cells, the lysis buffer was pumped into the Cellcube™ after draining the spent medium. Cells were lysed and virus released into the lysis buffer by incubating for 30 min.

Figure 15:
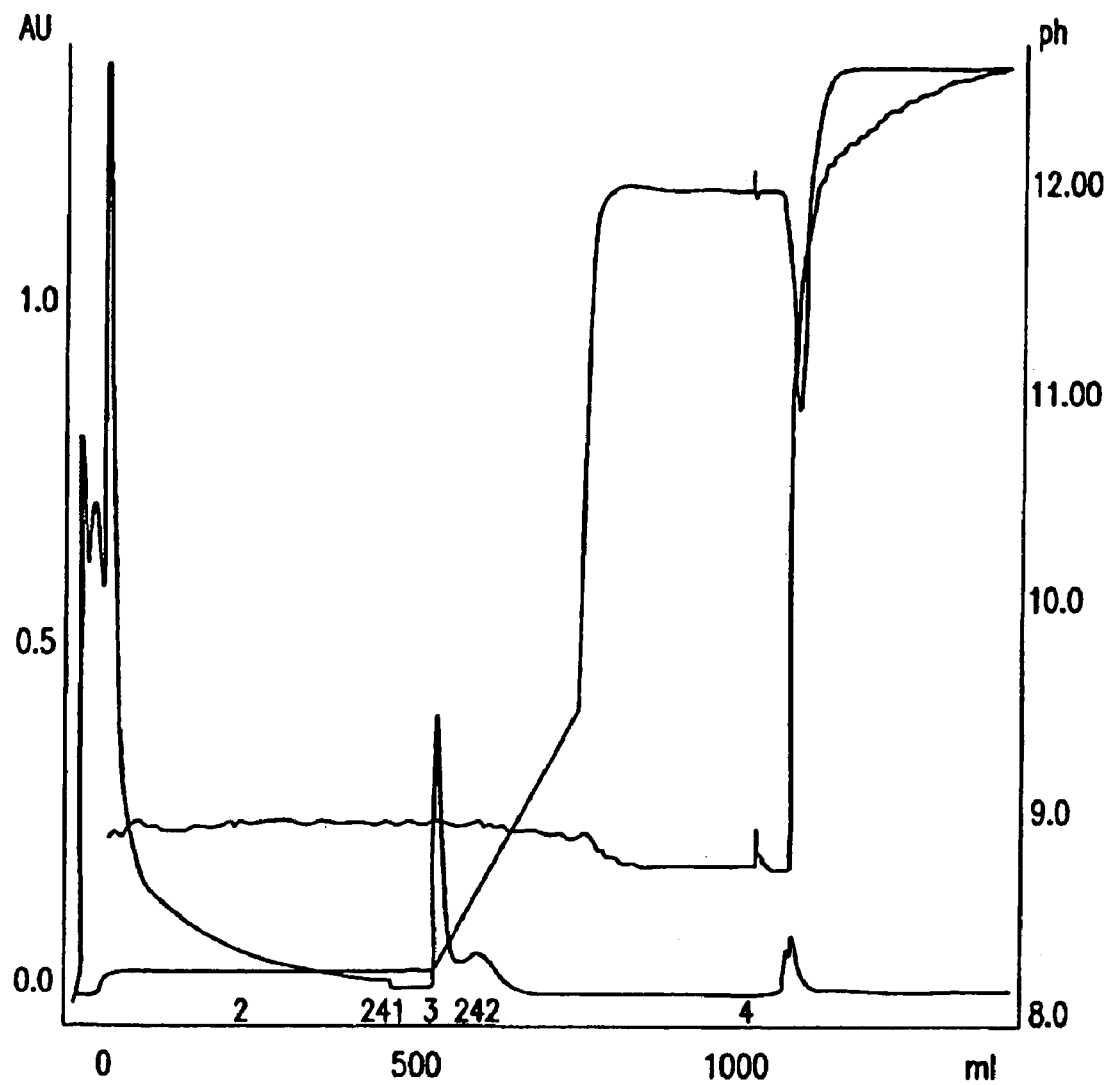
FIG. 15. The elution profile of treated virus solution purified using the method of the present invention using Toyopearl SuperQ resin.
Figure 16A:
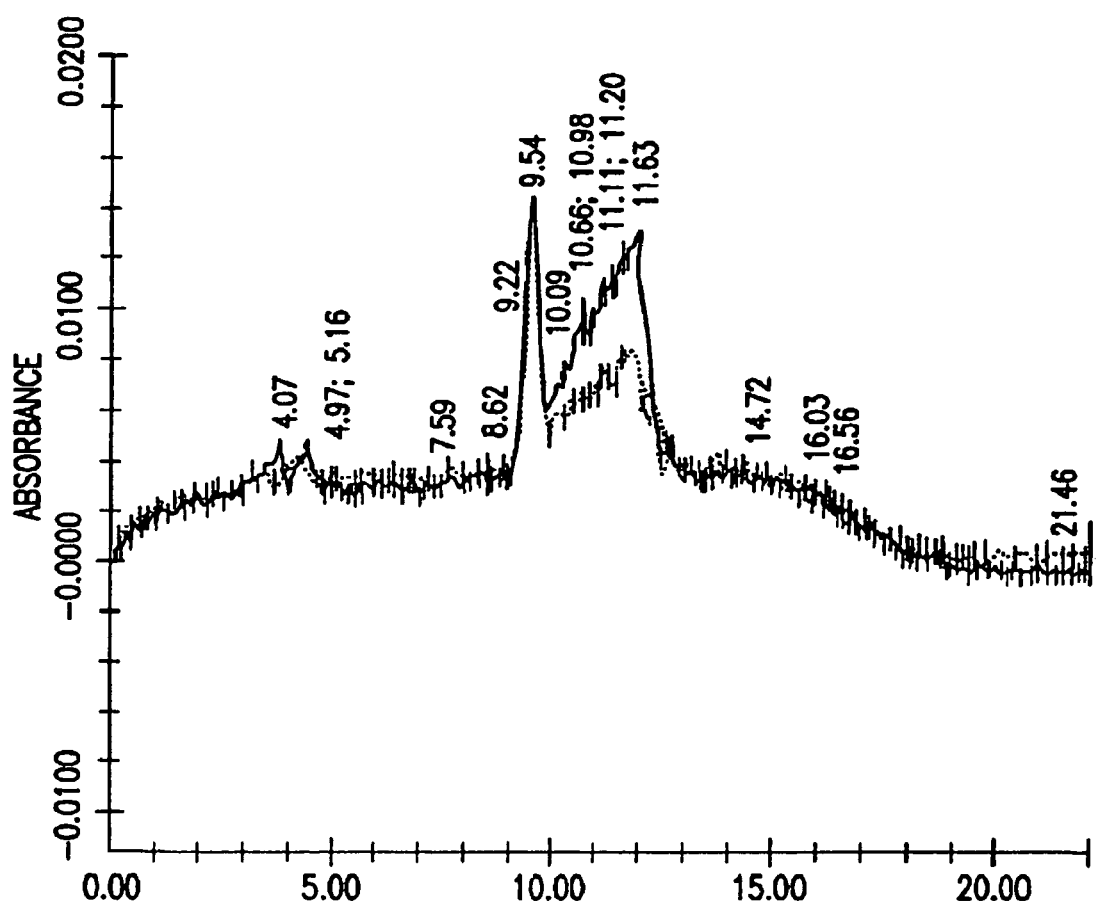
FIG. 16A and FIG. 16B. HPLC analysis of virus fraction from purification protocol.

After clarification and filtration, the virus solution was concentrated/diafiltrated and treated with Benzonase to reduce the contaminating nucleic acid concentration. The treated virus solution was purified by the method developed above using Toyopearl SuperQ resin. Satisfactory separation, similar to that obtained using virus supernatant from the bioreactor, was achieved during elution. FIG. 15 shows the elution profile. However, when the virus fraction was analyzed on HPLC, another peak in addition to the virus peak was detected. The result is shown in FIG. 16A.

Figure 16B:
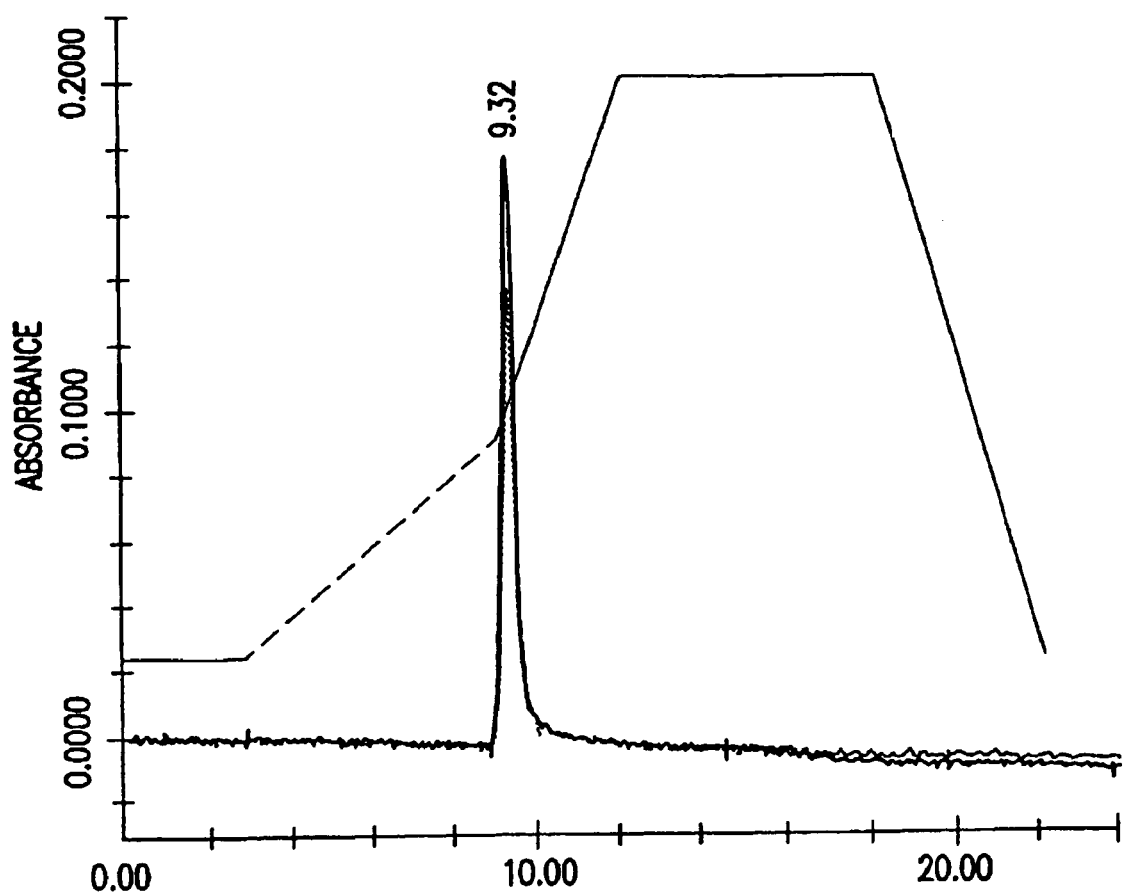

To further purify the virus, the collected virus fraction was re-purified using the same method. As shown in FIG. 16B, purity of the virus fraction improved considerably after the second purification. Metal chelate chromatography was also evaluated as a candidate for the second purification. Similar improvement in virus purity as seen with the second IEC was achieved. However, because of its simplicity, IEC is preferred as the method of choice for the second purification.

As described above in Example 2, medium perfusion rate employed during the cell growth and virus production phases has a considerable impact on the HPLC separation profile of the Tween-20 crude virus harvest. For crude virus solution produced under high medium perfusion rate, two ion exchange columns are required to achieve the required virus purity.

Figure 17:
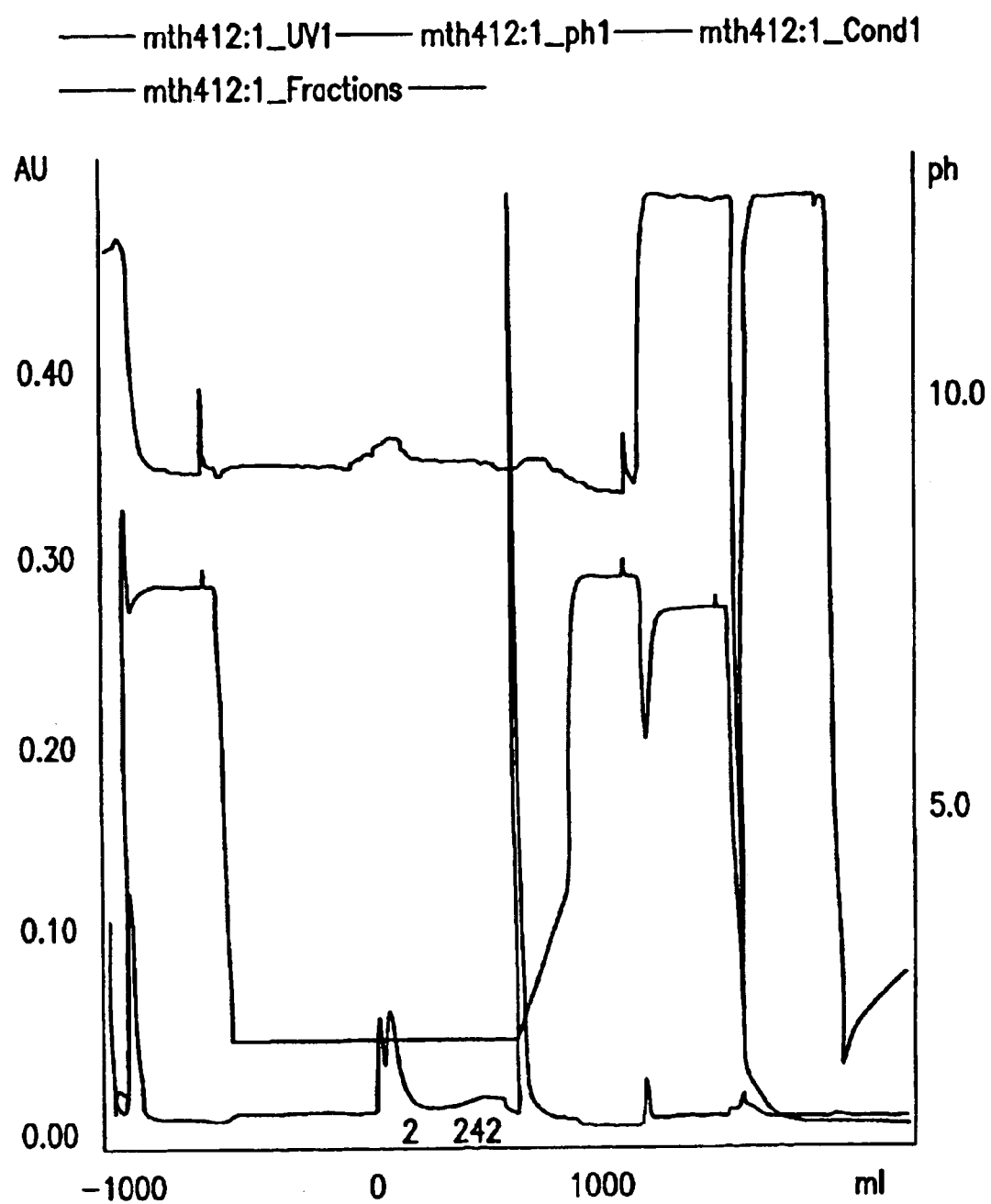
FIG. 17. Purification of 1% Tween® harvest virus solution under low medium perfusion rate.
Figure 18:
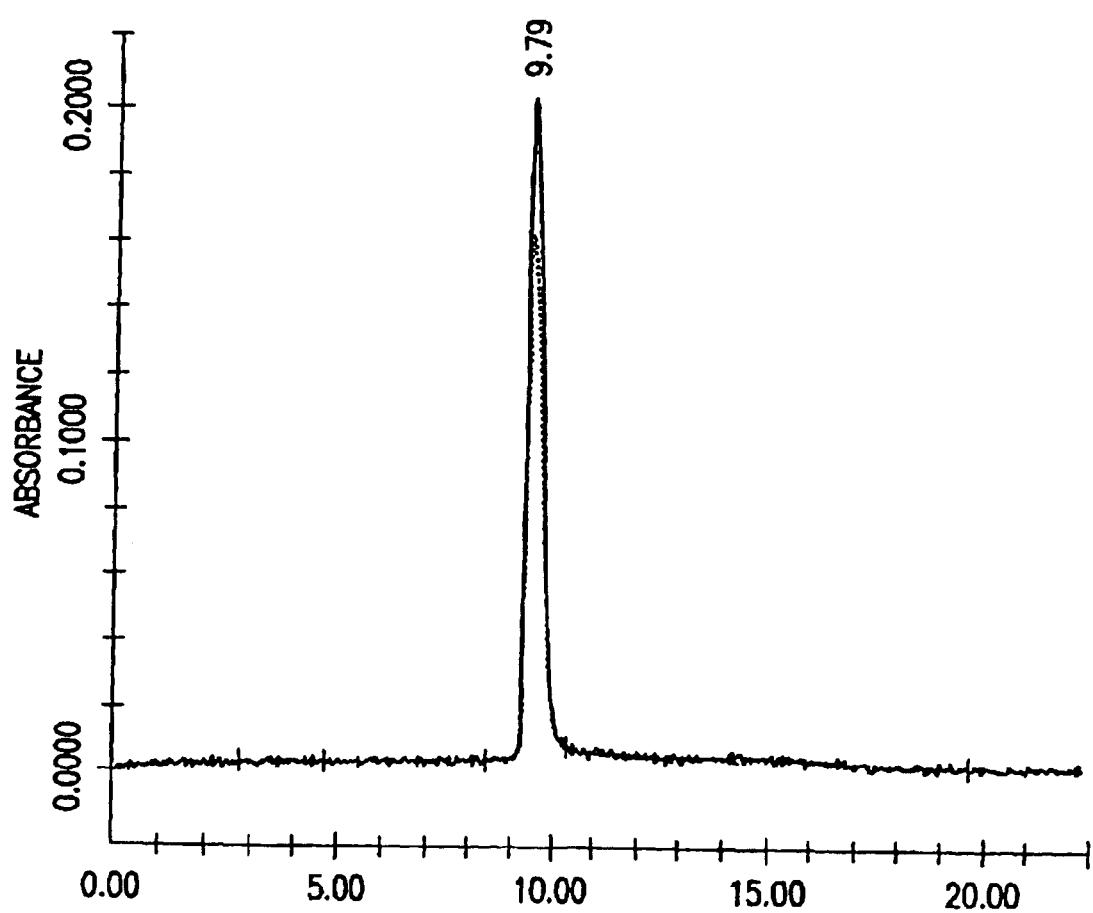
FIG. 18. HPLC analysis of the virus fraction produced under low medium perfusion rate.

Based on the much improved separation observed on HPLC for virus solution produced under low medium perfusion rate, it is likely that purification through one ion exchange column may achieve the required virus parity. FIG. 17 shows the elution profile using crude virus solution produced under low medium perfusion rate. A sharp virus peak was attained during elution. HPLC analysis of the virus faction indicates virus purity equivalent to that of CsCl gradient purified virus after one ion exchange chromatography step. FIG. 18 shows the HPLC analysis result.

Figure 19A:
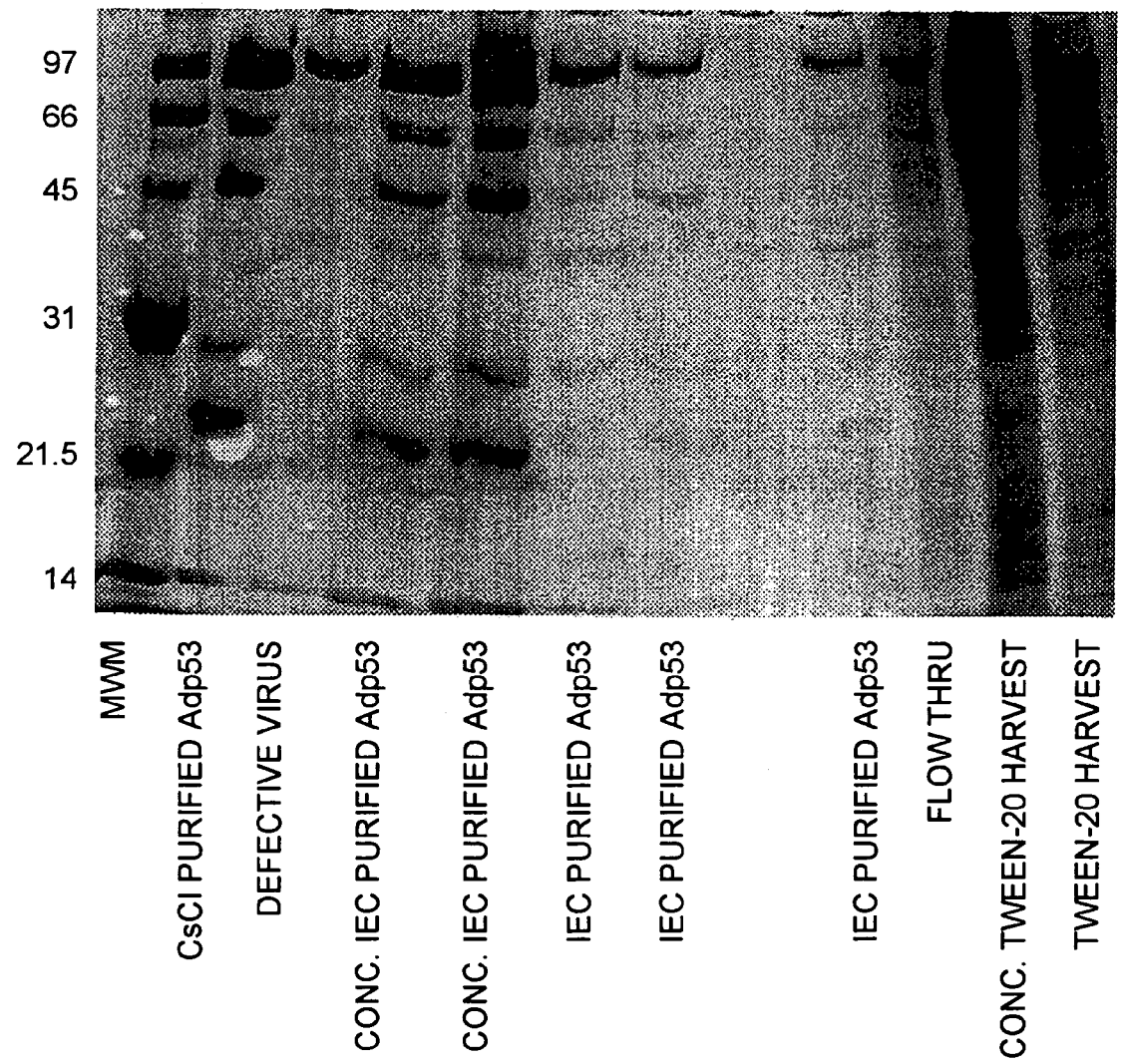
FIG. 19A, FIG. 19B and FIG. 19C. Analysis of column purified virus.
Figure 19B:
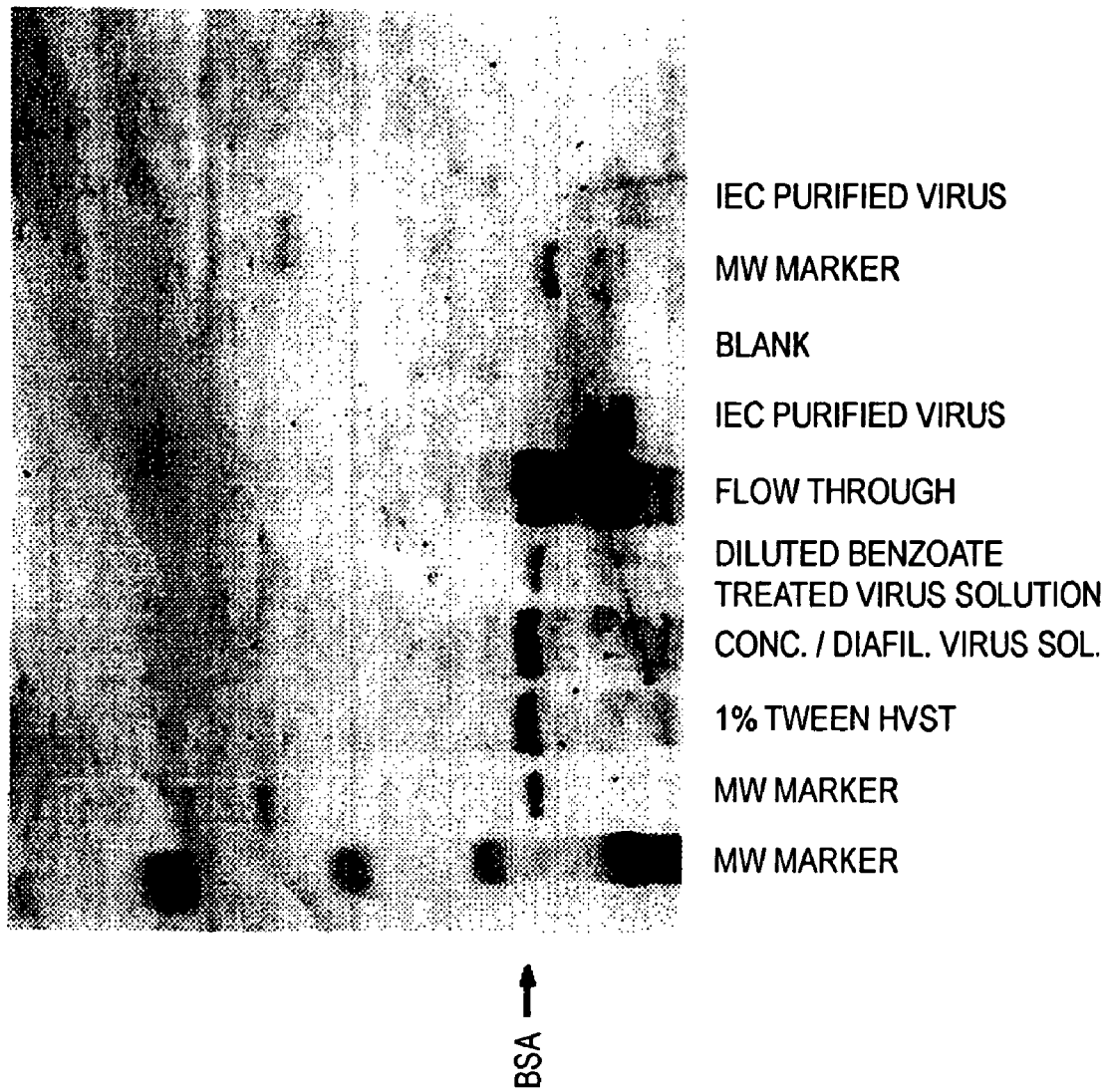
Figure 19C:
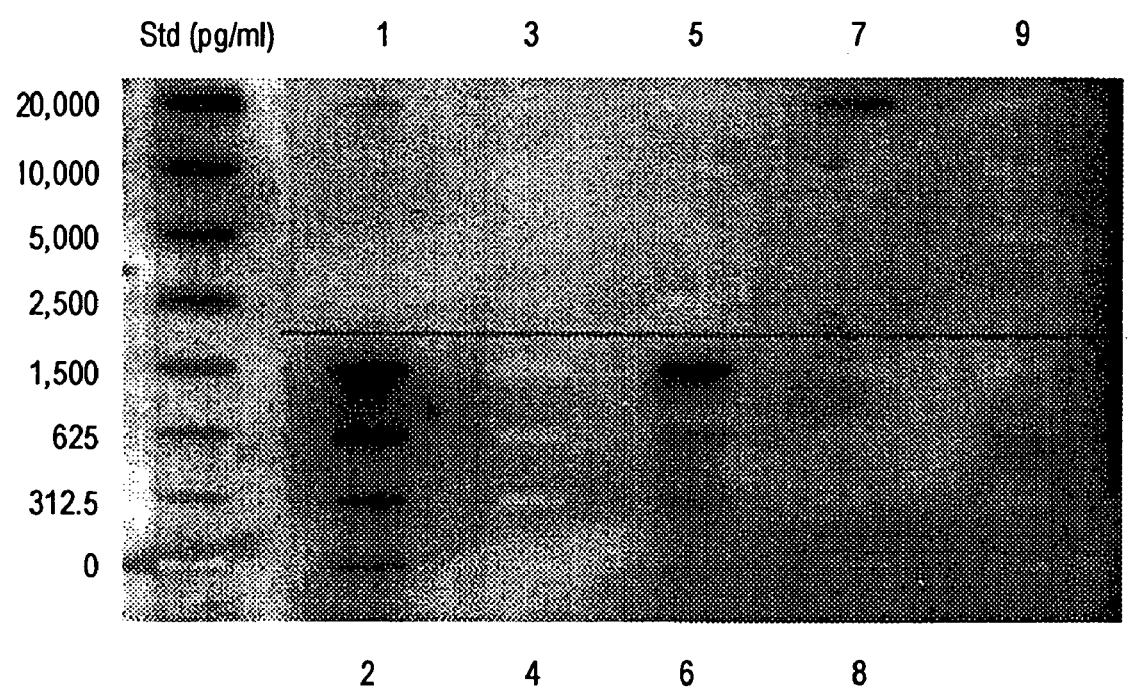
Figure 20A:
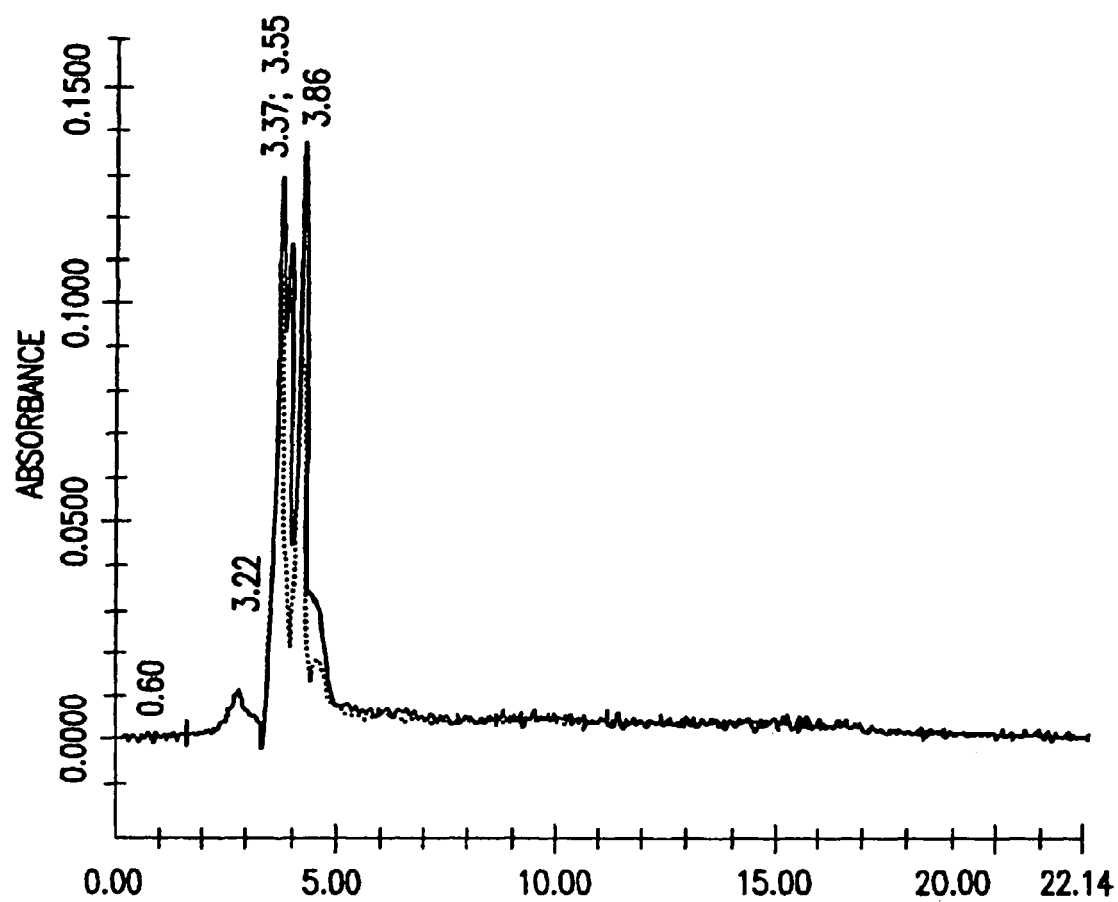
Figure 20B:
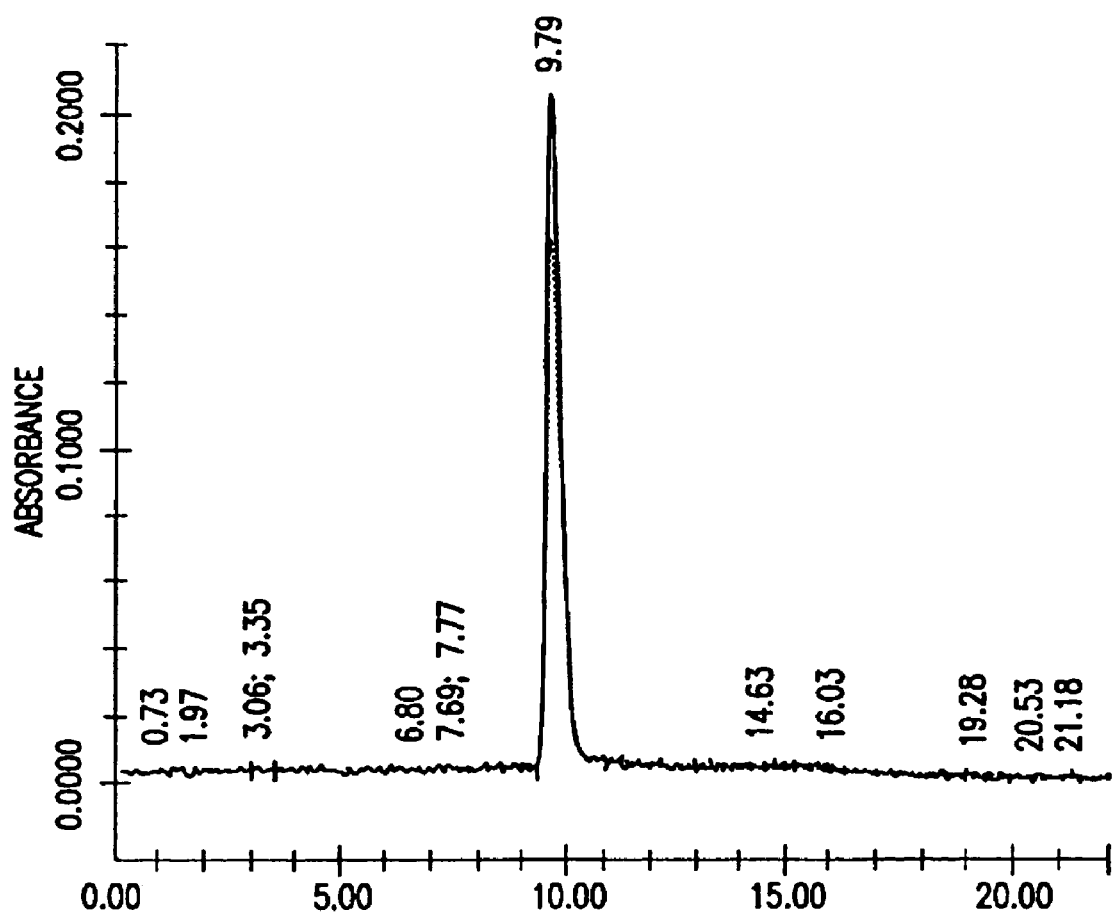
Figure 20C:
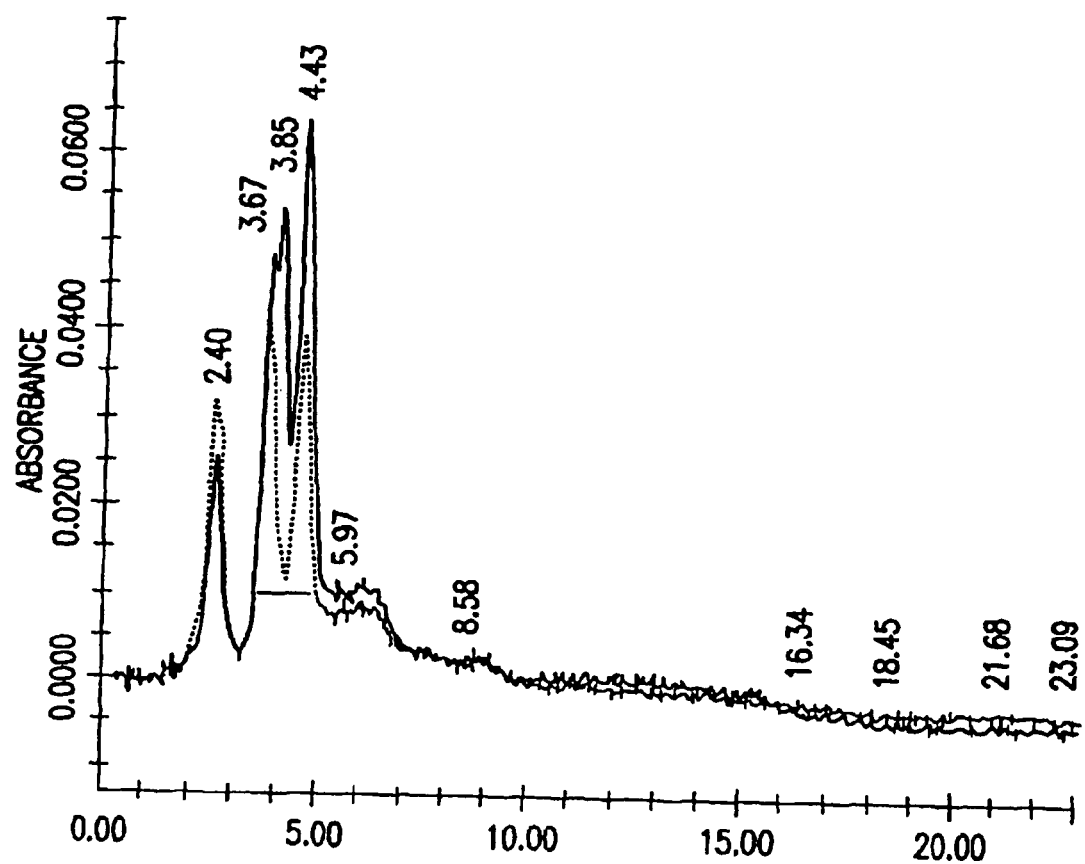
Figure 20D:
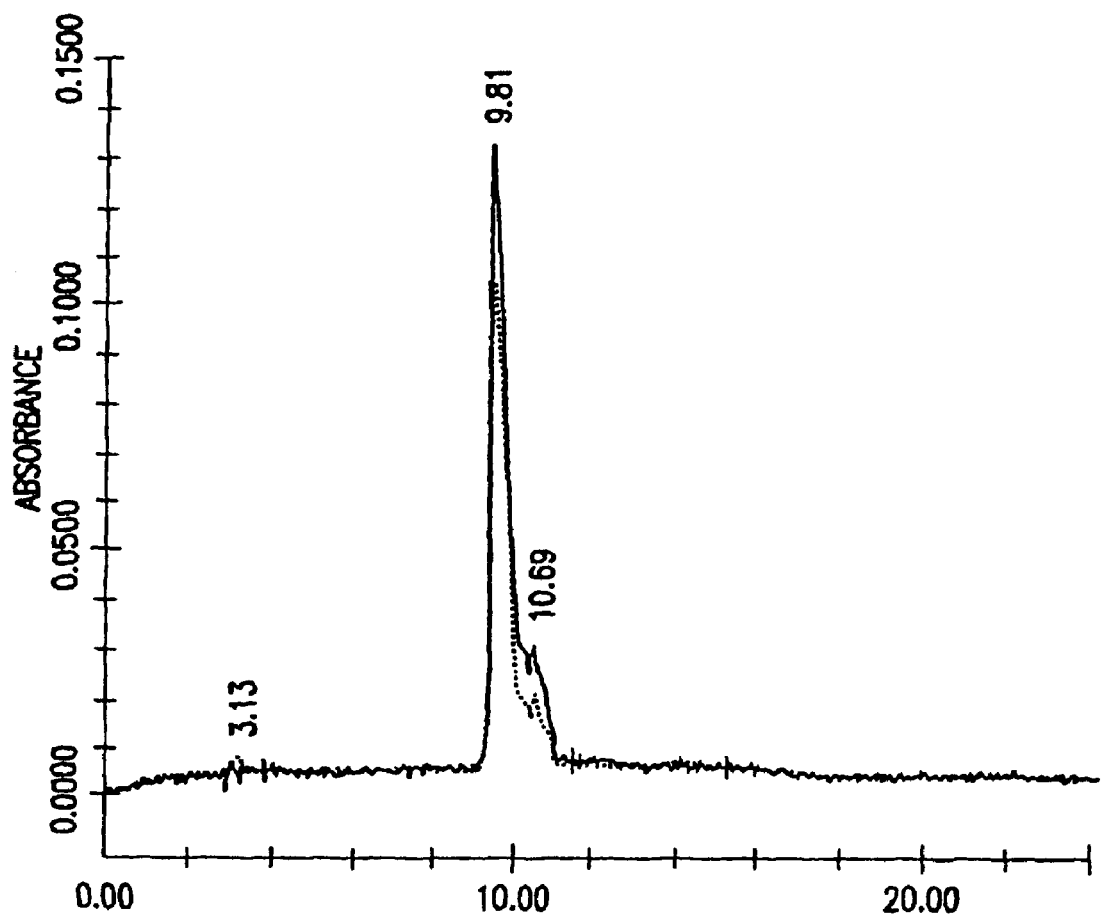
Figure 20E:
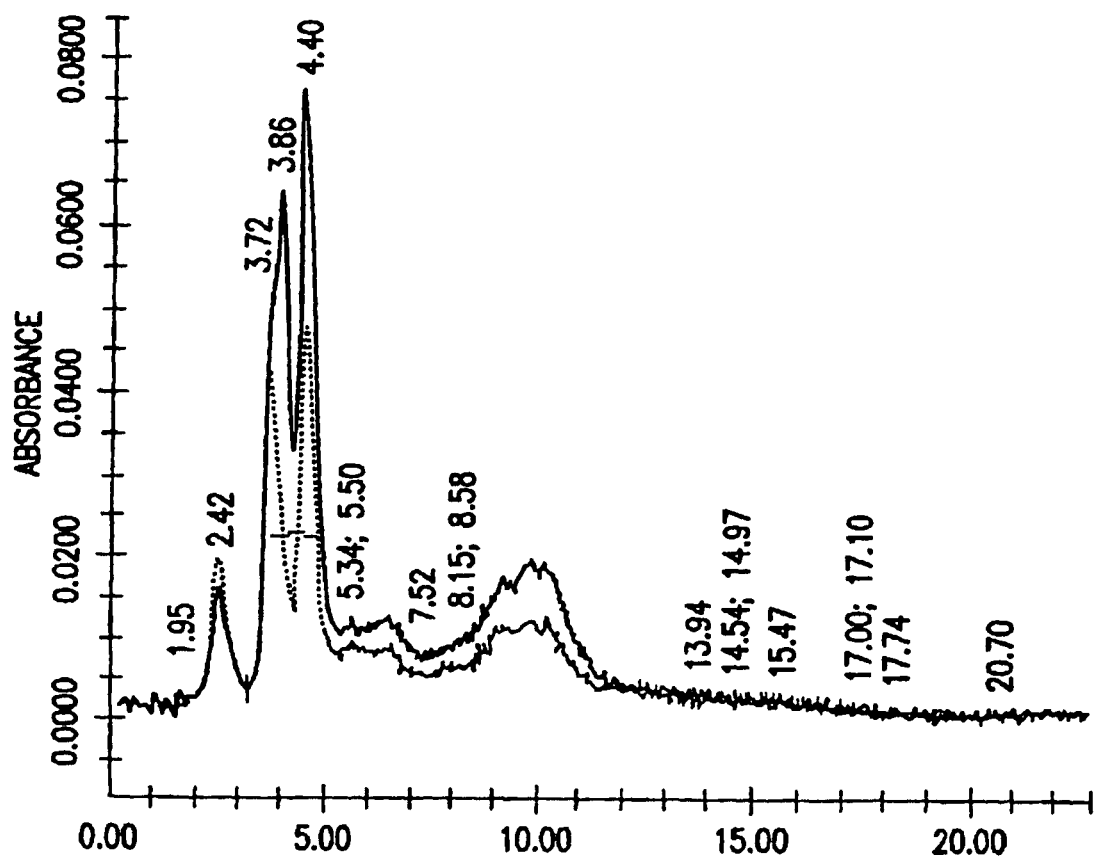
Figure 2O:
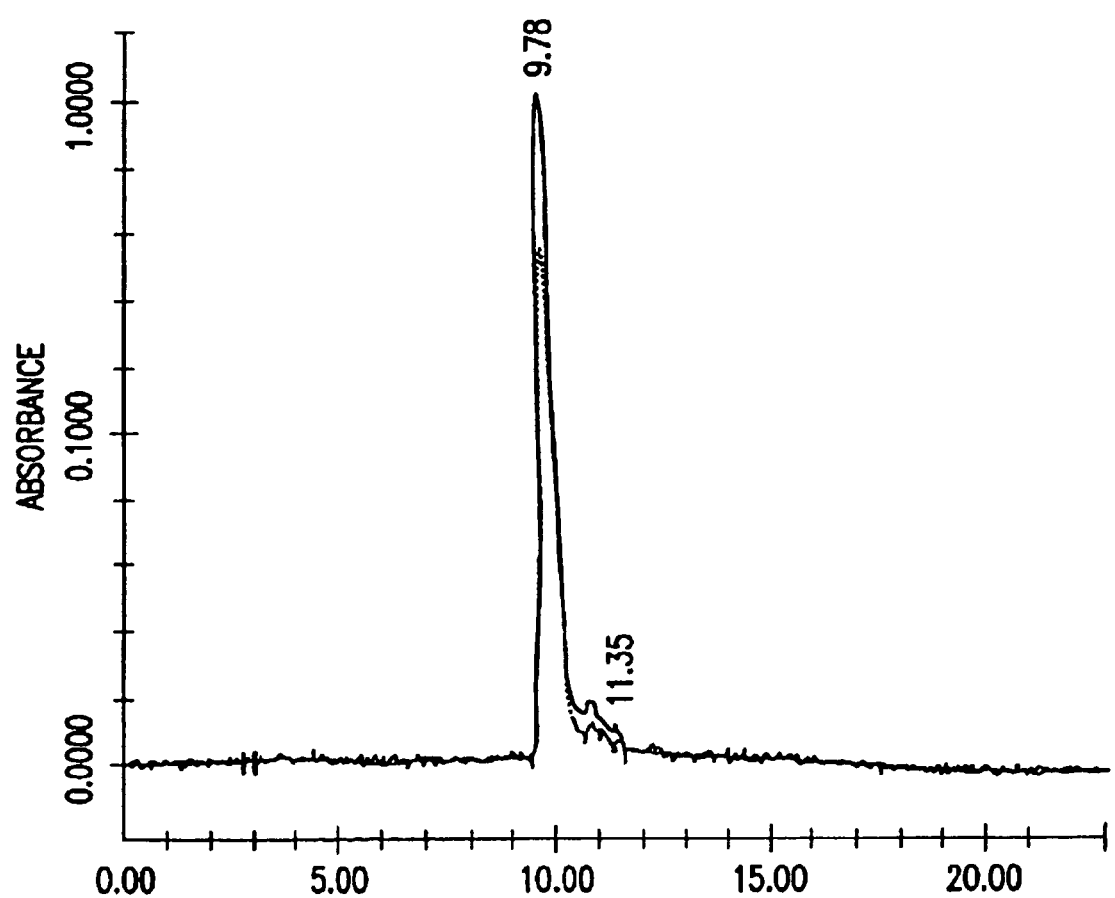

The purified virus was further-analyzed by SDS-PAGE, western blot for BSA, and nucleic acid slot blot to determine the contaminating nucleic acid concentration. The analysis results are given in FIG. 19A, FIG. 19B and FIG. 19C, respectively. All those analyses indicate that the column purified virus has equivalent purity compared to the double CsCl gradient purified virus. Table 11 shows the virus titer and recovery before and after the column purification. For comparison purposes, the typical virus recovery achieved by double CsCl gradient purification was also included. Similar virus recoveries were achieved by both methods.

TABLE 11

Comparison of IEC and double CsCl gradient ultracentrifugation purification of AdCMVp53 from Cellcube ™

|  | Titer (PFU/ml) | A260/ A280 | Particle/ PFU | Recovery |
|---|---|---|---|---|
| IEC | $1 \times 10^{10}$ | 1.27 | 36 | 63% |
| Ultracentrifugation | $2 \times 10^{10}$ | 1.26 | 38 | 60% |

A) Resin Capacity Study

The dynamic capacity of the Toyopearl Super Q resin was evaluated for the purification of the Tween-20 harvested virus solution produced under low medium perfusion rate. One hundred ml of resin was packed in a XK50 column. Different amount of crude virus solution was purified through the column using the methods described herein.

Virus breakthrough and purification efficiency were analyzed on HPLC. FIG. 20 shows the HPLC analysis results. At a column loading factor greater than sample/column volume ratio of 2:1, purity of the virus fraction was reduced. Contaminants co-eluted with the virus. At a loading factor of greater than 3:1, breakthrough of the virus into the flow through was observed. Therefore, it was proposed that the working loading capacity of the resin be in the range of sample/column volume ratio of 1:1.

B) Concentration/diafiltration Post Purification

A concentration/diafiltration step after column purification serves not only to increase the virus titer, if necessary, but also to exchange to the buffer system specified for the virus product. A 300K NMWC TFF membrane was employed for the concentration step. Because of the absence of proteinacious and nucleic acid contaminants in the purified virus, very high buffer flux was achieved without noticeable pressure drop across the membrane.

Approximately 100% virus recovery was achieved during this step by changing the buffer into 20 mM Tris+1 mM $MgCl_2$+0.15 M NaCl, pH=7.50. The purified virus was also successfully buffer exchanged into DPBS during the concentration/diafiltration step. The concentration factor can be determined by the virus titer that is desired in the final product and the titer of virus solution eluted from the column. This flexibility will help to maintain the consistency of the final purified virus product.

C) Evaluation of Defective Adenovirus in the IEC Purified AdCMVp53

Due to the less than 100% packaging efficiency of adenovirus in producer cells, some defective adenoviruses generally exist in crude virus solution. Defective viruses do not have DNA packaged inside the viral capsid and therefore can be separated from intact virus on CsCl gradient ultracentrifugation based the density difference. It is likely that it would be difficult to separate the defective from the intact viruses based on ion exchange chromatography assuming both viruses have similar surface chemistry. The presence of excessive amount of defective viruses will impact the quality of the purified product.

Figure 21:
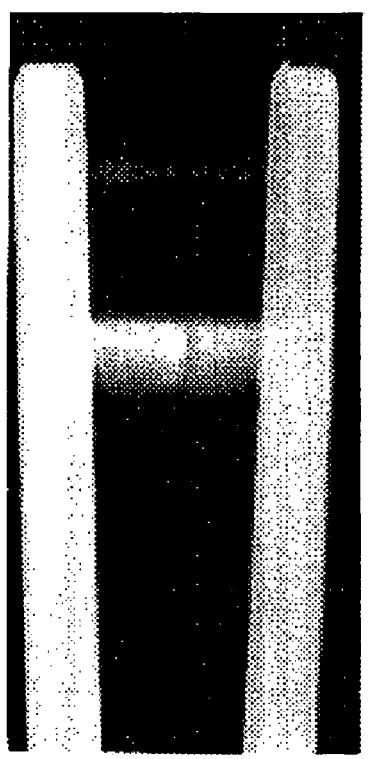
FIG. 21. Isopycnic CsCl ultracentrifugation column purified virus.
Figure 22A:
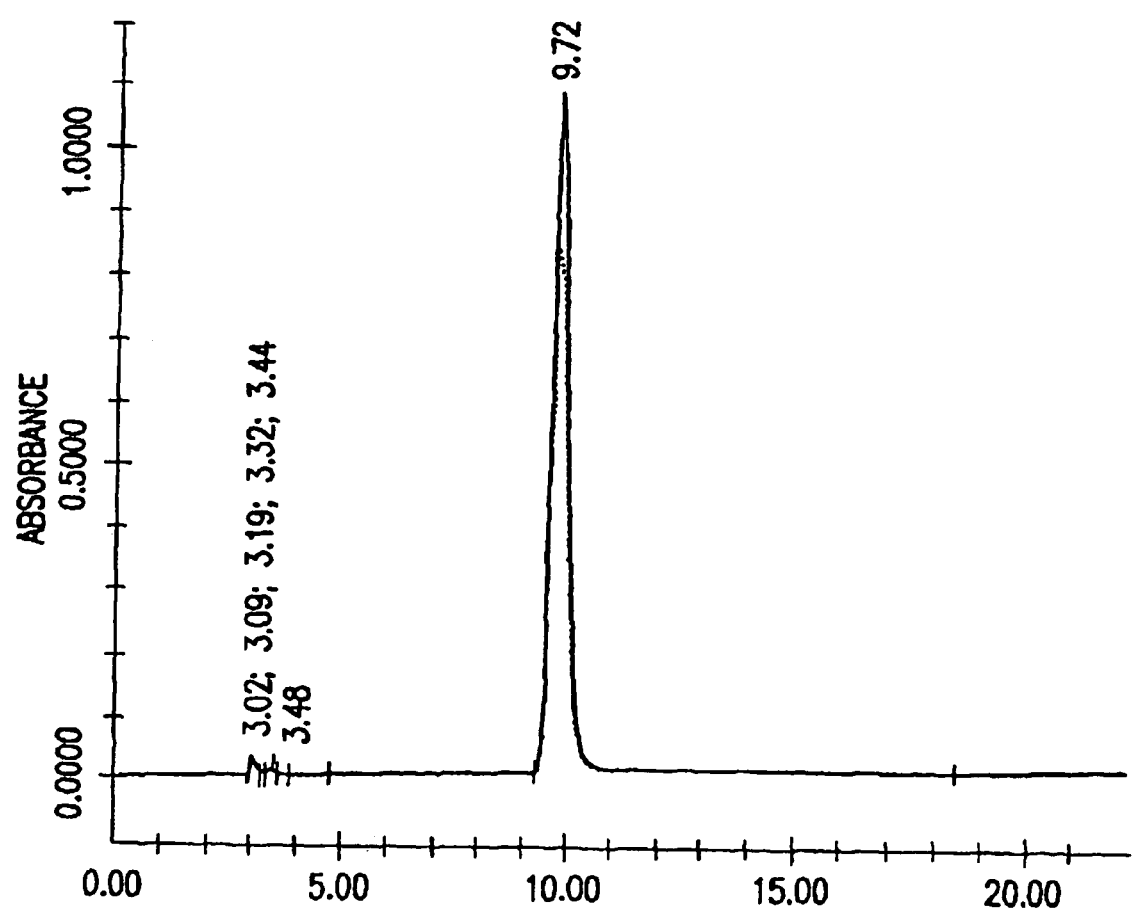
FIG. 22. The HPLC profiles of intact viruses present in the column purified virus. A. Intact virus B. Defective virus. (solid line $A_{260}$; dotted line $A_{280}$).
Figure 22B:
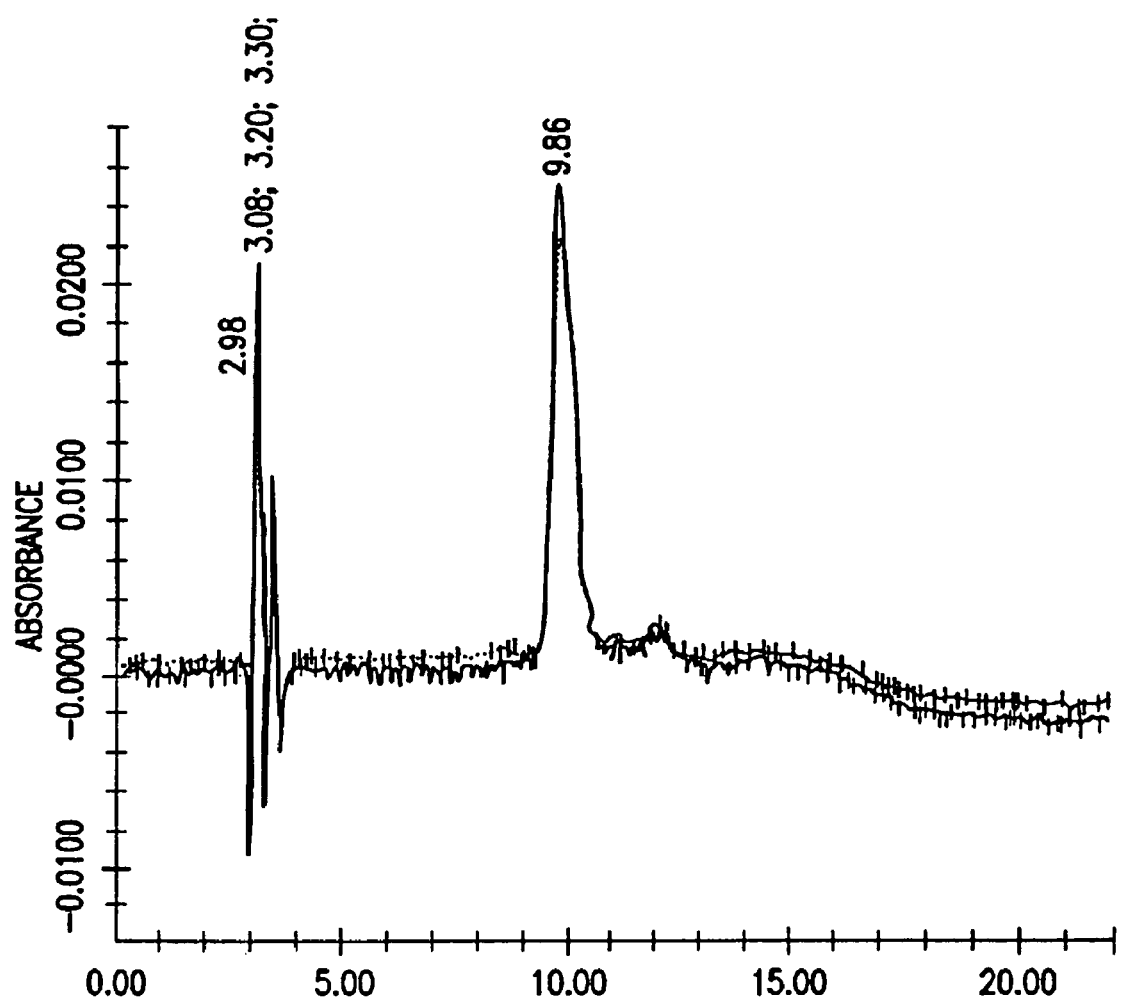

To evaluate the percentage of defective virus particles present, the purified and concentrated viruses were subjected to isopicnic CsCl ultracentrifugation. As shown in FIG. 21, a faint band on top of the intact virus band was observed after centrifugation. Both bands were recovered and dialyzed against 20 mM Tris+1 mM $MgCl_2$, pH=7.50 buffer to remove CsCl. The dialyzed viruses were analyzed on HPLC and the results are shown in FIG. 22. Both viruses show similar retention time. However, the defective virus has a smaller A260/

A280 ratio than that of the intact virus. This is indicative of less viral DNA in the defective virus.

The peaks seen at retention times: between 3.02 to 3.48 min arm produced by glycerol which is added to the viruses (10% v/v) before freezing at −70° C. The percentage of the defective virus was less than 1% of the total virus. This low percentage of defective virus is unlikely to impact the total particle to infectious virus (PFU) ratio in the purified virus product. Both viruses were analyzed by SDS-PAGE (shown in FIG. 19A). Compared to the intact viruses, defective viruses lack the DNA associated core proteins banded at 24 and 48.5 KD. This result is in agreement with the absence of DNA in defective virus.

D) Process Overview of the Production and Purification of AdCMVp53 Virus

Based on the above process development results, the inventors propose a production and purification flow chart for AdCMVp53 as shown in FIG. 23. The step and accumulative virus recovery is included with the corresponding virus yield based on a 1 mer Cellcube™. The final virus recovery is about 70±10%. This is about 3-fold higher than the virus recovery reported by Huyghe et al. (1996) using a DEAE ion exchanger and a metal chelate chromatographic purification procedure for the purification of p53 protein encoding adenovirus. Approximately $3 \times 10^{12}$ PFU of final purified virus product was produced from a 1 mer Cellcube™. This represents a similar final product yield compared to the current production method using double CsCl gradient ultracentrifugation for purification.

E) Scale-up

Successful scale-up studies are have been performed with the 4 mer Cellcube™ system, and are currently underway to evaluate virus production in the 16 mer Cellcube™ system. The crude virus solution produced will be filtered, concentrated and diafiltrated using a bigger Pellicon cassette. The quality and recovery of the virus will be determined. After Benzonase treatment, the crude virus solution will be purified using a 20 cm and a 30 cm BioProcess column for the 4 mer and 16 mer, respectively.

Example 9

Improved Ad-p53 Production in Serum-free Suspension Culture

Adaptation of 293 Cells 293 cells were adapted to a commercially available IS293 serum-free media (Irvine Scientific; Santa Ana, Calif.) by sequentially lowering down the FBS concentration in T-flasks. The frozen cells in one vial of PDWB were thawed and placed in 10% FBS DMEM media in T-75 flask and the cells were adapted to serum-free IS 293 media in T-flasks by lowering down the FBS concentration in the media sequentially. After 6 passages in T-75 flasks the FBS % was estimated to be about 0.019%. The cells were subcultured two more times in the T flasks before they were transferred to spinner flasks.

Serum-free Adapted 293 Cells in T Flasks were Adapted to Suspension Culture

The above serum-free adapted cells in T-flasks were transferred to a serum-free 250 mL spinner suspension culture (100 mL working volume) for the suspension culture. The initial cell density was 1.18E+5 vc/mL. During the cell culture the viability decreased and the big clumps of cells were observed. After 2 more passages in T-flasks the adaptation to suspension culture was tried again. In a second attempt the media was supplemented with heparin, at a concentration of 100 mg/L, to prevent aggregation of cells and the initial cell density was increased to 5.22E+5 vc/mL. During the cell culture there was some increase of cell density and cell viability was maintained. Afterwards the cells were subcultured in the spinner flasks for 7 more passages and during the passages the doubling time of the cells-was progressively reduced and at the end of seven passages it was about 1.3 day which is comparable to 1.2 day of the cells in 10% FBS media in the attached cell culture. In the serum-free IS 293 media supplemented with heparin almost all the cells existed as individual cells not forming aggregates of cells in the suspension culture (Table 12).

TABLE 12

Serum-Free Suspension Culture: Adaptation to Suspension

| Passage No. | Flask No. | Average Doubling Time (days) |
|---|---|---|
| 11 | | Viability decreased |
| 13 | | 3.4 |
| 14 | | 3.2 |
| 15 | 1 | Viability decreased |
| heparin added | 2 | 4.7 |
| | 3 | 5.0 |
| | 4 | 3.1 |
| 16 | 1 | 5.5 |
| | 2 | 4.8 |
| | 3 | 4.3 |
| | 4 | 4.3 |
| 17 | 1 | 2.9 |
| | 2 | 3.5 |
| | 3 | 2.4 |
| | 4 | 1.7 |
| 18 | 1 | 3.5 |
| | 2 | 13.1 |
| | 3 | 6.1 |
| | 4 | 3.8 |
| 19 | 1 | 2.5 |
| | 2 | 2.6 |
| | 3 | 2.3 |
| | 4 | 2.5 |
| 20 | 1 | 1.3 (97% viability) |
| | 2 | 1.5 (99% viability) |
| | 3 | 1.8 (92% viability) |
| | 4 | 1.3 (96% viability) |

Viral Production and Growth of Cells in Serum-free Suspension Culture in Spinner Flask To test the production of Ad5-CMVp53 vectors in the serum-free suspension culture the above cells adapted to the serum-free suspension culture were grown in 100 mL serum-free IS293 media supplemented with 0.1% Pluronic F-68 and Heparin (100 mg/L) in 250 mL spinner flasks the cells were infected at 5 MOI when the cells reached 1.36E+06 viable cells/mL on day 3. The supernatant was analyzed everyday for HPLC viral particles/mL after the infection. No viruses were detected other than day 3 sample. On day 3 it was 2.2E+09 vps/mL. The pfu/mL on day 6 was 2.6+/−0.6E+07 pfu/mL. The per cell pfu production was estimated to be 19 which is approximately 46 times below the attached culture in the serum-supplemented media. As a control the growth of cells was checked in the absence of an infection.

TABLE 13

Serum-Free Suspension Culture: Viral Production and Cell Growth

|  | Control w/o viral infection | Viral infection w/o media exchange | Viral infection w/media exchange |
|---|---|---|---|
| Initial Density (vc/mL) | $2.1 \times 10^5$ | $2.1 \times 10^5$ | $2.1 \times 10^5$ |
| Cell Density at infection (vc/mL) | $9.1 \times 10^5$ | $1.4 \times 10^6$ | $1.5 \times 10^6$ |
| Volumetric viral production (pfu/mL) 6 days P.I. | NA | $2.6 \times 10^7$ | $2.8 \times 10^8$ |
| Volumetric viral production (HPLC vps/mL) 6 days P.I. | NA | NA | $1.3 \times 10^{10}$ |
| Per cell viral production (HPLC vps/cell) | NA | NA | $1.3 \times 10^4$ |

Preparation of Serum-free Suspension Adapted 293 Cell Banks

As described above, after it was demonstrated the cells produce the Ad-p53 vectors, the cells were propagated in the serum-free IS293 media with 0.1% F-68 and 100 mg/L heparin in the spinner flasks to make serum-free suspension adapted cell banks which contain 1.0E+07 viable cells/mL/vial. To collect the cells they were centrifuged down when they were at mid-log phase growth and the viability was over 90% and resuspended in the serum-free, supplemented IS293 media and centrifuged down again to wash out the cells. Then the cells were resuspended again in the cryopreservation media which is cold IS293 with 0.1% F-68, 100 mg/L heparin, 10% DMSO and 0.1% methylcellulose resulting in 1E+07 viable cells/mL. The cell suspension was transferred to sterile cryopreservation vials and they were sealed and frozen in cryocontainer at −70 C. overnight. The vials were transferred to liquid nitrogen storage. The mycoplasma test was negative.

To revive the frozen cells one vial was thawed into the 50 mL serum-free IS293 media with 0.1% F-68 and 100 mg/L heparin in a T-150. Since then the cultures were subcultured three times in 250 mL spinner flasks. In the other study one vial was thawed into 100 mL serum-free, supplemented IS293 media in a 250 mL spinner flask. Since then these were subcultured in serum-free spinner flasks 2 times. In both of the studies the cells grew very well.

Media Replacement and Viral Production in Serum-free Suspension Culture in Spinner Flask In the previous serum-free viral production in the suspension culture in the spinner flask the per cell viral production was too low for the serum-free suspension production to be practical. It was supposed that this might be due to the depletion of nutrients and/or the production of inhibitory byproducts. To replace the spent media with fresh serum-free, supplemented IS293 media the cells were centrifuged down on day 3 and resuspended in a fresh serum-free IS-293 medium supplemented with F-68 and heparin (100 mg/L) and the resulting cell density was 1.20E+06 vc/mL and the cells were infected with Ad5-CMVp53 vectors at 5 MOI. The extracellular HPLC vps/mL was 7.7E+09 vps/mL on day 3, 1.18E+10 vps/mL on day 4, 1.2E+10 vps/mL on day 5 and 1.3E+10 vps/mL on day 6 and the pfu/mL on day 6 was 2.75+/−0.86E+08 tvps/mL. The ratio of HPLC viral particles to pfus was about 47. Also the cells have been centrifuged down and lysed with the same type of the detergent lysis buffer as used in the harvest of CellCube. The cellular HPLC vps/mL was 1.6E+10 vps/mL on day 2, 6.8E+09 vps/mL on day 3, 2.2E+09 vps/mL on day 4, 2.24E+09 vps/mL on day 5 and 2.24E+09 vps/mL on day 6.

The replacement of the spent media with a fresh serum-free, supplemented IS 293 media resulted in the significant increase in the production of Ad-p53 vectors. The media replacement increased the production of extracellular HPLC viral particles 3.6 times higher above the previous level on day 3 and the production of extracellular pfu titer ten times higher above the previous level on day 6. Per cell production of Ad-p53 vectors was estimated to be approximately 1.33E+04 HPLC vps.

The intracellular HPLC viral particles peaked on day 2 following the infection and then the particle numbers decreased. In return the extracellular viral particles increased progressively to the day 6 of harvest. Almost all the Ad-p53 vectors were produced for the 2 days following the infection and intracellularly localized and then the viruses were released outside of the cells. Almost half of the viruses were released outside of the cells into the supernatant between day 2 and day 3 following the infection and the rate of release decreased as time goes on.

All the cells infected with Ad-p53 vectors lost their viability at the end of 6 days after the infection while the cells in the absence of infection was 97% viable. In the presence of infection the pH of the spent media without the media exchange and with the media exchange was 6.04 and 5.97, respectively, while the one in the absence of the infection was 7.00 (Table 12).

Viral Production and Cell Culture in Stirred Bioreactor with Media Replacement and Gas Overlay To increase the production of Ad-p53 vectors, a 5 L CelliGen bioreactor was used to provide a more controlled environment. In the 5 L CelliGen bioreactor the pH and the dissolved oxygen as well as the temperature was controlled. Oxygen and carbon dioxide gas was connected to the solenoid valve for oxygen supply and the pH adjustment, respectively. For a better mixing while generating low shear environment a marine-blade impeller was implemented. Air was supplied all the time during the operation to keep a positive pressure inside the bioreactor.

To inoculate the bioreactor a vial of cells was thawed into 100 mL serum-free media in a 250 mL spinner flask and the cells were expanded in 250 or 500 mL spinner flasks. 800 mL cell inoculum, grown in 500 mL flasks, was mixed with 2700 mL fresh media in a 10 L carboy and transferred to the CelliGen bioreactor by gas pressure. The initial working volume of the CelliGen bioreactor was about 3.5 L culture. The agitation speed of the marine-blade impeller was set at 80 rpm, the temperature at 37° C., pH at 7.1 at the beginning and 7.0 after the infection and the DO at 40% all the time during the run.

The initial cell density was 4.3E+5 vc/mL (97% viability) and 4 days later when the cell density reached to 2.7E+6 vc/mL (93% viability) the cells were centrifuged down and the cells were resuspended in a fresh media and transferred to the CelliGen bioreactor. After the media exchange the cell density was 2.1E+6 vc/mL and the cells were infected at MOI of 10. Since then the DO dropped to below 40%. To keep the DO above 40%, about 500 mL of culture was withdrawn from the CelliGen bioreactor to lower down the oxygen demand by the cell culture and the upper marine-blade was positioned close to the interface between the gas and the liquid phase to improve the oxygen transfer by increasing the surface renewal. Since then the DO could be maintained above 40% until the end of the run.

For pH control, $CO_2$ gas was used to acidify the cell culture and 1 N $NaHCO_3$ solution to make the cell culture alkaline. The pH control was initially set at 7.10. The initial pH of the cell culture was about pH 7.41. Approximately 280 mL 1N $NaHCO_3$ solution was consumed until the pH of cell culture stabilized around pH 7.1. After the viral infection of the cell culture, the pH control was lowered down to pH 7.0 and the $CO_2$ gas supply line was closed off to reduce the consumption of $NaHCO_3$ solution. The consumption of too much $NaHCO_3$ solution for pH adjustment would increase the cell culture volume undesirably. Since then 70 mL 1N $NaHCO_3$ solution was consumed and the pH was in the range between 7.0 and 7.1 most of the time during the run. The temperature was controlled between 35° C. and 37° C.

After the infection the viability of the cells decreased steadily until day 6 of harvest after the infection. On the harvest day none of the cells was viable. The volumetric viral production of the CelliGen bioreactor was 5.1E+10 HPLC vps/mL compared to the 1.3E+10 vps/mL in the spinner flask. The controlled environment in the CelliGen bioreactor increased the production of Ad-p53 vectors 4fold compared to the spinner flasks with media replacement. This is both, due to the increase of the cell density at the time of infection from 1.2E+6 to 2.1 E+6 vc/mL and the increase of per cell viral production from 1.3E+4 to 2.5E+4 vps/mL. The 2.5E+4 vps/mL is comparable to the 3.5E+4 vps/cell in the serum-supplemented, attached cell culture.

Viral Production and Cell Culture in Stirred and Sparged Bioreactor

In the first study the cells were successfully grown in an stirred bioreactor for viral production, and the oxygen and $CO_2$ were supplied by gas overlay in the headspace of a bioreactor. However, this method will limit the scale-up of the cell culture system because of its inefficient gas transfer. Therefore in the second study, to test the feasibility of the scale up of the serum-free suspension culture and investigate the growth of cells and Ad-p53 production in a sparged bioreactor, pure oxygen and $CO_2$ gases were supplied by bubbling through the serum-free IS293 media supplemented with F-68 (0.1%) and heparin (100 mg/L).

Pure oxygen was bubbled through the liquid media to supply the dissolved oxygen to the cells and the supply of pure oxygen was controlled by a solenoid valve to keep the dissolved oxygen above 40%. For efficient oxygen supply while minimizing the damage to the cells a stainless steel sintered air diffuser, with a nominal pore size of which is approximately 0.22 micrometer, was used for the pure oxygen delivery. The $CO_2$ gas was also supplied to the liquid media by bubbling from the same diffuser and tube as the pure oxygen to maintain the pH around 7.0. For pH control $Na_2CO_3$ solution (106 g/L) was also hooked up to the bioreactor. Air was supplied to the head space of the bioreactor to keep a positive pressure inside the bioreactor. Other bioreactor configuration was the same as the first study.

Inoculum cells were developed from a frozen vial. One vial of frozen cells (10E+7 vc) was thawed into 50 mL media in a T-150 flask and subcultured 3 times in 200 mL media in 500 mL spinner flasks. 400 mL of inoculum cells grown in 2 of 500 mL spinner flasks were mixed with IS293 media with F-68 and heparin in a 10 L carboy to make 3.5 L cell suspension and it was transferred to the 5 L CelliGen bioreactor.

The initial cell density in the bioreactor was 3.0E+4 vc/mL. The initial cell density is lower than the first study. In the first study four of 500 mL spinner flasks were used as the inoculum. Even with the lower initial cell density the cells were grown up to 1.8E+6 vc/mL on day 7 in the sparged environment and the viability was 98%. During the 7 days' growth, glucose concentration decreased from 5.4 g/L to 3.0 g/L and lactate increased from 0.3 g/L to 1.8 g/L.

On day 7, when the cell density reached 1.8E+6 vc/mL, the cells in the bioreactor were centrifuged down and resuspended in 3.5 L fresh serum-free IS293 media with F-68 and heparin in a 10 L carboy. The 293 cells were infected with 1.25E+11 pfu Ad-p53 and transferred to the CelliGen bioreactor. In the bioreactor, cell viability was 100% but the cell density was only 7.2E+5 vc/mL. There was a loss of cells during the media exchange operation. The viral titer in the media was measured as 2.5E+10 HPLC vps/mL on day 2, 2.0E+10 on day 3, 2.8E+10 on day 4, 3.5E+10 on day 5 and 3.9E+10 HPLC vps/mL on day 6 of harvest. The first CelliGen bioreactor study with gas overlay produced 5.1E+10 HPLC vps/mL. The lower virus concentration in the second run was likely due, to the lower cell density at the time of infection. Compared to the 7.2E+5 vc/mL in the second run, 2.1E+6 vc/mL was used in the first run. Actually the per cell production of Ad-p53 in the second sparged CelliGen bioreactor is estimated to be 5.4E+4 vps/cell which is the highest per cell production ever achieved so far. The per cell production in the first serum-free CelliGen bioreactor without sparging and the serum-supplemented T-flask was 2.5E+4 vps/cell and 3.5E+4 vps/cell, respectively.

After the viral infection, the viability of the cells decreased from 100% to 13% on day 6 of harvest. During those 6 days after the infection the glucose concentration decreased from 5.0 g/L to 2.1 g/L and the lactate increased from 0.3 g/L to 2.9 g/L. During the entire period of operation about 20 mL of $Na_2CO_3$ (106 g/L) solution was consumed.

The experimental result shows that it is technically and economically feasible to produce Ad-p53 in the sparged and stirred bioreactor. Scale-up and large-scale unit operation of sparged and stirred bioreactor are well established.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aboud et al., *Arch Virol.*, 71:185-195, 1982.
Arap et al, *Cancer Res.*, 55:1351-1354, 1995.
Bahnemann et al., *Abs. Pap. ACS*, 180:5. 1980.
Baichwal and Sugden, In: Kucherlapati R, ed. Gene transfer. New York: Plenum Press, pp. 117-148, 1986.

Benvenisty and Neshif, *Proc. Nat. Acad. Sci. USA*, 83:9551-9555, 1986.
Berg et al., *BioTechniques*, 14(6):972-978, 1993.
Bett, A. J., *Proc Natl Acad Sci USA*, 91 (19):8802-8806,1994.
Bussemakers et al., *Cancer Res.*, 52:2916-2922, 1992.
Caldas et al., *Nat. Genet.*, 8:27-32, 1994.
Casey et al, *Oncogene*, 6:1791-1797, 1991.
Chen and Okayama, *Mol. Cell Biol.*, 7:2745-2752, 1987.
Cheng et al., *Cancer Res.*, 54:5547-5551, 1994.
Cheung et al., *Biochem. J.*, 295:427-435, 1993c.
Cheung et al., *J. Biol. Chem.*, 268:24303-24310, 1993a
Cheung et al., *J. Biol. Chem.*, 268:6139-6146, 1993b.
Coffin, In: Fields B N, Knipe D M, ed. Virology. New York: Raven Press, pp. 1437-1500, 1990.
Coupar et al. *Gene*, 68:1-10, 1988.
Crooks et al, *J. Chrom.*, 502: 59-68, 1990.
Dubensky et al., *Proc. Nat, Acad. Sci. USA*, 0.81:7529-7533, 1984.
Edelman and Crossin,*Annu. Rev. Biochem*, 60:155-190, 1991
Edelman, *Annu. Rev. Biochem*, 54:135-169, 1985.
Fechheimer et al., *Proc. Natl. Acad. Sci. USA*, 84:8463-8467, 1987.
Ferkol et al., *FASEB J*, 7:1081-1091, 1993.
Fraley et al, *Proc. Natl. Acad. Sci. USA*, 76:3348-3352, 1979.
Freedman et al., WO 94/17178 (Aug, 4, 1994)
Frixen et al., *J. Cell Biol.*, 113:173-185, 1991.
Garnier et al., *Cytotechnol.*, 15:145-155, 1994.
Ghosh and Bachhawat, In: Wu G, Wu C ed. Liver diseases, targeted diagnosis and therapy using specific receptors and ligands. New York: Marcel Dekker, pp. 87-104, 1991.
Giancotti and Ruoslahti, *Cell*, 60:849-859, 1990.
Gilbert, "Adaptation of cells to serum free culture for production of adenovirus vectors and recombinant proteins," *Williamsburg BioProcessing Conference*, Nov. 18-21, 1996.
Gopal, *Mol. Cell Biol.*, 5:1188-1190, 1985.
Graham and Prevec, In: Methods in Molecular Biology: Gene Transfer and Expression Protocols 7. Murray, E. J. Editors. Clifton, N. J.: Humana Press, 109-128 and 205-225, 1991.
Graham and Van Der E b, *Virology* 52:456467, 1973.
Graham et al, *Journal of General Virology*, 36:59-74, 1977.
Graham, *J. Gen. Virol.*, 68:93 7-940, 1987.
Griffiths, J. B., In *"Animal Cell Biotechnology"*, vol. 3, p179-220, (Eds. Spier, R. E. and Griffiths, J. B.), Academic Press, London., 1986
Harland and Weintraub, *J. Cell Biol.*, 101:1094-1099, 1985.
Hay et al., *Journal of Molecular Biology*, 175:493-510, 1984.
Hearing and Shenk, *Journal of Molecular Biology*, 167:809-822, 1983.
Hearing et al., *Journal of Virology*, 67:2555-2558, 1987.
Hermonat and Muzycska, *Proc. Nat. Acad. Sci. USA*, 81:6466-6470, 1984.
Hollestein et al., *Science*, 253:49-53 1991.
Hussussian et al., *Nature Genetics*, 15-21, 1994.
Huyghe et al., Human Gene Therapy, 6:1403-1416, 1996.
Jones and Shenk, *Cell*, 13:181-188, 1978.
Kamb et al., *Nature Genetics*, 8:22-26, 1994.
Kamb et al., *Science*, 2674:436-440, 1994.
Kaneda et al., *Science*, 243:375-378, 1989.
Kato et al., *J. Biol. Chem.*, 266:3361-3364, 1991.
Klein et al., *Nature*, 327:70-73, 1987.
Larsson and Litwin, *Dev. Biol. Standard.*, 66:385-390, 1987.
Levrero et al., *Gene*, 101:195-202, 1991.
Lim, U.S. Pat. No. 4,352,883, Oct. 5, 1982.
Lin and Guidotti, *J. Biol. Chem.*, 264:14408-14414, 1989.
Mann et al., *Cell*, 33:153-159, 1983.
Matsura et al., *Brit. J. Cancer*, 66:1122-1130, 1992.
McGrath et al., J. Virol., 25: 923-927, 1978.
Mercer, *Critic. Rev. Eukar. Gene Express.* 2:251-263, 1992.
Mizrahi, *Process Biochem.*, (August):9-12, 1983.
Montenarh, *Crit. Rev. Oncogen*, 3:233-256, 1992.
Mori et al., *Cancer Res.*, 54:3396-3397, 1994.
Morris et al., "Serum-free production of adenoviral vectors for gene therapy," *Williamsburg BioProcessing Conference*, Nov. 18-21, 1996.
Myers, EPO 0273085
Nicolas and Rubenstein, In: Rodriguez R L, Denhardt D T, ed. Vectors: A survey of molecular cloning vectors and their uses. Stoneham: Butterworth, pp. 493-513, 1988.
Nicolau and Sene, *Biochem. Biophys. Acta*, 721:185-190, 1982.
Nicolau et al., *Methods Enzymol.*, 149:157-176, 1987.
Nilsson and Mosbach, *Dev. Biol. Standard*, 66:183-193,
Nobri et al., *Nature (London)*, 368:753-756, 1995.
O'Neil and Balkovic, *Bio/Technol.*, 11:173-178, 1993.
Obrink, *BioEssays.*, 13:227-233, 1991.
Odin and Obrink, *Exp. Cell Res.*, 171:1-15, 1987.
Okamoto et al., *Proc. Natl. Acad Sci. USA*, 91:11045-11049, 1994.
Orlow et al., *Cancer Res.*, 54:2848-2851, 1994.
Paskind et al., *Virology*, 67:242-248, 1975.
Perales et al., Proc. Natl. Acad. Sci. USA, 91:4086-4090, 1994.
Perrin et al., *Vaccine*, 13(13):1244-1250, 1995.
Petricciani, *Dev. Biol. Standard*, 66:3-12, 1985.
Phillips et al., *In: Large Scale Mammalian Cell Culture* (Feder, J. and Tolbert, W. R., eds.), Academic Press, Orlando, Fla., USA, 1985.
Potter et al., *Proc. Nat. Acad. Sci. USA*, 81:7161-7165, 1984.
Renan, *Radiother. Oncol.*, 19:197-218, 1990.
Ridgeway, In: Rodriguez R L, Denhardt D T, ed. Vectors: A survey of molecular cloning vectors and their uses. Stoneham: Butterworth, pp. 467492, 1988.
Rippe et al. *Mol. Cell Biol.*, 10:689-695, 1990.
Roux et al. *Proc. Nat'l Acad. Sci. USA*, 86:9079-9083, 1989.
Serrano et al., *Nature*, 366:704-707, 1993.
Serrano et al., *Science*, 267:249-252, 1995.
Smith and Lee, *Analytical Biochem.*, 86: 252-263, 1978.
Takahashi et al., *Cancer Res.*, 52:2340-2342, 1992.
Temin, In: Kucherlapati R, ed. Gene transfer. New York: Plenum Press, pp. 149-188, 1986.
Tibbetts, *Cell*, 12:243-249, 1977.
Tur-Kaspa et al., *Mol. Cell Biol.*, 6:716-718, 1986.
Umbas et al., *Cancer Res.*, 52:5104-5109, 1992.
van Wezel, *Nature*, 216:64-65, 1967.
Wagner et al., *Proc. Nat'l Acad. Sci.*, 87(9):3410-3414, 1990.
Wagner et al., *Science*, 260:1510-1513, 1993.
Wang et al., In: Animal Cell Technology: Basic & Applied Aspects, S. Kaminogawa et al., (eds), vol. 5, pp463-469, Kluwer Academic Publishers, Netherlands, 1993.
Wang et al., Cytotechnology, 9:41-49, 1992.
Wang et al., Proceeding of the Japanese Society for Animal Cell Technology, 1994.
Watt et al., *Proc. Nat'l Acad. Sci.*, 83(2):3166-3170, 1986.
Weinberg, R. A., *Science*, 254:1138-1146, 1991.
Wong et al., *Gene*, 10:87-94, 1980.
Wu and Wu, *J. Biol. Chem.*, 262:4429-4432, 1987.
Wu and Wu, *Adv. Drug Delivery Rev.*, 12:159-167, 1993.
Wu and Wu, *Biochemistry*, 27:887-892, 1988.
Yang et al., *Proc. Nat'l Acad. Sci. USA*, 87:9568-9572, 1990.

What is claimed is:

1. A method for making a purified adenovirus composition for therapeutic use comprising:
   a) growing host cells in a media comprising glucose wherein nutrients are provided to said host cells by perfusion or through a fed-batch process;
   b) infecting said host cells with an adenovirus;
   c) lysing said host cells by a lysis method other than freeze-thaw to produce a lysate comprising said adenovirus composition; and
   d) purifying adenovirus from said lysate to provide a purified adenovirus composition for therapeutic use
   wherein the purified adenovirus composition for therapeutic use has a contaminating nucleic acid content of less than 400 pg per $10^{10}$ pfu of virus and greater than or equal to about 60 pg per $10^{10}$ pfu of virus.

2. The method of claim 1, wherein the purified adenovirus composition for therapeutic use comprises 70%+/−10% of the starting PFU.

3. The method of claim 1, wherein the purified adenovirus composition for therapeutic use comprises a substantially purified therapeutic adenovirus composition.

4. The method of claim 1, wherein the purified adenovirus composition for therapeutic use has a contaminating nucleic acid concentration of less than 0.8 ng/ml.

5. The method of claim 1, wherein the purified adenovirus composition for therapeutic use has a contaminating nucleic acid concentration of less than 0.2 ng/ml.

6. The method of claim 1, wherein the purified adenovirus composition for therapeutic use has an $A_{260}/A_{280}$ ratio of between about 1.2 and 1.3.

7. The method of claim 1, wherein the purified adenovirus composition for therapeutic use has an $A_{260}/A_{280}$ ratio of 1.27+/−0.03.

8. The method of claim 1, wherein the purified adenovirus composition for therapeutic use has a contaminating nucleic acid concentration of less than 0.8 ng/ml and an $A_{260}/A_{280}$ ratio of between about 1.2 and 1.3.

9. The method of claim 1, wherein the media is serum-free.

10. The method of claim 1, wherein the host cells are grown in a bioreactor.

11. The method of claim 1, wherein the host cells are grown on microcarriers.

12. The method of claim 1, wherein said purified adenovirus composition for therapeutic use comprises an adenoviral vector encoding an exogenous gene construct.

13. The method of claim 12, wherein said exogenous gene construct is operatively linked to a promoter.

14. The method of claim 13, wherein said promoter is SV40 IE, RSV LTR, β-actin, CMV IE, adenovirus major late, polyoma F9-1, or tyrosinase.

15. The method of claim 12, wherein said exogenous gene construct encodes a therapeutic gene.

16. The method of claim 15, wherein said therapeutic gene encodes antisense ras, antisense myc, antisense raf, antisense erb, antisense src, antisense fms, antisense jun, antisense trk, antisense ret, antisense gsp, antisense hst, antisense bcl, antisense abl, Rb, CFTR, p16, p21, p27, p57, p73, C-CAM, APC, CTS-1, zac1, scFV ras, DCC, NF-1, NF-2, WT-1, MEN-1, MEN II, BRCA1, VHL, MMAC1, FCC, MCC, BRCA2, IL-1, IL-2, IL-3, IL-4, IL-5, IL-6, IL-7, IL-8, IL-9, IL-10, IL-11, IL-12, GM-CSF, G-CSF, thymidine kinase or p53.

17. The method of claim 16, wherein said therapeutic gene encodes p53.

18. The method of claim 1, wherein said purified adenovirus composition for therapeutic use is a replication-incompetent adenovirus.

19. The method of claim 18, wherein said purified adenovirus composition for therapeutic use is lacking at least a portion of the E1-region.

20. The method of claim 19, wherein the purified adenovirus composition for therapeutic use is lacking at least a portion of the E1A and/or E1B region.

21. The method of claim 1, wherein said host cells are capable of complementing replication.

22. The method of claim 1, wherein said host cells are 293 cells.

23. The method of claim 1, wherein said lysate is treated with a nuclease.

24. The method of claim 1, wherein said purified adenovirus composition for therapeutic use comprises a pharmaceutically acceptable buffer.

25. The method of claim 24, wherein said purified adenovirus composition for therapeutic use provides a unit dose of between $10^3$ and $10^{15}$ PFU/dose.

26. The method of claim 24, wherein the purified adenovirus composition for therapeutic use provides a unit dose of between $10^{10}$ and $10^{14}$ PFU/dose.

27. The method of claim 1, wherein said purifying is characterized by a process that includes at least one chromatography step capable of providing a purified therapeutic adenovirus composition.

28. The method of claim 1, wherein said purifying is characterized by a process that includes a single chromatography step capable of providing a purified therapeutic adenovirus composition.

29. The method of claim 1, wherein the lysis method other than freeze-thaw is a process that includes hypotonic solution, hypertonic solution, impinging jet, microfluidization, detergent, liquid shear, high pressure extrusion, autolysis or sonication to produce a crude lysate composition comprising adenovirus.

* * * * *